US012774459B2

(12) United States Patent
Kohane et al.

(10) Patent No.: US 12,774,459 B2
(45) Date of Patent: Oct. 27, 2026

(54) TRUNCATED MODIFIED RECOMBINANT ADAMTS13 AND USES THEREOF

(71) Applicants: Children's Medical Center Corporation, Boston, MA (US); The United States of America, as represented by the Secretary, Department of Health and Human Services, Silver Spring, MD (US)

(72) Inventors: Daniel S. Kohane, Newton, MA (US); Juan C. Ibla, Medfield, MA (US); Upendra Katneni, Clarksburg, MD (US); Chava Kimchi-Sarfaty, North Potomac, MD (US)

(73) Assignees: Children's Medical Center Corporation, Boston, MA (US); The United States of America, as represented by the Secretary, Department of Health and Human Services, Silver Spring, MD (US)

( * ) Notice: Subject to any disclaimer, the term of this patent is extended or adjusted under 35 U.S.C. 154(b) by 455 days.

(21) Appl. No.: 18/034,136

(22) PCT Filed: Oct. 28, 2021

(86) PCT No.: PCT/US2021/057013
§ 371 (c)(1),
(2) Date: Apr. 27, 2023

(87) PCT Pub. No.: WO2022/094051
PCT Pub. Date: May 5, 2022

(65) Prior Publication Data

US 2024/0067947 A1 Feb. 29, 2024

Related U.S. Application Data

(60) Provisional application No. 63/106,699, filed on Oct. 28, 2020.

(51) Int. Cl.
*C12N 9/64* (2006.01)
*A61K 9/50* (2006.01)
*A61K 38/48* (2006.01)

(52) U.S. Cl.
CPC .......... *C12N 9/6489* (2013.01); *A61K 9/5031* (2013.01); *A61K 38/4886* (2013.01); *C12Y 304/24087* (2013.01)

(58) Field of Classification Search
CPC .......... C12N 9/6489; C12Y 304/24087; A61K 38/4886
See application file for complete search history.

(56) References Cited

U.S. PATENT DOCUMENTS 8,999,380 B2 * 4/2015 Bancel ............... A61K 38/1891 530/358
2012/0108651 A1 * 5/2012 Bare ......................... A61P 7/02 514/355

FOREIGN PATENT DOCUMENTS

CN 104926946 A 9/2015
JP 2020-513420 A 5/2020
WO 2008/151154 A1 12/2008

OTHER PUBLICATIONS

Result 1, SEQ ID No. 7 95.1% sim to SEQ ID 780 (U.S. Pat. No. 8999380) (Year: 2015).*
Result 8, SEQ ID No. 7 95.1% sim to SEQ ID 125 (US 2012/0108651) (Year: 2012).*
Kremer et al., Hereditary Thrombotic Thrombocytopenia Purpura. N Engl J Med. Oct. 24, 2019;381(17):1653-1662. doi: 10.1056/NEJMra1813013.
Bali et al., Decoding mechanisms by which silent codon changes influence protein biogenesis and function. Int J Biochem Cell Biol. Jul. 2015;64:58-74. doi: 10.1016/j.biocel.2015.03.011. Epub Mar. 26, 2015.
De Maeyer et al., The distal carboxyterminal domains of murine ADAMTS13 influence proteolysis of platelet-decorated VWF strings in vivo. J Thromb Haemost. Oct. 2010;8(10):2305-12. doi: 10.1111/j.1538-7836.2010.04008.x.
Denorme et al., ADAMTS13-mediated thrombolysis of t-PA-resistant occlusions in ischemic stroke in mice. Blood. May 12, 2016;127(19):2337-45. doi: 10.1182/blood-2015-08-662650.
Ercig et al., Insights into 3D Structure of ADAMTS13: A Stepping Stone towards Novel Therapeutic Treatment of Thrombotic Thrombocytopeniaurpura. Thromb Haemost. Jan. 2018;118(1):28-41. doi: 10.1160/TH17-06-0404. Epub Jan. 5, 2018.
Jin et al., AAV-mediated expression of an ADAMTS13 variant prevents shigatoxin-induced thrombotic thrombocytopenia purpura. Blood. May 9, 2013;121(19):3825-9, S1-3. doi: 10.1182/blood-2013-02-486779. Epub Mar. 20, 2013.
Niiya et al., Correction of ADAMTS13 deficiency by in utero gene transfer of lentiviral vector encoding ADAMTS13 genes. Mol Ther. Jan. 2009;17(1):34-41. doi: 10.1038/mt.2008.223. Epub Oct. 28, 2008.
Rossato et al., Absence of exaggerated pharmacology by recombinant ADAMTS13 in the rat and monkey. Blood Coagul Fibrinolysis. Jan. 1, 2022;33(1):56-60. doi: 10.1097/MBC.0000000000001064.
Scully et al., Recombinant ADAMTS-13: first-in-human pharmacokinetics and safety in congenital thrombotic thrombocytopenia purpura. Blood. Nov. 9, 2017;130(19):2055-2063. doi: 10.1182/blood-2017-06-788026.

(Continued)

*Primary Examiner* — Ruth A Davis
(74) *Attorney, Agent, or Firm* — Wolf, Greenfield & Sacks, P.C.

(57) ABSTRACT

Provided herein are polypeptides that are truncated modified recombinant forms of ADAMTS13, nucleic acid molecules encoding the polypeptides, drug delivery compositions and pharmaceutical compositions comprising the polypeptides, and methods of using the polypeptides and compositions (e.g., in the treatment of thrombotic thrombocytopenic purpura (TTP)).

21 Claims, 14 Drawing Sheets

Specification includes a Sequence Listing.

(56) References Cited

OTHER PUBLICATIONS

Soejima et al., ADAMTS-13 cysteine-rich/spacer domains are functionally essential for von Willebrand factor cleavage. Blood. Nov. 1, 2003;102(9):3232-7. doi: 10.1182/blood-2003-03-0908. Epub Jul. 17, 2003.
Sonneveld et al., Low ADAMTS-13 activity and the risk of coronary heart disease—a prospective cohort study: the Rotterdam Study. J Thromb Haemost. Nov. 2016;14(11):2114-2120. doi: 10.1111/jth.13479.
Sonneveld et al., Low ADAMTS13 activity is associated with an increased risk of ischemic stroke. Blood. Dec. 17, 2015;126(25):2739-46. doi: 10.1182/blood-2015-05-643338.
South et al., Conformational activation of ADAMTS13. Proc Natl Acad Sci U S A. Dec. 30, 2014;111(52):18578-83. doi: 10.1073/pnas.1411979112. Epub Dec. 15, 2014.
Zheng et al., Cleavage of von Willebrand factor requires the spacer domain of the metalloprotease ADAMTS13. J Biol Chem. Aug. 8, 2003;278(32):30136-41. doi: 10.1074/jbc.M305331200. Epub Jun. 5, 2003.
Zheng, Structure-function and regulation of ADAMTS-13 protease. J Thromb Haemost. Jun. 2013;11 Suppl 1(0 1):11-23. doi: 10.1111/jth.12221.
Zhou et al., Enzymatically active ADAMTS13 variants are not inhibited by anti-ADAMTS13 autoantibodies: a novel therapeutic strategy? J Biol Chem. Dec. 2, 2005;280(48):39934-41. doi: 10.1074/jbc.M504919200. Epub Oct. 3, 2005.

* cited by examiner

SEQUENCE LISTING

<160> NUMBER OF SEQ ID NOS: 11

<210> SEQ ID NO 1
<211> LENGTH: 4386
<212> TYPE: DNA
<213> ORGANISM: Artificial Sequence
<220> FEATURE:
<223> OTHER INFORMATION: Synthetic

<400> SEQUENCE: 1

```
atgcaccagc gtcacccccg ggcaagatgc cctcccctct gtgtggccgg aatccttgcc     60

tgtggctttc tcctgggctg ctggggaccc tcccatttcc agcagagttg tcttcaggct    120

ttggagccac aggccgtgtc ttcttacttg agccctggtg ctcccttaaa aggccgccct    180

ccttcccctg gcttccagag gcagaggcag aggcagaggc gggctgcagg cggcatccta    240

cacctggagc tgctggtggc cgtgggcccc gatgtcttcc aggctcacca ggaggacaca    300

gagcgctatg tgctcaccaa cctcaacatc ggggcagaac tgcttcggga cccgtccctg    360

ggggctcagt ttcgggtgca cctggtgaag atggtcattc tgacagagcc tgagggtgct    420

ccaaatatca cagccaacct cacctcgtcc ctgctgagcg tctgtgggtg gagccagacc    480

atcaaccctg aggacgacac ggatcctggc catgctgacc tggtcctcta tatcactagg    540

tttgacctgg agttgcctga tggtaaccgg caggtgcggg gcgtcaccca gctgggcggt    600

gcctgctccc caacctggag ctgcctcatt accgaggaca ctggcttcga cctgggagtc    660

accattgccc atgagattgg gcacagcttc ggcctggagc acgacggcgc gcccggcagc    720

ggctgcggcc ccagcggaca cgtgatggct tcggacggcg ccgcgccccg cgccggcctc    780

gcctggtccc cctgcagccg ccggcagctg ctgagcctgc tcagcgcagg acgggcgcgc    840

tgcgtgtggg acccgccgcg gcctcaaccc gggtccgcgg ggcacccgcc ggatgcgcag    900

cctggcctct actacagcgc caacgagcag tgccgcgtgg ccttcggccc caaggctgtc    960

gcctgcacct tcgccaggga gcacctggat atgtgccagg ccctctcctg ccacacagac   1020
```

-continued

```
ccgctggacc aaagcagctg cagccgcctc ctcgttcctc tcctggatgg gacagaatgt   1080
ggcgtggaga agtggtgctc caagggtcgc tgccgctccc tggtggagct gacccccata   1140
gcagcagtgc atgggcgctg gtctagctgg ggtccccgaa gtccttgctc ccgctcctgc   1200
ggaggaggtg tggtcaccag gaggcggcag tgcaacaacc ccagacctgc ctttgggggg   1260
cgtgcatgtg ttggtgctga cctccaggcc gagatgtgca acactcaggc ctgcgagaag   1320
acccagctgg agttcatgtc gcaacagtgc gccaggaccg acggccagcc gctgcgctcc   1380
tcccctggcg gcgcctcctt ctaccactgg ggtgctgctg taccacacag ccaaggggat   1440
gctctgtgca gacacatgtg ccgggccatt ggcgagagct tcatcatgaa gcgtggagac   1500
agcttcctcg atgggacccg gtgtatgcca agtggccccc gggaggacgg gaccctgagc   1560
ctgtgtgtgt cgggcagctg caggacattt ggctgtgatg gtaggatgga ctcccagcag   1620
gtatgggaca ggtgccaggt gtgtggtggg gacaacagca cgtgcagccc acggaagggc   1680
tctttcacag ctggcagagc gagagaatat gtcacgtttc tgacagttac ccccaacctg   1740
accagtgtct acattgccaa ccacaggcct ctcttcacac acttggcggt gaggatcgga   1800
gggcgctatg tcgtggctgg gaagatgagc atctccccta acaccaccta cccctccctc   1860
ctggaggatg gtcgtgtcga gtacagagtg gccctcaccg aggaccggct gccccgcctg   1920
gaggagatcc gcatctgggg acccctccag gaagatgctg acatccaggt ttacaggcgg   1980
tatggcgagg agtatggcaa cctcacccgc ccagacatca ccttcaccta cttccagcct   2040
aagccacggc aggcctgggt gtgggccgct gtgcgtgggc cctgctcggt gagctgtggg   2100
gcagggctgc gctgggtaaa ctacagctgc ctggaccagg ccaggaagga gttggtggag   2160
actgtccagt gccaagggag ccagcagcca ccagcgtggc cagaggcctg cgtgctcgaa   2220
ccctgccctc cctactgggc ggtgggagac ttcggcccat gcagcgcctc ctgtgggggt   2280
ggcctgcggg agcggccagt gcgctgcgtg gaggcccagg gcagcctcct gaagacattg   2340
cccccagccc ggtgcagagc aggggcccag cagccagctg tggcgctgga aacctgcaac   2400
ccccagccct gccctgccag gtgggaggtg tcagagccca gctcatgcac atcagctggt   2460
ggagcaggcc tggccttgga gaacgagacc tgtgtgccag gggcagatgg cctggaggct   2520
ccagtgactg aggggcctgg ctccgtagat gagaagctgc ctgcccctga gccctgtgtc   2580
gggatgtcat gtcctccagg ctggggccat ctggatgcca cctctgcagg ggagaaggct   2640
ccctccccat ggggcagcat caggacgggg gctcaagctg cacacgtgtg gacccctgcg   2700
gcagggtcgt gctccgtctc ctgcgggcga ggtctgatgg agctgcgttt cctgtgcatg   2760
gactctgccc tcagggtgcc tgtccaggaa gagctgtgtg gcctggcaag caagcctggg   2820
agccggcggg aggtctgcca ggctgtcccg tgccctgctc ggtggcagta caagctggcg   2880
gcctgcagcg tgagctgtgg gagaggggtc gtgcggagga tcctgtattg tgcccgggcc   2940
catggggagg acgatggtga ggagatcctg ttggacaccc agtgccaggg gctgcctcgc   3000
ccggaacccc aggaggcctg cagcctggag ccctgcccac ctaggtggaa agtcatgtcc   3060
cttggcccat gttcggccag ctgtggcctt ggcactgcta gacgctcggt ggcctgtgtg   3120
cagctcgacc aaggccagga cgtggaggtg gacgaggcgg cctgtgcggc gctggtgcgg   3180
cccgaggcca gtgtcccctg tctcattgcc gactgcacct accgctggca tgttggcacc   3240
tggatggagt gctctgtttc ctgtggggat ggcatccagc gccggcgtga cacctgcctc   3300
ggaccccagg cccaggcgcc tgtgccagct gatttctgcc agcacttgcc caagccggtg   3360
actgtgcgtg gctgctgggc tgggccctgt gtgggacagg gtacgcccag cctggtgccc   3420
```

```
cacgaagaag ccgctgctcc aggacggacc acagccaccc ctgctggtgc ctccctggag   3480
tggtcccagg cccggggcct gctcttctcc ccggctcccc agcctcggcg gctcctgccc   3540
gggccccagg aaaactcagt gcagtccagt gcctgtggca ggcagcacct tgagccaaca   3600
ggaaccattg acatgcgagg cccagggcag gcagactgtg cagtggccat tgggcggccc   3660
ctcggggagg tggtgaccct ccgcgtcctt gagagttctc tcaactgcag tgcgggggac   3720
atgttgctgc tttggggccg gctcacctgg aggaagatgt gcaggaagct gttggacatg   3780
actttcagct ccaagaccaa cacgctggtg gtgaggcagc gctgcgggcg gccaggaggt   3840
ggggtgctgc tgcggtatgg gagccagctt gctcctgaaa ccttctacag agaatgtgac   3900
atgcagctct ttgggccctg ggtgaaatc gtgagcccct cgctgagtcc agccacgagt    3960
aatgcagggg gctgccggct cttcattaat gtggctccgc acgcacggat tgccatccat   4020
gccctggcca ccaacatggg cgctgggacc gagggagcca atgccagcta catcttgatc   4080
cgggacaccc acagcttgag gaccacagcg ttccatgggc agcaggtgct ctactgggag   4140
tcagagagca gccaggctga gatggagttc agcgagggct tcctgaaggc tcaggccagc   4200
ctgcggggcc agtactggac cctccaatca tgggtaccgg agatgcagga ccctcagtcc   4260
tggaagggaa aggaaggaac caagggcgag cttggtaccg agctcggatc cgaaggtaag   4320
cctatcccta accctctcct cggtctcgat tctacgcgta ccggtcatca tcaccatcac   4380
cattga                                                              4386
```

<210> SEQ ID NO 2
<211> LENGTH: 2160
<212> TYPE: DNA
<213> ORGANISM: Artificial Sequence
<220> FEATURE:
<223> OTHER INFORMATION: Synthetic

<400> SEQUENCE: 2

```
atgcaccagc gtcacccccg ggcaagatgc cctcccctct gtgtggccgg aatccttgcc     60
tgtggctttc tcctgggctg ctggggaccc tcccatttcc agcagagttg tcttcaggct    120
ttggagccac aggccgtgtc ttcttacttg agccctggtg ctcccttaaa aggccgccct    180
ccttcccctg gcttccagag gcagaggcag aggcagaggc gggctgcagg cggcatccta    240
cacctggagc tgctggtggc cgtgggcccc gatgtcttcc aggctcacca ggaggacaca    300
gagcgctatg tgctcaccaa cctcaacatc ggggcagaac tgcttcggga cccgtccctg    360
ggggctcagt ttcgggtgca cctggtgaag atggtcattc tgacagagcc tgagggtgct    420
ccaaatatca cagccaacct cacctcgtcc ctgctgagcg tctgtgggtg gagccagacc    480
atcaaccctg aggacgacac ggatcctggc catgctgacc tggtcctcta tatcactagg    540
tttgacctgg agttgcctga tggtaaccgg caggtgcggg gcgtcaccca gctgggcggt    600
gcctgctccc caacctggag ctgcctcatt accgaggaca ctggcttcga cctgggagtc    660
accattgccc atgagattgg gcacagcttc ggcctggagc acgacggcgc gcccggcagc    720
ggctgcggcc ccagcggaca cgtgatggct tcggacggcg ccgcgccccg cgccggcctc    780
gcctggtccc cctgcagccg ccggcagctg ctgagcctgc tcagcgcagg acgggcgcgc    840
tgcgtgtggg acccgccgcg gcctcaaccc gggtccgcgg ggcacccgcc ggatgcgcag    900
cctggcctct actacagcgc caacgagcag tgccgcgtgg ccttcggccc caaggctgtc    960
gcctgcacct tcgccaggga gcacctggat atgtgccagg ccctctcctg ccacacagac   1020
```

```
ccgctggacc aaagcagctg cagccgcctc ctcgttcctc tcctggatgg gacagaatgt   1080
ggcgtggaga agtggtgctc caagggtcgc tgccgctccc tggtggagct gacccccata   1140
gcagcagtgc atgggcgctg gtctagctgg ggtccccgaa gtccttgctc ccgctcctgc   1200
ggaggaggtg tggtcaccag gaggcggcag tgcaacaacc ccagacctgc ctttgggggg   1260
cgtgcatgtg ttggtgctga cctccaggcc gagatgtgca acactcaggc ctgcgagaag   1320
acccagctgg agttcatgtc gcaacagtgc gccaggaccg acggccagcc gctgcgctcc   1380
tcccctggcg gcgcctcctt ctaccactgg ggtgctgctg taccacacag ccaaggggat   1440
gctctgtgca gacacatgtg ccgggccatt ggcgagagct tcatcatgaa gcgtggagac   1500
agcttcctcg atgggacccg gtgtatgcca agtggccccc gggaggacgg gaccctgagc   1560
ctgtgtgtgt cgggcagctg caggacattt ggctgtgatg gtaggatgga ctcccagcag   1620
gtatgggaca ggtgccaggt gtgtggtggg gacaacagca cgtgcagccc acggaagggc   1680
tctttcacag ctggcagagc gagagaatat gtcacgtttc tgacagttac ccccaacctg   1740
accagtgtct acattgccaa ccacaggcct ctcttcacac acttggcggt gaggatcgga   1800
gggcgctatg tcgtggctgg gaagatgagc atctccccta acaccaccta cccctccctc   1860
ctggaggatg gtcgtgtcga gtacagagtg gccctcaccg aggaccggct gccccgcctg   1920
gaggagatcc gcatctgggg acccctccag gaagatgctg acatccaggt ttacaggcgg   1980
tatggcgagg agtatggcaa cctcacccgc ccagacatca ccttcaccta cttccagcct   2040
aagccacggc aggccaaggg cgagcttggt accgagctcg gatccgaagg taagcctatc   2100
cctaaccctc tcctcggtct cgattctacg cgtaccggtc atcatcacca tcaccattga   2160
```

<210> SEQ ID NO 3
<211> LENGTH: 2160
<212> TYPE: DNA
<213> ORGANISM: Artificial Sequence
<220> FEATURE:
<223> OTHER INFORMATION: Synthetic

<400> SEQUENCE: 3

```
atgcatcaga gacatccacg ggctaggtgt cctccactgt gcgtcgctgg catcctggct     60
tgcgggttcc tgctgggctg ctgggggcct agccacttcc agcagtcctg cctgcaggcc    120
ctggagccac aggccgtgag ctcctacctg agccctggag caccactgaa gggcagaccc    180
ccttcccctg gcttccagag acagaggcag aggcagagga gagcagcagg aggcatcctg    240
cacctggagc tgctggtggc agtgggacca gacgtgtttc aggcccacca ggaggatacc    300
gagagatatg tgctgacaaa cctgaatatc ggcgccgagc tgctgaggga ccccagcctg    360
ggagcacagt tccgcgtgca cctggtgaag atggtcatcc tgaccgagcc tgagggagct    420
ccaaacatca ccgccaatct gacatctagc ctgctgagcg tgtgcggctg gagccagacc    480
atcaaccctg aggacgatac agacccaggc cacgccgatc tggtgctgta catcaccaga    540
tttgacctgg agctgccaga tggcaatagg caggtgcgcg gagtgaccca gctgggagga    600
gcatgttccc caacatggtc ttgcctgatc accgaggaca caggcttcga tctgggcgtg    660
acaatcgccc acgagatcgg ccactccttt ggcctggagc acgacggagc accaggatcc    720
ggatgcggac cttctggaca cgtgatggca tctgatggag cagcaccaag ggcaggcctg    780
gcatggtccc cctgttctag gcgccagctg ctgagcctgc tgtccgccgg aagggccaga    840
tgcgtgtggg acccacccag accccagcct ggaagcgccg gccaccctcc agatgcccag    900
cccggcctgt actattccgc caacgagcag tgtagggtgg ccttcggccc taaggcagtg    960
```

gcatgcacct ttgccagaga gcacctggac atgtgccagg ccctgtcctg tcacacagac 1020
cccctggatc agtcctcttg ttctaggctg ctggtgcctc tgctggatgg caccgagtgc 1080
ggcgtggaga agtggtgcag caagggcagg tgtcgctccc tggtggagct gacaccaatc 1140
gcagcagtgc acggccgctg gagctcctgg ggaccacgga gcccttgctc cagatcttgt 1200
ggaggaggag tggtgacccg gagaaggcag tgtaacaatc caaggcccgc ctttggcgga 1260
agggcatgcg tgggagcaga cctgcaggcc gagatgtgca atacccaggc ctgtgagaag 1320
acacagctgg agttcatgtc ccagcagtgc gcaaggaccg acggacagcc actgagatct 1380
agccctggag gagcatcttt ttatcactgg ggagcagcag tgccacacag ccagggcgat 1440
gcactgtgca ggcacatgtg ccgcgccatc ggcgagtctt tcatcatgaa gcggggcgac 1500
agctttctgg atggaaccag gtgtatgcca tccggaccaa gggaggatgg caccctgtct 1560
ctgtgcgtga gcggctcctg tcggacattc ggctgcgacg gcagaatgga tagccagcaa 1620
gtgtgggaca ggtgccaggt gtgcggaggc gataactcta cctgcagccc taggaaggga 1680
tctttcacag caggaagggc aagagagtac gtgacgtttc tgaccgtgac accaaacctg 1740
acaagcgtgt atatcgccaa tcacaggccc ctgtttaccc acctggccgt gcggatcgga 1800
ggcagatacg tggtggcagg caagatgtct atcagcccaa ataccacata cccatccctg 1860
ctggaggacg gaagggtgga gtatcgcgtg gccctgacag aggatcggct gcctagactg 1920
gaggagatca ggatctgggg accactgcag gaggacgccg atatccaggt gtaccgccgg 1980
tatggcgagg agtatggcaa tctgactcgc cccgacatca ctttcacata cttccagccc 2040
aaaccaaggc aggcaaaggg cgagcttggt accgagctcg gatccgaagg taagcctatc 2100
cctaaccctc tcctcggtct cgattctacg cgtaccggtc atcatcacca tcaccattga 2160

<210> SEQ ID NO 4
<211> LENGTH: 7149
<212> TYPE: DNA
<213> ORGANISM: Artificial Sequence
<220> FEATURE:
<223> OTHER INFORMATION: Synthetic

<400> SEQUENCE: 4
gacggatcgg gagatctccc gatcccctat ggtgcactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggag tatttacggt aaactgccca cttggcagta catcaagtgt 480
atcatatgcc aagtacgccc cctattgacg tcaatgacgg taaatggccc gcctggcatt 540
atgcccagta catgacctta tgggactttc ctacttggca gtacatctac gtattagtca 600
tcgctattac catggtgatg cggttttggc agtacatcaa tgggcgtgga tagcggtttg 660
actcacgggg atttccaagt ctccacccca ttgacgtcaa tgggagtttg ttttggcacc 720
aaaatcaacg ggactttcca aaatgtcgta acaactccgc cccattgacg caaatgggcg 780
gtaggcgtgt acggtgggag gtctatataa gcagagctct ctggctaact agagaaccca 840

-continued

```
ctgcttactg gcttatcgaa attaatacga ctcactatag ggagacccaa gctggctagc    900
gtttaaactt aagctcgccc ttatgcatca gagacatcca cgggctaggt gtcctccact    960
gtgcgtcgct ggcatcctgg cttgcgggtt cctgctgggc tgctgggggc ctagccactt   1020
ccagcagtcc tgcctgcagg ccctggagcc acaggccgtg agctcctacc tgagccctgg   1080
agcaccactg aagggcagac cccettcccc tggcttccag agacagaggc agaggcagag   1140
gagagcagca ggaggcatcc tgcacctgga gctgctggtg gcagtgggac cagacgtgtt   1200
tcaggcccac caggaggata ccgagagata tgtgctgaca aacctgaata tcggcgccga   1260
gctgctgagg gaccccagcc tgggagcaca gttccgcgtg cacctggtga agatggtcat   1320
cctgaccgag cctgagggag ctccaaacat caccgccaat ctgacatcta gcctgctgag   1380
cgtgtgcggc tggagccaga ccatcaaccc tgaggacgat acagacccag gccacgccga   1440
tctggtgctg tacatcacca gatttgacct ggagctgcca gatggcaata ggcaggtgcg   1500
cggagtgacc cagctgggag gagcatgttc ccaacatgg tcttgcctga tcaccgagga   1560
cacaggcttc gatctgggcg tgacaatcgc ccacgagatc ggccactcct ttggcctgga   1620
gcacgacgga gcaccaggat ccggatgcgg accttctgga cacgtgatgg catctgatgg   1680
agcagcacca agggcaggcc tggcatggtc cccctgttct aggcgccagc tgctgagcct   1740
gctgtccgcc ggaagggcca gatgcgtgtg ggacccaccc agaccccagc ctggaagcgc   1800
cggccaccct ccagatgccc agcccggcct gtactattcc gccaacgagc agtgtagggt   1860
ggccttcggc cctaaggcag tggcatgcac ctttgccaga gagcacctgg acatgtgcca   1920
ggccctgtcc tgtcacacag accccctgga tcagtcctct tgttctaggc tgctggtgcc   1980
tctgctggat ggcaccgagt gcggcgtgga gaagtggtgc agcaagggca ggtgtcgctc   2040
cctggtggag ctgacaccaa tcgcagcagt gcacggccgc tggagctcct ggggaccacg   2100
gagcccttgc tccagatctt gtggaggagg agtggtgacc cggagaaggc agtgtaacaa   2160
tccaaggccc gcctttggcg gaagggcatg cgtgggagca gacctgcagg ccgagatgtg   2220
caatacccag gcctgtgaga agacacagct ggagttcatg tcccagcagt gcgcaaggac   2280
cgacggacag ccactgagat ctagccctgg aggagcatct ttttatcact ggggagcagc   2340
agtgccacac agccagggcg atgcactgtg caggcacatg tgccgcgcca tcggcgagtc   2400
tttcatcatg aagcggggcg acagctttct ggatggaacc aggtgtatgc catccggacc   2460
aagggaggat ggcaccctgt ctctgtgcgt gagcggctcc tgtcggacat tcggctgcga   2520
cggcagaatg gatagccagc aagtgtggga caggtgccag gtgtgcggag gcgataactc   2580
tacctgcagc cctaggaagg gatctttcac agcaggaagg gcaagagagt acgtgacgtt   2640
tctgaccgtg acaccaaacc tgacaagcgt gtatatcgcc aatcacaggc ccctgtttac   2700
ccacctggcc gtgcggatcg gaggcagata cgtggtggca ggcaagatgt ctatcagccc   2760
aaataccaca tacccatccc tgctggagga cggaagggtg gagtatcgcg tggccctgac   2820
agaggatcgg ctgcctagac tggaggagat caggatctgg ggaccactgc aggaggacgc   2880
cgatatccag gtgtaccgcc ggtatggcga ggagtatggc aatctgactc gccccgacat   2940
cactttcaca tacttccagc ccaaaccaag gcaggcaaag ggcgagcttg gtaccgagct   3000
cggatccgaa ggtaagccta tccctaaccc tctcctcggt ctcgattcta cgcgtaccgg   3060
tcatcatcac catcaccatt gagtttaaac ccgctgatca gcctcgactg tgccttctag   3120
ttgccagcca tctgttgttt gcccctcccc cgtgccttcc ttgaccctgg aaggtgccac   3180
tcccactgtc ctttcctaat aaaatgagga aattgcatcg cattgtctga gtaggtgtca   3240
```

```
ttctattctg gggggtgggg tggggcagga cagcaagggg gaggattggg aagacaatag   3300
caggcatgct ggggatgcgg tgggctctat ggcttctgag gcggaaagaa ccagctgggg   3360
ctctaggggg tatccccacg cgccctgtag cggcgcatta agcgcggcgg gtgtggtggt   3420
tacgcgcagc gtgaccgcta cacttgccag cgccctagcg cccgctcctt tcgctttctt   3480
cccttccttt ctcgccacgt tcgccggctt tccccgtcaa gctctaaatc gggggtccct   3540
ttagggttcc gatttagtgc tttacggcac ctcgacccca aaaaacttga ttagggtgat   3600
ggttcacgta cctagaagtt cctattccga agttcctatt ctctagaaag tataggaact   3660
tccttggcca aaaagcctga actcaccgcg acgtctgtcg agaagtttct gatcgaaaag   3720
ttcgacagcg tctccgacct gatgcagctc tcggagggcg aagaatctcg tgctttcagc   3780
ttcgatgtag gagggcgtgg atatgtcctg cgggtaaata gctgcgccga tggtttctac   3840
aaagatcgtt atgtttatcg gcactttgca tcggccgcgc tcccgattcc ggaagtgctt   3900
gacattgggg aattcagcga gagcctgacc tattgcatct cccgccgtgc acagggtgtc   3960
acgttgcaag acctgcctga aaccgaactg cccgctgttc tgcagccggt cgcggaggcc   4020
atggatgcga tcgctgcggc cgatcttagc cagacgagcg ggttcggccc attcggaccg   4080
caaggaatcg gtcaatacac tacatggcgt gatttcatat gcgcgattgc tgatccccat   4140
gtgtatcact ggcaaactgt gatggacgac accgtcagtg cgtccgtcgc gcaggctctc   4200
gatgagctga tgctttgggc cgaggactgc cccgaagtcc ggcacctcgt gcacgcggat   4260
ttcggctcca acaatgtcct gacggacaat ggccgcataa cagcggtcat tgactggagc   4320
gaggcgatgt tcggggattc ccaatacgag gtcgccaaca tcttcttctg gaggccgtgg   4380
ttggcttgta tggagcagca gacgcgctac ttcgagcgga ggcatccgga gcttgcagga   4440
tcgccgcggc tccgggcgta tatgctccgc attggtcttg accaactcta tcagagcttg   4500
gttgacggca atttcgatga tgcagcttgg gcgcagggtc gatgcgacgc aatcgtccga   4560
tccggagccg ggactgtcgg gcgtacacaa atcgcccgca gaagcgcggc cgtctggacc   4620
gatggctgtg tagaagtact cgccgatagt ggaaaccgac gccccagcac tcgtccgagg   4680
gcaaaggaat agcacgtact acgagatttc gattccaccg ccgccttcta tgaaaggttg   4740
ggcttcggaa tcgttttccg ggacgccggc tggatgatcc tccagcgcgg ggatctcatg   4800
ctggagttct tcgcccaccc caacttgttt attgcagctt ataatggtta caaataaagc   4860
aatagcatca caaatttcac aaataaagca tttttttcac tgcattctag ttgtggtttg   4920
tccaaactca tcaatgtatc ttatcatgtc tgtataccgt cgacctctag ctagagcttg   4980
gcgtaatcat ggtcatagct gtttcctgtg tgaaattgtt atccgctcac aattccacac   5040
aacatacgag ccggaagcat aaagtgtaaa gcctggggtg cctaatgagt gagctaactc   5100
acattaattg cgttgcgctc actgcccgct ttccagtcgg gaaacctgtc gtgccagctg   5160
cattaatgaa tcggccaacg cgcggggaga ggcggtttgc gtattgggcg ctcttccgct   5220
tcctcgctca ctgactcgct gcgctcggtc gttcggctgc ggcgagcggt atcagctcac   5280
tcaaaggcgg taatacggtt atccacagaa tcaggggata acgcaggaaa gaacatgtga   5340
gcaaaaggcc agcaaaaggc caggaaccgt aaaaaggccg cgttgctggc gtttttccat   5400
aggctccgcc cccctgacga gcatcacaaa aatcgacgct caagtcagag gtggcgaaac   5460
ccgacaggac tataaagata ccaggcgttt ccccctggaa gctccctcgt gcgctctcct   5520
gttccgaccc tgccgcttac cggatacctg tccgcctttc tcccttcggg aagcgtggcg   5580
```

```
ctttctcata gctcacgctg taggtatctc agttcggtgt aggtcgttcg ctccaagctg   5640
ggctgtgtgc acgaaccccc cgttcagccc gaccgctgcg ccttatccgg taactatcgt   5700
cttgagtcca acccggtaag acacgactta tcgccactgg cagcagccac tggtaacagg   5760
attagcagag cgaggtatgt aggcggtgct acagagttct tgaagtggtg gcctaactac   5820
ggctacacta gaaggacagt atttggtatc tgcgctctgc tgaagccagt taccttcgga   5880
aaaagagttg gtagctcttg atccggcaaa caaaccaccg ctggtagcgg tggttttttt   5940
gtttgcaagc agcagattac gcgcagaaaa aaaggatctc aagaagatcc tttgatcttt   6000
tctacggggt ctgacgctca gtggaacgaa aactcacgtt aagggatttt ggtcatgaga   6060
ttatcaaaaa ggatcttcac ctagatcctt ttaaattaaa aatgaagttt taaatcaatc   6120
taaagtatat atgagtaaac ttggtctgac agttaccaat gcttaatcag tgaggcacct   6180
atctcagcga tctgtctatt tcgttcatcc atagttgcct gactccccgt cgtgtagata   6240
actacgatac gggagggctt accatctggc cccagtgctg caatgatacc gcgagaccca   6300
cgctcaccgg ctccagattt atcagcaata aaccagccag ccggaagggc cgagcgcaga   6360
agtggtcctg caactttatc cgcctccatc cagtctatta attgttgccg ggaagctaga   6420
gtaagtagtt cgccagttaa tagtttgcgc aacgttgttg ccattgctac aggcatcgtg   6480
gtgtcacgct cgtcgtttgg tatggcttca ttcagctccg gttcccaacg atcaaggcga   6540
gttacatgat cccccatgtt gtgcaaaaaa gcggttagct ccttcggtcc tccgatcgtt   6600
gtcagaagta agttggccgc agtgttatca ctcatggtta tggcagcact gcataattct   6660
cttactgtca tgccatccgt aagatgcttt tctgtgactg gtgagtactc aaccaagtca   6720
ttctgagaat agtgtatgcg gcgaccgagt tgctcttgcc cggcgtcaat acgggataat   6780
accgcgccac atagcagaac tttaaaagtg ctcatcattg gaaaacgttc ttcggggcga   6840
aaactctcaa ggatcttacc gctgttgaga tccagttcga tgtaacccac tcgtgcaccc   6900
aactgatctt cagcatcttt tactttcacc agcgtttctg ggtgagcaaa aacaggaagg   6960
caaaatgccg caaaaaaggg aataagggcg acacggaaat gttgaatact catactcttc   7020
ctttttcaat attattgaag catttatcag ggttattgtc tcatgagcgg atacatattt   7080
gaatgtattt agaaaaataa acaaataggg gttccgcgca catttccccg aaaagtgcca   7140
cctgacgtc                                                           7149
```

<210> SEQ ID NO 5
<211> LENGTH: 1427
<212> TYPE: PRT
<213> ORGANISM: Artificial Sequence
<220> FEATURE:
<223> OTHER INFORMATION: Synthetic

<400> SEQUENCE: 5

```
Met His Gln Arg His Pro Arg Ala Arg Cys Pro Pro Leu Cys Val Ala
1               5                   10                  15

Gly Ile Leu Ala Cys Gly Phe Leu Leu Gly Cys Trp Gly Pro Ser His
            20                  25                  30

Phe Gln Gln Ser Cys Leu Gln Ala Leu Glu Pro Gln Ala Val Ser Ser
        35                  40                  45

Tyr Leu Ser Pro Gly Ala Pro Leu Lys Gly Arg Pro Pro Ser Pro Gly
    50                  55                  60

Phe Gln Arg Gln Arg Gln Arg Gln Arg Arg Ala Ala Gly Gly Ile Leu
65                  70                  75                  80
```

```
His Leu Glu Leu Leu Val Ala Val Gly Pro Asp Val Phe Gln Ala His
                85                  90                  95

Gln Glu Asp Thr Glu Arg Tyr Val Leu Thr Asn Leu Asn Ile Gly Ala
            100                 105                 110

Glu Leu Leu Arg Asp Pro Ser Leu Gly Ala Gln Phe Arg Val His Leu
        115                 120                 125

Val Lys Met Val Ile Leu Thr Glu Pro Glu Gly Ala Pro Asn Ile Thr
    130                 135                 140

Ala Asn Leu Thr Ser Ser Leu Leu Ser Val Cys Gly Trp Ser Gln Thr
145                 150                 155                 160

Ile Asn Pro Glu Asp Asp Thr Asp Pro Gly His Ala Asp Leu Val Leu
                165                 170                 175

Tyr Ile Thr Arg Phe Asp Leu Glu Leu Pro Asp Gly Asn Arg Gln Val
            180                 185                 190

Arg Gly Val Thr Gln Leu Gly Gly Ala Cys Ser Pro Thr Trp Ser Cys
        195                 200                 205

Leu Ile Thr Glu Asp Thr Gly Phe Asp Leu Gly Val Thr Ile Ala His
    210                 215                 220

Glu Ile Gly His Ser Phe Gly Leu Glu His Asp Gly Ala Pro Gly Ser
225                 230                 235                 240

Gly Cys Gly Pro Ser Gly His Val Met Ala Ser Asp Gly Ala Ala Pro
                245                 250                 255

Arg Ala Gly Leu Ala Trp Ser Pro Cys Ser Arg Arg Gln Leu Leu Ser
            260                 265                 270

Leu Leu Ser Ala Gly Arg Ala Arg Cys Val Trp Asp Pro Pro Arg Pro
        275                 280                 285

Gln Pro Gly Ser Ala Gly His Pro Pro Asp Ala Gln Pro Gly Leu Tyr
    290                 295                 300

Tyr Ser Ala Asn Glu Gln Cys Arg Val Ala Phe Gly Pro Lys Ala Val
305                 310                 315                 320

Ala Cys Thr Phe Ala Arg Glu His Leu Asp Met Cys Gln Ala Leu Ser
                325                 330                 335

Cys His Thr Asp Pro Leu Asp Gln Ser Ser Cys Ser Arg Leu Leu Val
            340                 345                 350

Pro Leu Leu Asp Gly Thr Glu Cys Gly Val Glu Lys Trp Cys Ser Lys
        355                 360                 365

Gly Arg Cys Arg Ser Leu Val Glu Leu Thr Pro Ile Ala Ala Val His
    370                 375                 380

Gly Arg Trp Ser Ser Trp Gly Pro Arg Ser Pro Cys Ser Arg Ser Cys
385                 390                 395                 400

Gly Gly Gly Val Val Thr Arg Arg Arg Gln Cys Asn Asn Pro Arg Pro
                405                 410                 415

Ala Phe Gly Gly Arg Ala Cys Val Gly Ala Asp Leu Gln Ala Glu Met
            420                 425                 430

Cys Asn Thr Gln Ala Cys Glu Lys Thr Gln Leu Glu Phe Met Ser Gln
        435                 440                 445

Gln Cys Ala Arg Thr Asp Gly Gln Pro Leu Arg Ser Ser Pro Gly Gly
    450                 455                 460

Ala Ser Phe Tyr His Trp Gly Ala Ala Val Pro His Ser Gln Gly Asp
465                 470                 475                 480

Ala Leu Cys Arg His Met Cys Arg Ala Ile Gly Glu Ser Phe Ile Met
                485                 490                 495

Lys Arg Gly Asp Ser Phe Leu Asp Gly Thr Arg Cys Met Pro Ser Gly
```

-continued

```
            500                 505                 510

Pro Arg Glu Asp Gly Thr Leu Ser Leu Cys Val Ser Gly Ser Cys Arg
        515                 520                 525

Thr Phe Gly Cys Asp Gly Arg Met Asp Ser Gln Gln Val Trp Asp Arg
    530                 535                 540

Cys Gln Val Cys Gly Gly Asp Asn Ser Thr Cys Ser Pro Arg Lys Gly
545                 550                 555                 560

Ser Phe Thr Ala Gly Arg Ala Arg Glu Tyr Val Thr Phe Leu Thr Val
                565                 570                 575

Thr Pro Asn Leu Thr Ser Val Tyr Ile Ala Asn His Arg Pro Leu Phe
            580                 585                 590

Thr His Leu Ala Val Arg Ile Gly Gly Arg Tyr Val Val Ala Gly Lys
        595                 600                 605

Met Ser Ile Ser Pro Asn Thr Thr Tyr Pro Ser Leu Leu Glu Asp Gly
    610                 615                 620

Arg Val Glu Tyr Arg Val Ala Leu Thr Glu Asp Arg Leu Pro Arg Leu
625                 630                 635                 640

Glu Glu Ile Arg Ile Trp Gly Pro Leu Gln Glu Asp Ala Asp Ile Gln
                645                 650                 655

Val Tyr Arg Arg Tyr Gly Glu Glu Tyr Gly Asn Leu Thr Arg Pro Asp
            660                 665                 670

Ile Thr Phe Thr Tyr Phe Gln Pro Lys Pro Arg Gln Ala Trp Val Trp
        675                 680                 685

Ala Ala Val Arg Gly Pro Cys Ser Val Ser Cys Gly Ala Gly Leu Arg
    690                 695                 700

Trp Val Asn Tyr Ser Cys Leu Asp Gln Ala Arg Lys Glu Leu Val Glu
705                 710                 715                 720

Thr Val Gln Cys Gln Gly Ser Gln Gln Pro Pro Ala Trp Pro Glu Ala
                725                 730                 735

Cys Val Leu Glu Pro Cys Pro Pro Tyr Trp Ala Val Gly Asp Phe Gly
            740                 745                 750

Pro Cys Ser Ala Ser Cys Gly Gly Gly Leu Arg Glu Arg Pro Val Arg
        755                 760                 765

Cys Val Glu Ala Gln Gly Ser Leu Leu Lys Thr Leu Pro Pro Ala Arg
    770                 775                 780

Cys Arg Ala Gly Ala Gln Gln Pro Ala Val Ala Leu Glu Thr Cys Asn
785                 790                 795                 800

Pro Gln Pro Cys Pro Ala Arg Trp Glu Val Ser Glu Pro Ser Ser Cys
                805                 810                 815

Thr Ser Ala Gly Gly Ala Gly Leu Ala Leu Glu Asn Glu Thr Cys Val
            820                 825                 830

Pro Gly Ala Asp Gly Leu Glu Ala Pro Val Thr Glu Gly Pro Gly Ser
        835                 840                 845

Val Asp Glu Lys Leu Pro Ala Pro Glu Pro Cys Val Gly Met Ser Cys
    850                 855                 860

Pro Pro Gly Trp Gly His Leu Asp Ala Thr Ser Ala Gly Glu Lys Ala
865                 870                 875                 880

Pro Ser Pro Trp Gly Ser Ile Arg Thr Gly Ala Gln Ala Ala His Val
                885                 890                 895

Trp Thr Pro Ala Ala Gly Ser Cys Ser Val Ser Cys Gly Arg Gly Leu
            900                 905                 910

Met Glu Leu Arg Phe Leu Cys Met Asp Ser Ala Leu Arg Val Pro Val
        915                 920                 925
```

```
Gln Glu Glu Leu Cys Gly Leu Ala Ser Lys Pro Gly Ser Arg Arg Glu
    930                 935                 940

Val Cys Gln Ala Val Pro Cys Pro Ala Arg Trp Gln Tyr Lys Leu Ala
945                 950                 955                 960

Ala Cys Ser Val Ser Cys Gly Arg Gly Val Val Arg Arg Ile Leu Tyr
                965                 970                 975

Cys Ala Arg Ala His Gly Glu Asp Asp Gly Glu Glu Ile Leu Leu Asp
            980                 985                 990

Thr Gln Cys Gln Gly Leu Pro Arg  Pro Glu Pro Gln Glu  Ala Cys Ser
        995                 1000                1005

Leu Glu  Pro Cys Pro Pro Arg  Trp Lys Val Met Ser  Leu Gly Pro
    1010                 1015                1020

Cys Ser  Ala Ser Cys Gly Leu  Gly Thr Ala Arg Arg  Ser Val Ala
    1025                 1030                1035

Cys Val  Gln Leu Asp Gln Gly  Gln Asp Val Glu Val  Asp Glu Ala
    1040                 1045                1050

Ala Cys  Ala Ala Leu Val Arg  Pro Glu Ala Ser Val  Pro Cys Leu
    1055                 1060                1065

Ile Ala  Asp Cys Thr Tyr Arg  Trp His Val Gly Thr  Trp Met Glu
    1070                 1075                1080

Cys Ser  Val Ser Cys Gly Asp  Gly Ile Gln Arg Arg  Arg Asp Thr
    1085                 1090                1095

Cys Leu  Gly Pro Gln Ala Gln  Ala Pro Val Pro Ala  Asp Phe Cys
    1100                 1105                1110

Gln His  Leu Pro Lys Pro Val  Thr Val Arg Gly Cys  Trp Ala Gly
    1115                 1120                1125

Pro Cys  Val Gly Gln Gly Thr  Pro Ser Leu Val Pro  His Glu Glu
    1130                 1135                1140

Ala Ala  Ala Pro Gly Arg Thr  Thr Ala Thr Pro Ala  Gly Ala Ser
    1145                 1150                1155

Leu Glu  Trp Ser Gln Ala Arg  Gly Leu Leu Phe Ser  Pro Ala Pro
    1160                 1165                1170

Gln Pro  Arg Arg Leu Leu Pro  Gly Pro Gln Glu Asn  Ser Val Gln
    1175                 1180                1185

Ser Ser  Ala Cys Gly Arg Gln  His Leu Glu Pro Thr  Gly Thr Ile
    1190                 1195                1200

Asp Met  Arg Gly Pro Gly Gln  Ala Asp Cys Ala Val  Ala Ile Gly
    1205                 1210                1215

Arg Pro  Leu Gly Glu Val Val  Thr Leu Arg Val Leu  Glu Ser Ser
    1220                 1225                1230

Leu Asn  Cys Ser Ala Gly Asp  Met Leu Leu Leu Trp  Gly Arg Leu
    1235                 1240                1245

Thr Trp  Arg Lys Met Cys Arg  Lys Leu Leu Asp Met  Thr Phe Ser
    1250                 1255                1260

Ser Lys  Thr Asn Thr Leu Val  Val Arg Gln Arg Cys  Gly Arg Pro
    1265                 1270                1275

Gly Gly  Gly Val Leu Leu Arg  Tyr Gly Ser Gln Leu  Ala Pro Glu
    1280                 1285                1290

Thr Phe  Tyr Arg Glu Cys Asp  Met Gln Leu Phe Gly  Pro Trp Gly
    1295                 1300                1305

Glu Ile  Val Ser Pro Ser Leu  Ser Pro Ala Thr Ser  Asn Ala Gly
    1310                 1315                1320
```

Gly Cys Arg Leu Phe Ile Asn Val Ala Pro His Ala Arg Ile Ala
1325 1330 1335

Ile His Ala Leu Ala Thr Asn Met Gly Ala Gly Thr Glu Gly Ala
1340 1345 1350

Asn Ala Ser Tyr Ile Leu Ile Arg Asp Thr His Ser Leu Arg Thr
1355 1360 1365

Thr Ala Phe His Gly Gln Gln Val Leu Tyr Trp Glu Ser Glu Ser
1370 1375 1380

Ser Gln Ala Glu Met Glu Phe Ser Glu Gly Phe Leu Lys Ala Gln
1385 1390 1395

Ala Ser Leu Arg Gly Gln Tyr Trp Thr Leu Gln Ser Trp Val Pro
1400 1405 1410

Glu Met Gln Asp Pro Gln Ser Trp Lys Gly Lys Glu Gly Thr
1415 1420 1425

<210> SEQ ID NO 6
<211> LENGTH: 685
<212> TYPE: PRT
<213> ORGANISM: Artificial Sequence
<220> FEATURE:
<223> OTHER INFORMATION: Synthetic

<400> SEQUENCE: 6

Met His Gln Arg His Pro Arg Ala Arg Cys Pro Pro Leu Cys Val Ala
1 5 10 15

Gly Ile Leu Ala Cys Gly Phe Leu Leu Gly Cys Trp Gly Pro Ser His
20 25 30

Phe Gln Gln Ser Cys Leu Gln Ala Leu Glu Pro Gln Ala Val Ser Ser
35 40 45

Tyr Leu Ser Pro Gly Ala Pro Leu Lys Gly Arg Pro Pro Ser Pro Gly
50 55 60

Phe Gln Arg Gln Arg Gln Arg Gln Arg Arg Ala Ala Gly Gly Ile Leu
65 70 75 80

His Leu Glu Leu Leu Val Ala Val Gly Pro Asp Val Phe Gln Ala His
85 90 95

Gln Glu Asp Thr Glu Arg Tyr Val Leu Thr Asn Leu Asn Ile Gly Ala
100 105 110

Glu Leu Leu Arg Asp Pro Ser Leu Gly Ala Gln Phe Arg Val His Leu
115 120 125

Val Lys Met Val Ile Leu Thr Glu Pro Glu Gly Ala Pro Asn Ile Thr
130 135 140

Ala Asn Leu Thr Ser Ser Leu Leu Ser Val Cys Gly Trp Ser Gln Thr
145 150 155 160

Ile Asn Pro Glu Asp Asp Thr Asp Pro Gly His Ala Asp Leu Val Leu
165 170 175

Tyr Ile Thr Arg Phe Asp Leu Glu Leu Pro Asp Gly Asn Arg Gln Val
180 185 190

Arg Gly Val Thr Gln Leu Gly Gly Ala Cys Ser Pro Thr Trp Ser Cys
195 200 205

Leu Ile Thr Glu Asp Thr Gly Phe Asp Leu Gly Val Thr Ile Ala His
210 215 220

Glu Ile Gly His Ser Phe Gly Leu Glu His Asp Gly Ala Pro Gly Ser
225 230 235 240

Gly Cys Gly Pro Ser Gly His Val Met Ala Ser Asp Gly Ala Ala Pro
245 250 255

```
Arg Ala Gly Leu Ala Trp Ser Pro Cys Ser Arg Arg Gln Leu Leu Ser
            260                 265                 270

Leu Leu Ser Ala Gly Arg Ala Arg Cys Val Trp Asp Pro Pro Arg Pro
        275                 280                 285

Gln Pro Gly Ser Ala Gly His Pro Pro Asp Ala Gln Pro Gly Leu Tyr
    290                 295                 300

Tyr Ser Ala Asn Glu Gln Cys Arg Val Ala Phe Gly Pro Lys Ala Val
305                 310                 315                 320

Ala Cys Thr Phe Ala Arg Glu His Leu Asp Met Cys Gln Ala Leu Ser
                325                 330                 335

Cys His Thr Asp Pro Leu Asp Gln Ser Ser Cys Ser Arg Leu Leu Val
            340                 345                 350

Pro Leu Leu Asp Gly Thr Glu Cys Gly Val Glu Lys Trp Cys Ser Lys
        355                 360                 365

Gly Arg Cys Arg Ser Leu Val Glu Leu Thr Pro Ile Ala Ala Val His
    370                 375                 380

Gly Arg Trp Ser Ser Trp Gly Pro Arg Ser Pro Cys Ser Arg Ser Cys
385                 390                 395                 400

Gly Gly Gly Val Val Thr Arg Arg Arg Gln Cys Asn Asn Pro Arg Pro
                405                 410                 415

Ala Phe Gly Gly Arg Ala Cys Val Gly Ala Asp Leu Gln Ala Glu Met
            420                 425                 430

Cys Asn Thr Gln Ala Cys Glu Lys Thr Gln Leu Glu Phe Met Ser Gln
        435                 440                 445

Gln Cys Ala Arg Thr Asp Gly Gln Pro Leu Arg Ser Ser Pro Gly Gly
    450                 455                 460

Ala Ser Phe Tyr His Trp Gly Ala Ala Val Pro His Ser Gln Gly Asp
465                 470                 475                 480

Ala Leu Cys Arg His Met Cys Arg Ala Ile Gly Glu Ser Phe Ile Met
                485                 490                 495

Lys Arg Gly Asp Ser Phe Leu Asp Gly Thr Arg Cys Met Pro Ser Gly
            500                 505                 510

Pro Arg Glu Asp Gly Thr Leu Ser Leu Cys Val Ser Gly Ser Cys Arg
        515                 520                 525

Thr Phe Gly Cys Asp Gly Arg Met Asp Ser Gln Gln Val Trp Asp Arg
    530                 535                 540

Cys Gln Val Cys Gly Gly Asp Asn Ser Thr Cys Ser Pro Arg Lys Gly
545                 550                 555                 560

Ser Phe Thr Ala Gly Arg Ala Arg Glu Tyr Val Thr Phe Leu Thr Val
                565                 570                 575

Thr Pro Asn Leu Thr Ser Val Tyr Ile Ala Asn His Arg Pro Leu Phe
            580                 585                 590

Thr His Leu Ala Val Arg Ile Gly Gly Arg Tyr Val Val Ala Gly Lys
        595                 600                 605

Met Ser Ile Ser Pro Asn Thr Thr Tyr Pro Ser Leu Leu Glu Asp Gly
    610                 615                 620

Arg Val Glu Tyr Arg Val Ala Leu Thr Glu Asp Arg Leu Pro Arg Leu
625                 630                 635                 640

Glu Glu Ile Arg Ile Trp Gly Pro Leu Gln Glu Asp Ala Asp Ile Gln
                645                 650                 655

Val Tyr Arg Arg Tyr Gly Glu Glu Tyr Gly Asn Leu Thr Arg Pro Asp
            660                 665                 670

Ile Thr Phe Thr Tyr Phe Gln Pro Lys Pro Arg Gln Ala
```

675 680 685

<210> SEQ ID NO 7
<211> LENGTH: 719
<212> TYPE: PRT
<213> ORGANISM: Artificial Sequence
<220> FEATURE:
<223> OTHER INFORMATION: Synthetic

<400> SEQUENCE: 7

Met His Gln Arg His Pro Arg Ala Arg Cys Pro Pro Leu Cys Val Ala
1 5 10 15

Gly Ile Leu Ala Cys Gly Phe Leu Leu Gly Cys Trp Gly Pro Ser His
20 25 30

Phe Gln Gln Ser Cys Leu Gln Ala Leu Glu Pro Gln Ala Val Ser Ser
35 40 45

Tyr Leu Ser Pro Gly Ala Pro Leu Lys Gly Arg Pro Pro Ser Pro Gly
50 55 60

Phe Gln Arg Gln Arg Gln Arg Gln Arg Arg Ala Ala Gly Gly Ile Leu
65 70 75 80

His Leu Glu Leu Leu Val Ala Val Gly Pro Asp Val Phe Gln Ala His
85 90 95

Gln Glu Asp Thr Glu Arg Tyr Val Leu Thr Asn Leu Asn Ile Gly Ala
100 105 110

Glu Leu Leu Arg Asp Pro Ser Leu Gly Ala Gln Phe Arg Val His Leu
115 120 125

Val Lys Met Val Ile Leu Thr Glu Pro Glu Gly Ala Pro Asn Ile Thr
130 135 140

Ala Asn Leu Thr Ser Ser Leu Leu Ser Val Cys Gly Trp Ser Gln Thr
145 150 155 160

Ile Asn Pro Glu Asp Asp Thr Asp Pro Gly His Ala Asp Leu Val Leu
165 170 175

Tyr Ile Thr Arg Phe Asp Leu Glu Leu Pro Asp Gly Asn Arg Gln Val
180 185 190

Arg Gly Val Thr Gln Leu Gly Gly Ala Cys Ser Pro Thr Trp Ser Cys
195 200 205

Leu Ile Thr Glu Asp Thr Gly Phe Asp Leu Gly Val Thr Ile Ala His
210 215 220

Glu Ile Gly His Ser Phe Gly Leu Glu His Asp Gly Ala Pro Gly Ser
225 230 235 240

Gly Cys Gly Pro Ser Gly His Val Met Ala Ser Asp Gly Ala Ala Pro
245 250 255

Arg Ala Gly Leu Ala Trp Ser Pro Cys Ser Arg Arg Gln Leu Leu Ser
260 265 270

Leu Leu Ser Ala Gly Arg Ala Arg Cys Val Trp Asp Pro Pro Arg Pro
275 280 285

Gln Pro Gly Ser Ala Gly His Pro Pro Asp Ala Gln Pro Gly Leu Tyr
290 295 300

Tyr Ser Ala Asn Glu Gln Cys Arg Val Ala Phe Gly Pro Lys Ala Val
305 310 315 320

Ala Cys Thr Phe Ala Arg Glu His Leu Asp Met Cys Gln Ala Leu Ser
325 330 335

Cys His Thr Asp Pro Leu Asp Gln Ser Ser Cys Ser Arg Leu Leu Val
340 345 350

Pro Leu Leu Asp Gly Thr Glu Cys Gly Val Glu Lys Trp Cys Ser Lys

```
        355                 360                 365

Gly Arg Cys Arg Ser Leu Val Glu Leu Thr Pro Ile Ala Ala Val His
    370                 375                 380

Gly Arg Trp Ser Ser Trp Gly Pro Arg Ser Pro Cys Ser Arg Ser Cys
385                 390                 395                 400

Gly Gly Gly Val Val Thr Arg Arg Arg Gln Cys Asn Asn Pro Arg Pro
                405                 410                 415

Ala Phe Gly Gly Arg Ala Cys Val Gly Ala Asp Leu Gln Ala Glu Met
            420                 425                 430

Cys Asn Thr Gln Ala Cys Glu Lys Thr Gln Leu Glu Phe Met Ser Gln
        435                 440                 445

Gln Cys Ala Arg Thr Asp Gly Gln Pro Leu Arg Ser Ser Pro Gly Gly
    450                 455                 460

Ala Ser Phe Tyr His Trp Gly Ala Ala Val Pro His Ser Gln Gly Asp
465                 470                 475                 480

Ala Leu Cys Arg His Met Cys Arg Ala Ile Gly Glu Ser Phe Ile Met
                485                 490                 495

Lys Arg Gly Asp Ser Phe Leu Asp Gly Thr Arg Cys Met Pro Ser Gly
            500                 505                 510

Pro Arg Glu Asp Gly Thr Leu Ser Leu Cys Val Ser Gly Ser Cys Arg
        515                 520                 525

Thr Phe Gly Cys Asp Gly Arg Met Asp Ser Gln Gln Val Trp Asp Arg
    530                 535                 540

Cys Gln Val Cys Gly Gly Asp Asn Ser Thr Cys Ser Pro Arg Lys Gly
545                 550                 555                 560

Ser Phe Thr Ala Gly Arg Ala Arg Glu Tyr Val Thr Phe Leu Thr Val
                565                 570                 575

Thr Pro Asn Leu Thr Ser Val Tyr Ile Ala Asn His Arg Pro Leu Phe
            580                 585                 590

Thr His Leu Ala Val Arg Ile Gly Gly Arg Tyr Val Val Ala Gly Lys
        595                 600                 605

Met Ser Ile Ser Pro Asn Thr Thr Tyr Pro Ser Leu Leu Glu Asp Gly
    610                 615                 620

Arg Val Glu Tyr Arg Val Ala Leu Thr Glu Asp Arg Leu Pro Arg Leu
625                 630                 635                 640

Glu Glu Ile Arg Ile Trp Gly Pro Leu Gln Glu Asp Ala Asp Ile Gln
                645                 650                 655

Val Tyr Arg Arg Tyr Gly Glu Glu Tyr Gly Asn Leu Thr Arg Pro Asp
            660                 665                 670

Ile Thr Phe Thr Tyr Phe Gln Pro Lys Pro Arg Gln Ala Lys Gly Glu
        675                 680                 685

Leu Gly Thr Glu Leu Gly Ser Glu Gly Lys Pro Ile Pro Asn Pro Leu
    690                 695                 700

Leu Gly Leu Asp Ser Thr Arg Thr Gly His His His His His His
705                 710                 715
```

<210> SEQ ID NO 8
<211> LENGTH: 29
<212> TYPE: PRT
<213> ORGANISM: Artificial Sequence
<220> FEATURE:
<223> OTHER INFORMATION: Synthetic

<400> SEQUENCE: 8

```
Met His Gln Arg His Pro Arg Ala Arg Cys Pro Pro Leu Cys Val Ala
```

-continued

```
1               5                  10                 15

Gly Ile Leu Ala Cys Gly Phe Leu Leu Gly Cys Trp Gly
            20                  25


<210> SEQ ID NO 9
<211> LENGTH: 11
<212> TYPE: PRT
<213> ORGANISM: Artificial Sequence
<220> FEATURE:
<223> OTHER INFORMATION: Synthetic

<400> SEQUENCE: 9

Lys Gly Glu Leu Gly Thr Glu Leu Gly Ser Glu
1               5                  10


<210> SEQ ID NO 10
<211> LENGTH: 14
<212> TYPE: PRT
<213> ORGANISM: Artificial Sequence
<220> FEATURE:
<223> OTHER INFORMATION: Synthetic

<400> SEQUENCE: 10

Gly Lys Pro Ile Pro Asn Pro Leu Leu Gly Leu Asp Ser Thr
1               5                  10


<210> SEQ ID NO 11
<211> LENGTH: 6
<212> TYPE: PRT
<213> ORGANISM: Artificial Sequence
<220> FEATURE:
<223> OTHER INFORMATION: Synthetic

<400> SEQUENCE: 11

His His His His His His
1               5
```

TRUNCATED MODIFIED RECOMBINANT ADAMTS13 AND USES THEREOF

RELATED APPLICATIONS

This application is a national stage filing under 35 U.S.C. 371 of international patent application number PCT/US2021/057013, filed Oct. 28, 2021, which claims the benefit under 35 U.S.C. § 119(e) to U.S. Provisional Application No. 63/106,699, filed Oct. 28, 2020, both entitled "TRUNCATED MODIFIED RECOMBINANT ADAMTS13 AND USES THEREOF," the entire contents of each of which are incorporated herein by reference.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Apr. 25, 2023, is named C123370185US01-SEQ-MOD and is 47,158 bytes in size.

BACKGROUND

ADAMTS13 (a disintegrin and metalloproteinase with a thrombospondin type 1 motif, member 13), also known as von Willebrand factor-cleaving protease (VWFCP), is a zinc-containing metalloprotease enzyme that cleaves von Willebrand factor (VWF), a large protein involved in blood clotting. It is secreted into the blood and degrades large VWF multimers, decreasing their unwanted activity. Human recombinant ADAMTS13 is currently being developed for the treatment of thrombotic thrombocytopenic purpura (TTP) (*N Engl J Med.* 2019 Oct. 24; 381(17): 1653-1662) and sickle cell disease (SCD). Its current formulation is dosed by intravenous administration, which results in limited half-life, and repeated administration is required for long term replacement/supplementation of ADAMTS13 plasmatic activity. Therefore, there is a need for improved forms and/or formulations of ADAMTS13, particularly for patients requiring supplementation and frequent administration of intravenous ADAMTS13.

SUMMARY

The present disclosure stems from the recognition that formulation of a truncated modified human recombinant ADAMTS13 (mrADAMTS13) having enhanced activity into a drug delivery composition (e.g., encapsulation in a synthetic microparticle) may have extended delivery via different routes of administration. Application of extended release mrADAMTS13 protein activity to treat diseases that involve decreased plasmatic ADAMTS13 activity, and thrombotic diseases such as diseases involving abnormal thrombus formation (e.g., mediated by von Willebrand Factor (VWF)) are of significant clinical interest.

In one aspect, provided herein are polypeptides comprising sequences having at least 90% amino acid sequence identity to SEQ ID NO: 7 (mrADAMTS13), wherein the polypeptides are not SEQ ID NO: 5 (ADAMTS13).

In another aspect, provided herein are nucleic acid molecules comprising nucleotide sequences encoding the polypeptides.

In another aspect, provided herein are vectors comprising the nucleic acid molecules.

In another aspect, provided herein are cells comprising the polypeptides, nucleic acid molecules, or vectors.

In another aspect, provided herein are methods of producing the polypeptides, the methods comprising culturing cells in a culturing media, under conditions that allow the polypeptides to express.

In another aspect, provided herein are drug delivery compositions comprising biocompatible materials and the polypeptides. In certain embodiments, the drug delivery compositions comprise microparticles encapsulating the polypeptides.

In another aspect, provided herein are pharmaceutical compositions comprising the polypeptides and a pharmaceutically acceptable carrier.

In another aspect, provided herein are pharmaceutical compositions comprising the drug delivery compositions and optionally a pharmaceutically acceptable carrier.

In another aspect, disclosed herein are methods of preparing a microparticle comprising the polypeptide, the methods comprising: emulsifying the polypeptide in a solution containing a polymer to provide a first emulsification; emulsifying the first emulsification in a solution containing an emulsifying agent to provide a second emulsification; evaporating the solvent of the second emulsification; and isolating the microparticle.

In another aspect, disclosed herein are methods of treating or preventing a thrombotic disease or condition, the methods comprising administering to a subject in need thereof a therapeutically effective amount of the polypeptide, the drug delivery composition, or a pharmaceutical composition disclosed herein.

In another aspect, disclosed herein are methods of cleaving von Willebrand factor (VWF), the method comprising contacting the polypeptide, the drug delivery composition, or a pharmaceutical composition described herein with VWF.

In another aspect, disclosed herein are kits comprising the polypeptide, the drug delivery composition, or a pharmaceutical composition described herein; and instructions for use.

The summary above is meant to illustrate, in a non-limiting manner, some of the embodiments, advantages, features, and uses of the technology disclosed herein. Other embodiments, advantages, features, and uses of the technology disclosed herein will be apparent from the Detailed Description, the Drawings, the Examples, and the Claims.

DETAILED DESCRIPTION OF CERTAIN EMBODIMENTS

Figure 1:
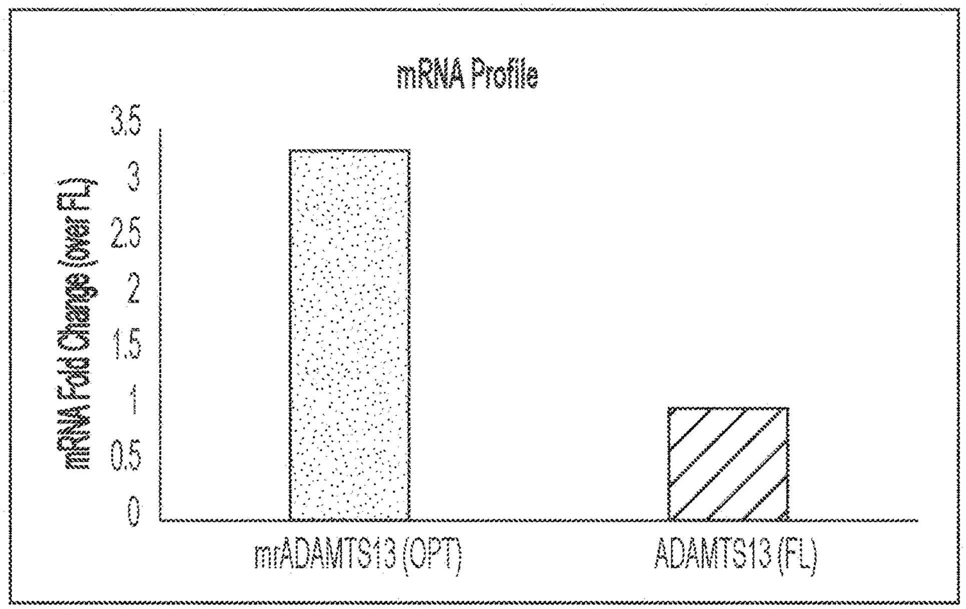
FIG. 1 is a plot of the mRNA profiles of mrADAMTS13 (OPT) (SEQ ID NO: 7) and full length wild-type ADAMTS13 (FL) (SEQ ID NO: 5).

Disclosed herein are polypeptides, nucleic acid molecules that encode the polypeptides, drug delivery compositions that comprise the polypeptides, pharmaceutical compositions that comprise the polypeptides, and methods of treating thrombotic disease with the polypeptides and compositions.

The polypeptides are a modified recombinant truncation of ADAMTS13 (e.g., mrADAMTS13) that possess enhanced expression and ADAMTS13 specific VWF cleaving activity. mrADAMTS13 is readily expressed from HEK293T cells with a molecular weight of ~80 kDa when secreted into cell culture media. mrADAMTS13 can be encapsulated into a drug delivery composition (e.g., a PLGA-microparticle). The composition releases intact ADAMTS13 activity for a period of at least 120 hours, demonstrating that mrADAMTS13 is suitable for a controlled extended release drug delivery system.

The disclosed drug delivery compositions and pharmaceutical compositions may deliver measurable ADAMTS13 activity over prolonged periods of time in contrast to the formulation of ADAMTS13 currently being developed in clinic trials. ADAMTS13 is administered intravenously and requires frequent administration. However, the compositions disclosed herein provide extended-release, maintaining stable plasmatic concentration and decreasing the need for more frequent and repeated administration compared to intra-venous ADAMTS13 administration. These features of mrADAMTS13 and the presently disclosed compositions also serve to extend the anti-thrombotic properties of ADAMTS13 to additional applications such as thrombotic diseases for example, diseases involving abnormal thrombus formation (e.g., mediated by von Willebrand Factor (VWF)).

The present disclosure recognizes that mrADAMTS13 contains the minimum molecular elements demonstrated to have effective ADAMTS13-VWF cleavage activity. mrADAMTS13 contains a modified DNA sequence that provides enhanced cellular expression and ADAMTS13 activity. This recombinant truncation offers the technical advantage of a reduced molecular weight, offering the possibility of encapsulation into a synthetic drug delivery system designed for extended release with preservation of the enzymatic properties observed with the full-length wild type sequence. Specifically, a PLGA encapsulation of mrADAMTS13 offers the advantage of extended release of precise plasmatic concentrations of a given dose over periods of time extending beyond the half-life of the current recombinant ADAMTS13 product currently under development. The disclosed drug delivery and pharmaceutical compositions, such as PLGA-mrADAMTS13, are designed to deliver ADAMTS13 activity via a variety of routes of administration (e.g., subcutaneous, intramuscular, intravenous, intraperitoneal) as a single dose or by continuous infusion. This preparation has the potential advantage of requiring significantly less frequency of administration and delivery of precise and controlled concentrations/activity of ADAMTS13, thus considerably improving quality of life for the patients and extending to chronic use in patients requiring long term supplementation of ADAMTS13 activity.

Accordingly, provided herein is a polypeptide comprising a sequence having at least 90% amino acid sequence identity to SEQ ID NO: 7 (mrADAMTS13), wherein the polypeptide is not SEQ ID NO: 5 (ADAMTS13). In certain embodiments, the polypeptide has at least 91%, 92%, 93%, 94%, 95%, 96%, 97%, 98%, 99%, or 99.5% amino acid sequence identity to SEQ ID NO: 7. In certain embodiments, the polypeptide comprises SEQ ID NO: 7. In certain embodiments, the polypeptide consists essentially of SEQ ID NO: 7. In certain embodiments, the polypeptide consists of SEQ ID NO: 7. In certain embodiments, the polypeptide is a recombinant protein.

A "protein," "peptide," or "polypeptide" comprises a polymer of amino acid residues linked together by peptide bonds. The term refers to proteins, polypeptides, and peptides of any size, structure, or function. Typically, a protein will be at least three amino acids long. A protein may refer to an individual protein or a collection of proteins. Inventive proteins preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a protein may be modified, for example, by the addition of a chemical entity such as a carbohydrate group, a hydroxyl group, a phosphate group, a farnesyl group, an isofarnesyl group, a fatty acid group, a linker for conjugation or functionalization, or other modification. A protein may also be a single molecule or may be a multi-molecular complex. A protein may be a fragment of a naturally occurring protein or peptide. A protein may be naturally occurring, recombinant, synthetic, or any combination of these.

In certain embodiments, the polypeptide further comprises a signal peptide. For example, in certain embodiments, the signal peptide is present at the N-terminus of mrADAMTS13. A "signal peptide" refers to a short peptide (e.g., 16-30 amino acids long) present at the N-terminus of a large number of newly synthesized proteins that are destined towards the secretory pathway. Signal peptides are typically needed for the translocation across the membrane on the secretory pathway and thus universally control the entry of most proteins both in eukaryotes and prokaryotes to the secretory pathway. Signal peptides generally include three regions: an N-terminal region of differing length, which usually comprises positively charged amino acids; a hydrophobic region; and a short carboxy-terminal peptide region. In eukaryotes, the signal peptide of a nascent precursor protein (pre-protein) directs the ribosome to the rough endoplasmic reticulum (ER) membrane and initiates the transport of the growing peptide chain across it. The signal peptide is not responsible for the final destination of the mature protein, however. Secretory proteins devoid of further address tags in their sequence are by default secreted to the external environment. Signal peptides are cleaved from precursor proteins by an endoplasmic reticulum (ER)-resident signal peptidase or they remain uncleaved and function as a membrane anchor.

A signal peptide may have a length of 15-60 amino acids. For example, a signal peptide may have a length of 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 amino acids. In certain embodiments, a signal peptide may have a length of 20-60, 25-60, 30-60, 35- 60, 40-60, 45- 60, 50-60, 55-60, 15-55, 20-55, 25-55, 30-55, 35-55, 40-55, 45-55, 50-55, 15-50, 20-50, 25-50, 30-50, 35-50, 40-50, 45-50, 15-45, 20-45, 25-45, 30-45, 35-45, 40-45, 15-40, 20-40, 25-40, 30-40, 35-40, 15-35, 20-35, 25-35, 30-35, 15-30, 20-30, 25-30, 15-25, 20-25, or 15-20 amino acids.

In certain embodiments, the polypeptide of the present disclosure contains a signal peptide at the either the N- or C-terminus to facilitate secretion of the polypeptide. In certain embodiments, the signal peptide is at the N-terminus of the polypeptide. In certain embodiments, the signal peptide comprises the amino acid sequence of

```
                              (SEQ ID NO: 8)
MHQRHPRARCPPLCVAGILACGFLLGCWG.
```

The "percent identity" of two amino acid sequences is determined using the algorithm of Karlin and Altschul Proc. Natl. Acad. Sci. USA 87: 2264-68, 1990, modified as in Karlin and Altschul Proc. Natl. Acad. Sci. USA 90: 5873-77, 1993. Such an algorithm is incorporated into the NBLAST and XBLAST programs (version 2.0) of Altschul, et al. J. Mol. Biol. 215: 403-10, 1990. BLAST protein searches can be performed with the XBLAST program, score=50, wordlength=3 to obtain amino acid sequences homologous to the protein molecules of interest. Where gaps exist between two sequences, Gapped BLAST can be utilized as described in Altschul et al., Nucleic Acids Res. 25(17): 3389-3402, 1997. When utilizing BLAST and Gapped BLAST programs, the default parameters of the respective programs (e.g., XBLAST and NB LAST) can be used.

Amino acid substitution can be achieved during chemical synthesis of the polypeptide by adding the desired substitute amino acid at the appropriate sequence in the synthesis process. Alternatively, molecular biology methods can be used. Non-conservative substitutions are also encompassed to the extent that they substantially retain the activities of those peptides described herein.

In certain embodiments, an amino acid substituted polypeptide will substantially retain the activity of the non-substituted polypeptide. By "substantially retain" means one or more activity of the variant is at least 50% compared to the activity of the original polypeptide in a similar assay, under similar conditions. In certain embodiments, the activity is at least 60%, at least 70%, at least 80%, at least 90%, at least 95%, at least 99%, at least 100%, at least 2-fold, at least 5-fold, at least 10-fold, at least 100-fold or higher activity compared to the original polypeptide.

In certain embodiments, the polypeptide comprises one or more linkers which fuse a polypeptide (e.g., wild type or variant) to one or more tags. A "linker" refers to a chemical group or a molecule linking two molecules or moieties. Typically, the linker is positioned between, or flanked by, two groups, molecules, domains, or other moieties and connected to each one via a covalent bond, thus connecting the two. The linker may be as simple as a covalent bond, or it may be a polymeric linker many atoms in length. In certain embodiments, the linker is a polypeptide or based on amino acids. In certain embodiments, the linker is not peptide-like. In certain embodiments, the linker is a covalent bond (e.g., a carbon-carbon bond, disulfide bond, carbon-heteroatom bond, etc.). In certain embodiments, the linker is a carbon-nitrogen bond of an amide linkage. In certain embodiments, the linker is a cyclic or acyclic, substituted or unsubstituted, branched or unbranched aliphatic or heteroaliphatic linker. In certain embodiments, the linker is polymeric (e.g., polyethylene, polyethylene glycol, polyamide, polyester, etc.). In certain embodiments, the linker comprises a monomer, dimer, or polymer of aminoalkanoic acid. In certain embodiments, the linker comprises an aminoalkanoic acid (e.g., glycine, ethanoic acid, alanine, beta-alanine, 3-aminopropanoic acid, 4-aminobutanoic acid, 5-pentanoic acid, etc.). In certain embodiments, the linker comprises a monomer, dimer, or polymer of aminohexanoic acid (Ahx). In certain embodiments, the linker is based on a carbocyclic moiety (e.g., cyclopentane, cyclohexane). In other embodiments, the linker comprises a polyethylene glycol moiety (PEG). In other embodiments, the linker comprises amino acids. In certain embodiments, the linker comprises a peptide. In certain embodiments, the linker comprises an aryl or heteroaryl moiety. In certain embodiments, the linker comprises a phenyl ring. The linker may include functionalized moieties to facilitate attachment of a nucleophile (e.g., thiol, amino) from the peptide to the linker. Any electrophile may be used as part of the linker. Exemplary electrophiles include, but are not limited to, activated esters, activated amides, Michael acceptors, alkyl halides, aryl halides, acyl halides, and isothiocyanates.

In certain embodiments, the linker is an amino acid or a plurality of amino acids (e.g., a peptide or protein). In certain embodiments, the linker is a bond (e.g., a covalent bond), an organic molecule, group, polymer, or chemical moiety. In certain embodiments, the linker is 1-100 amino acids in length, for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 30-35, 35-40, 40-45, 45-50, 50-60, 60-70, 70-80, 80-90, 90-100, 100-110, 110-120, 120-130, 130-140, 140-150, or 150-200 amino acids in length. Longer or shorter linkers are also contemplated.

In certain embodiments, the linker comprises the amino acid sequence KGELGTELGSE (SEQ ID NO: 9). In certain embodiments, the linker comprises the amino acid sequence RTG.

In certain embodiments, the linker links a V5 Tag to a polypeptide (e.g., wild type or variant). In some embodiment, the V5 Tag comprises the amino acid sequence GKPIPNPLLGLDST (SEQ ID NO: 10). In certain embodiments, the linker links a His Tag to a polypeptide (e.g., wild type or variant). In some embodiment, the His Tag comprises the amino acid sequence HHHHHH (SEQ ID NO: 11).

In certain embodiments, the polypeptide described herein comprises a modification. When the polypeptide is referred to herein, it encompasses all its variants and derivatives. Polypeptides comprising modifications have additional features other than amino acid contents. As used herein, a "modification" or "derivative" of a protein or polypeptide produces a modified or derivatized polypeptide, which is a form of a given peptide that is chemically modified relative to the reference peptide, the modification including, but not limited to, oligomerization or polymerization, modifications of amino acid residues or peptide backbone, cross-linking, cyclization, conjugation, PEGylation, glycosylation, acetylation, phosphorylation, acylation, carboxylation, lipidation, thioglycolic acid amidation, alkylation, methylation, polyglycylation, glycosylation, polysialylation, adenylylation, PEGylation, fusion to additional heterologous amino acid sequences, or other modifications that substantially alter the stability, solubility, or other properties of the peptide while substantially retaining the activity of the polypeptides described herein. It is to be understood that the polypeptide comprising such modifications, are cross-linked, cyclized, conjugated, acylated, carboxylated, lipidated, acetylated, thioglycolic acid amidated, alkylated, methylated, polyglycylated, glycosylated, polysialylated, phosphorylated, adenylylated, PEGylated, or combination thereof. In certain embodiments, the modified polypeptide of the present disclosure may contain non-amino acid elements, such as polyethylene glycols, lipids, poly- or monosaccharide, and phosphates. The polypeptide of the present disclosure may comprise the modifications disclosed herein at the C-terminus (e.g., C-terminal amidation), N-terminus (e.g., N-terminal acetylation). Terminal modifications are useful, and are well known, to reduce susceptibility to proteinase digestion, and therefore serve to prolong half-life of the polypeptides in solutions, particularly biological fluids where proteases may be present. In certain embodiments, the polypeptides described herein are further modified within the sequence, such as, modification by terminal-$NH_2$ acylation, e.g., acetylation, or thioglycolic acid amidation, by terminal-carboxylamidation, e.g., with ammonia, methylamine, and the like terminal modifications.

Terminal modifications are useful, to reduce susceptibility by proteinase digestion, and therefore can serve to prolong half-life of the polypeptides in solution, particularly in biological fluids where proteases may be present. Amino terminus modifications include methylation (e.g., —$NHCH_3$ or —$N(CH_3)_2$), acetylation (e.g., with acetic acid or a halogenated derivative thereof such as a-chloroacetic acid, a-bromoacetic acid, or a-iodoacetic acid), adding a benzyloxycarbonyl (Cbz) group, or blocking the amino terminus with any blocking group containing a carboxylate functionality defined by RCOO— or sulfonyl functionality defined by R—$SO_2$—, where R is selected from the group consisting of alkyl, aryl, heteroaryl, alkyl aryl, and the like, and similar groups. One can also incorporate a desamino acid at the N-terminus (so that there is no N-terminal amino group) to decrease susceptibility to proteases or to restrict the conformation of the polypeptide. In certain embodiments, the N-terminus is acetylated with acetic acid or acetic anhydride.

Carboxy terminus modifications include replacing the free acid with a carboxamide group or forming a cyclic lactam at the carboxy terminus to introduce structural constraints. One can also cyclize the peptides described herein, or incorporate a desamino or descarboxy residue at the termini of the peptide, so that there is no terminal amino or carboxyl group, to decrease susceptibility to proteases or to restrict the conformation of the peptide. Methods of circular peptide synthesis are known in the art, for example, in U.S. Patent Application No. 20090035814; Muralidharan and Muir, 2006, Nat Methods, 3: 429-38; and Lockless and Muir, 2009, Proc Natl Acad Sci U S A. Jun 18, Epub. C-terminal functional groups of the peptides described herein include amide, amide lower alkyl, amide di (lower alkyl), lower alkoxy, hydroxy, and carboxy, and the lower ester derivatives thereof, and the pharmaceutically acceptable salts thereof.

In certain embodiments, the polypeptides described herein are phosphorylated. One can also readily modify peptides by phosphorylation, and other methods (e.g., as described in Hruby, et al. (1990) Biochem J. 268: 249-262). In certain embodiments, one can also replace the naturally occurring side chains of the genetically encoded amino acids (or the stereoisomeric D amino acids) with other side chains, for instance with groups such as alkyl, lower ($C_{1-6}$) alkyl, cyclic 4-, 5-, 6-, to 7-membered alkyl, amide, amide lower alkyl amide di (lower alkyl), lower alkoxy, hydroxy, carboxy and the lower ester derivatives thereof, and with 4-, 5-, 6-, to 7-membered heterocycles. For example, proline analogues in which the ring size of the proline residue is changed from 5 members to 4, 6, or 7 members can be employed.

Cyclic groups can be saturated or unsaturated, and if unsaturated, can be aromatic or non-aromatic. Heterocyclic groups preferably contain one or more nitrogen, oxygen, and/or sulfur heteroatoms. Examples of such groups include the furazanyl, furyl, imidazolidinyl, imidazolyl, imidazolinyl, isothiazolyl, isoxazolyl, morpholinyl (e.g., morpholino), oxazolyl, piperazinyl (e.g., 1-piperazinyl), piperidyl (e.g., 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g., 1-pyrrolidinyl), pyrrolinyl, pyrrolyl, thiadiazolyl, thiazolyl, thienyl, thiomorpholinyl (e.g., thiomorpholino), and triazolyl groups. These heterocyclic groups can be substituted or unsubstituted. Where a group is substituted, the substituent can be alkyl, alkoxy, halogen, oxygen, or substituted or unsubstituted phenyl.

Other aspects of the present disclosure provide methods of producing the polypeptide. The polypeptide will generally be produced by expression from nucleic acids in appropriate cells (e.g., bacterial cell or eukaryotic cells) and isolated. To produce the polypeptide, nucleic acids encoding the polypeptide may be introduced to a cell. The cells may be cultured under conditions that allow the polypeptide to express from the nucleic acids encoding polypeptide. Polypeptides comprising a signal peptide can be secreted, e.g., into the culturing media and can subsequently be recovered. The polypeptide may be isolated using any methods of purifying a protein known in the art.

The terms "polynucleotide", "nucleotide sequence", "nucleic acid", "nucleic acid molecule", "nucleic acid sequence", and "oligonucleotide" refer to a series of nucleotide bases (also called "nucleotides") in DNA and RNA, and mean any chain of two or more nucleotides. The polynucleotides can be chimeric mixtures or derivatives or modified versions thereof, single-stranded or double-stranded. The oligonucleotide can be modified at the base moiety, sugar moiety, or phosphate backbone, for example, to improve stability of the molecule, its hybridization parameters, etc. The antisense oligonuculeotide may comprise a modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5- methoxyaminomethyl-2-thiouracil, beta-D-mannosylqueosine, 5'-methoxycarboxymethyluracil, 5-methoxyuracil, 2-methylthio-N6-isopentenyladenine, wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl) uracil, a thio-guanine, and 2,6-diaminopurine. A nucleotide sequence typically carries genetic information, including the information used by cellular machinery to make proteins and enzymes. These terms include double- or single-stranded genomic and cDNA, RNA, any synthetic and genetically manipulated polynucleotide, and both sense and antisense polynucleotides. This includes single- and double-stranded molecules, i.e., DNA-DNA, DNA-RNA and RNA-RNA hybrids, as well as "protein nucleic acids" (PNAs) formed by conjugating bases to an amino acid backbone. This also includes nucleic acids containing carbohydrate or lipids. Exemplary DNAs include single-stranded DNA (ssDNA), double-stranded DNA (dsDNA), plasmid DNA (pDNA), genomic DNA (gDNA), complementary DNA (cDNA), antisense DNA, chloroplast DNA (ctDNA or cpDNA), microsatellite DNA, mitochondrial DNA (mtDNA or mDNA), kinetoplast DNA (kDNA), provirus, lysogen, repetitive DNA, satellite DNA, and viral DNA. Exemplary RNAs include single-stranded RNA (ssRNA), double-stranded RNA (dsRNA), small interfering RNA (siRNA), messenger RNA (mRNA), precursor messenger RNA (pre-mRNA), small hairpin RNA or short hairpin RNA (shRNA), microRNA (miRNA), guide RNA (gRNA), transfer RNA (tRNA), antisense RNA (asRNA), heterogeneous nuclear RNA (hnRNA), coding RNA, non-coding RNA (ncRNA), long non-coding RNA (long ncRNA or lncRNA), satellite RNA, viral satellite RNA, signal recognition particle RNA, small cytoplasmic RNA, small nuclear RNA (snRNA), ribosomal RNA (rRNA), Piwi-interacting RNA (piRNA), polyinosinic acid, ribozyme, flexizyme, small nucleolar RNA (snoRNA), spliced leader RNA, viral RNA, and viral satellite RNA.

The nucleic acids encoding the polypeptide described herein may be obtained, and the nucleotide sequence of the nucleic acids determined, by any method known in the art. Non-limiting, exemplary nucleotide sequence encoding the polypeptide or variants described herein are provided, e.g., SEQ ID NOs: 1-4. One skilled in the art is able to identify the nucleotide sequence encoding the polypeptide from the amino acid sequence of the polypeptide. The nucleic acids encoding the polypeptide of the present disclosure, may be DNA or RNA, double-stranded or single stranded. In certain embodiments, the nucleotide sequence encoding the polypeptide may be codon optimized to adapt to different expression systems (e.g., for mammalian expression).

Accordingly, provided herein is a nucleic acid molecule comprising a nucleotide sequence encoding the polypeptide. In certain embodiments, the nucleotide sequence has at least 85%, 86%, 87%, 88%, 89%, 90%, 91%, 92%, 93%, 94%, 95%, 96%, 97%, 98%, 99%, or 99.5% sequence identity to the nucleotide sequence of SEQ ID NO: 3 or SEQ ID NO: 4. In certain embodiments, the nucleotide sequence comprises the nucleotide sequence of SEQ ID NO: 3 or SEQ ID NO: 4. In certain embodiments, the nucleotide sequence consists essentially of the nucleotide sequence of SEQ ID NO: 3 or SEQ ID NO: 4. In certain embodiments, the nucleotide sequence consists of the nucleotide sequence of SEQ ID NO: 3 or SEQ ID NO: 4.

In certain embodiments, the nucleotide sequence has at least 85%, 86%, 87%, 88%, 89%, 90%, 91%, 92%, 93%, 94%, 95%, 96%, 97%, 98%, 99%, or 99.5% sequence identity to the nucleotide sequence of SEQ ID NO: 3. In certain embodiments, the nucleotide sequence comprises the nucleotide sequence of SEQ ID NO: 3. In certain embodiments, the nucleotide sequence consists essentially of the nucleotide sequence of SEQ ID NO: 3. In certain embodiments, the nucleotide sequence consists of the nucleotide sequence of SEQ ID NO: 3.

In certain embodiments, the nucleotide sequence has at least 85%, 86%, 87%, 88%, 89%, 90%, 91%, 92%, 93%, 94%, 95%, 96%, 97%, 98%, 99%, or 99.5% sequence identity to the nucleotide sequence of SEQ ID NO: 4. In certain embodiments, the nucleotide sequence comprises the nucleotide sequence of SEQ ID NO: 4. In certain embodiments, the nucleotide sequence consists essentially of the nucleotide sequence of SEQ ID NO: 4. In certain embodiments, the nucleotide sequence consists of the nucleotide sequence of SEQ ID NO: 4.

Polynucleotides or nucleic acid molecules described herein may be synthesized by standard methods known in the art, e.g., by use of an automated DNA synthesizer (such as those that are commercially available from Biosearch, Applied Biosystems, etc.). As examples, phosphorothioate oligonucleotides may be synthesized by the method of Stein et al., Nucl. Acids Res., 16, 3209, (1988), methylphosphonate oligonucleotides can be prepared by use of controlled pore glass polymer supports (Sarin et al., Proc. Natl. Acad. Sci. U.S.A. 85, 7448-7451, (1988)). A number of methods have been developed for delivering antisense DNA or RNA to cells, e.g., antisense molecules can be injected directly into the tissue site, or modified antisense molecules, designed to target the desired cells (antisense linked to peptides or antibodies that specifically bind receptors or antigens expressed on the target cell surface) can be administered systemically. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines. However, it is often difficult to achieve intracellular concentrations of the antisense sufficient to suppress translation of endogenous mRNAs. Therefore, a preferred approach utilizes a recombinant DNA construct in which the antisense oligonucleotide is placed under the control of a strong promoter. The use of such a construct to transfect target cells in the patient will result in the transcription of sufficient amounts of single stranded RNAs that will form complementary base pairs with the endogenous target gene transcripts and thereby prevent translation of the target gene mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human, cells. Such promoters can be inducible or constitutive. Any type of plasmid, cosmid, yeast artificial chromosome, or viral vector can be used to prepare the recombinant DNA construct that can be introduced directly into the tissue site.

The polynucleotides or nucleic acid molecules may be flanked by natural regulatory (expression control) sequences or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like. The nucleic acids may also be modified by many means known in the art. Non-limiting examples of such modifications include methylation, “caps”, substitution of one or more of the naturally occurring nucleotides with an analog, and internucleotide modifications, such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radioisotopes, fluorescent molecules, isotopes (e.g., radioactive isotopes), biotin, and the like.

In certain embodiments, the nucleic acid is comprised within a vector, such as an expression vector. In certain embodiments, the vector comprises a promoter operably linked to the nucleic acid. In certain embodiments, the vector is a plasmid.

A variety of promoters can be used for expression of the polypeptides described herein, including, but not limited to, cytomegalovirus (CMV) intermediate early promoter, a viral LTR such as the Rous sarcoma virus LTR, HIV-LTR, HTLV-1 LTR, the simian virus 40 (SV40) early promoter, *E. coli* lac UV5 promoter, and the herpes simplex tk virus promoter.

Regulatable promoters can also be used. Such regulatable promoters include those using the lac repressor from *E. coli* as a transcription modulator to regulate transcription from lac operator-bearing mammalian cell promoters [Brown, M. et al., Cell, 49: 603-612 (1987)], those using the tetracycline repressor (tetR) [Gossen, M., and Bujard, H., Proc. Natl. Acad. Sci. USA 89: 5547-5551 (1992); Yao, F. et al., Human Gene Therapy, 9: 1939-1950 (1998); Shockelt, P., et al., Proc. Natl. Acad. Sci. USA, 92: 6522-6526 (1995)]. Other systems include FK506 dimer, VP16 or p65 using astradiol, RU486, diphenol murislerone, or rapamycin. Inducible systems are available from Invitrogen, Clontech and Ariad.

Regulatable promoters that include a repressor with the operon can be used. In one embodiment, the lac repressor from *Escherichia coli* can function as a transcriptional modulator to regulate transcription from lac operator-bearing mammalian cell promoters [M. Brown et al., Cell, 49: 603-612 (1987)]; Gossen and Bujard (1992); [M. Gossen et al., Natl. Acad. Sci. USA, 89: 5547-5551 (1992)] combined the tetracycline repressor (tetR) with the transcription activator (VP 16) to create a tetR-mammalian cell transcription activator fusion protein, tTa (tetR-VP 16), with the tet0-bearing minimal promoter derived from the human cytomegalovirus (hCMV) major immediate-early promoter to create a tetR-tet operator system to control gene expression in mammalian cells. In one embodiment, a tetracycline inducible switch is used (Yao et al., Human Gene Therapy; Gossen et al., Natl. Acad. Sci. USA, 89: 5547-5551 (1992); Shockett et al., Proc. Natl. Acad. Sci. USA, 92: 6522-6526 (1995)).

Additionally, the vector can contain, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; internal ribosome binding sites (IRESes), versatile multiple cloning sites; and T7 and SP6 RNA promoters for in vitro transcription of sense and antisense RNA. Suitable vectors and methods for producing vectors containing transgenes are well known and available in the art.

An expression vector comprising the nucleic acid can be transferred to a host cell by conventional techniques (e.g., electroporation, liposomal transfection, and calcium phosphate precipitation) and the transfected cells are then cultured by conventional techniques to produce the polypeptides described herein. In certain embodiments, the expression of the polypeptide described herein is regulated by a constitutive, an inducible or a tissue-specific promoter.

The host cells used to express the polypeptides described herein may be either bacterial cells such as *Escherichia coli*, or, preferably, eukaryotic cells. In certain embodiments, the cell is an isolated host cell. In certain embodiments, the cell is a HEK 293 cell.

A variety of host-expression vector systems may be utilized to express the polypeptides described herein. Such host-expression systems represent vehicles by which the coding sequences of the isolated polypeptides described herein may be produced and subsequently purified, but also represent cells which may, when transformed or transfected with the appropriate nucleotide coding sequences, express the polypeptides described herein in situ. These include, but are not limited to, microorganisms such as bacteria (e.g., *E. coli* and *B. subtilis*) transformed with recombinant bacteriophage DNA, plasmid DNA or cosmid DNA expression vectors containing coding sequences for the polypeptides described herein; yeast (e.g., Saccharomyces pichia) transformed with recombinant yeast expression vectors containing sequences encoding the polypeptides described herein; insect cell systems infected with recombinant virus expression vectors (e.g., baclovirus) containing the sequences encoding the polypeptides described herein; plant cell systems infected with recombinant virus expression vectors (e.g., cauliflower mosaic virus (CaMV) and tobacco mosaic virus (TMV) or transformed with recombinant plasmid expression vectors (e.g., Ti plasmid) containing sequences encoding the polypeptides described herein; or mammalian cell systems (e.g., COS, CHO, BHK, HEK 293, HEK 293T, 3T3 cells, lymphotic cells (see U.S. Pat. No. 5,807,715), Per C.6 cells (human retinal cells developed by Crucell) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the polypeptides being expressed. For example, when a large quantity of such a protein is to be produced, for the generation of pharmaceutical compositions of polypeptides described herein, vectors which direct the expression of high levels of polypeptide products that are readily purified may be desirable. Such vectors include, but are not limited, to the *E. coli* expression vector pUR278 (Rüther et al. (1983) "Easy Identification of cDNA Clones," EMBO J. 2: 1791-1794), in which the coding sequence may be ligated individually into the vector in frame with the lac Z coding region so that a polypeptide is produced; pIN vectors (Inouye et al. (1985) "Up-Promoter Mutations In The 1pp Gene of *Escherichia Coli*," Nucleic Acids Res. 13: 3101-3110; Van Heeke et al. (1989) "Expression of Human Asparagine Synthetase in *Escherichia Coli*," J. Biol. Chem. 24: 5503-5509); and the like. pGEX vectors may also be used to express foreign polypeptides with glutathione S-transferase (GST). In general, such polypeptides are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In an insect system, Autographa californica nuclear polyhedrosis virus (AcNPV) is used as a vector to express foreign genes. The virus grows in Spodoptera frugiperda cells. The coding sequence may be cloned individually into non-essential regions (e.g., the polyhedrin gene) of the virus and placed under control of an AcNPV promoter (e.g., the polyhedrin promoter).

In mammalian host cells, a number of viral-based expression systems may be utilized. In cases where an adenovirus is used as an expression vector, the coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region El or E3) will result in a recombinant virus that is viable and capable of expressing the immunoglobulin molecule in infected hosts (e.g., see Logan et al. (1984) "Adenovirus Tripartite Leader Sequence Enhances Translation Of mRNAs Late After Infection," Proc. Natl. Acad. Sci. USA 81: 3655-3659). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bitter et al. (1987) "Expression And Secretion Vectors For Yeast," Methods in Enzymol. 153: 516-544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Purification and modification of recombinant proteins is well known in the art such that the design of the polyprotein precursor could include a number of embodiments readily appreciated by a skilled worker. Any known proteases or peptidases known in the art can be used for the described modification of the precursor molecule.

Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, HeLa, COS, MDCK, HEK 293, HEK 293T, 3T3, WI38, BT483, Hs578T, HTB2, BT20 and T47D, CRL7030 and Hs578Bst. In certain embodiments, the host cell is a HEK 293 cell.

For long-term, high-yield production of recombinant proteins, stable expression is preferred. For example, cell lines which stably express polypeptides described herein may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the polypeptides described herein.

A number of selection systems may be used, including but not limited to the herpes simplex virus thymidine kinase (Wigler et al. (1977) "Transfer Of Purified Herpes Virus Thymidine Kinase Gene To Cultured Mouse Cells," Cell 11: 223-232), hypoxanthine-guanine phosphoribosyltransferase (Szybalska et al. (1992) "Use Of The HPRT Gene And The HAT Selection Technique In DNA-Mediated Transformation Of Mammalian Cells First Steps Toward Developing Hybridoma Techniques And Gene Therapy," Bioessays 14: 495-500), and adenine phosphoribosyltransferase (Lowy et al. (1980) "Isolation Of Transforming DNA: Cloning The Hamster aprt Gene," Cell 22: 817-823) genes can be employed in tk—, hgprt— or aprt— cells, respectively. Also, antimetabolite resistance can be used as the basis of selection for the following genes: dhfr, which confers resistance to methotrexate (Wigler et al. (1980) "Transformation Of Mammalian Cells With An Amplifiable Dominant-Acting Gene," Proc. Natl. Acad. Sci. USA 77: 3567-3570; O'Hare et al. (1981) "Transformation Of Mouse Fibroblasts To Methotrexate Resistance By A Recombinant Plasmid Expressing A Prokaryotic Dihydrofolate Reductase," Proc. Natl. Acad. Sci. USA 78: 1527-1531); gpt, which confers resistance to mycophenolic acid (Mulligan et al. (1981) "Selection For Animal Cells That Express The *Escherichia coli* Gene Coding For Xanthine-Guanine Phosphoribosyltransferase," Proc. Natl. Acad. Sci. USA 78: 2072-2076); neo, which confers resistance to the aminoglycoside G-418 (Tolstoshev (1993) "Gene Therapy, Concepts, Current Trials And Future Directions," Ann. Rev. Pharmacol. Toxicol. 32: 573-596; Mulligan (1993) "The Basic Science Of Gene Therapy," Science 260: 926-932; and Morgan et al. (1993) "Human Gene Therapy," Ann. Rev. Biochem. 62: 191-217) and hygro, which confers resistance to hygromycin (Santerre et al. (1984) "Expression of Prokaryotic Genes For Hygromycin B And G418 Resistance As Dominant-Selection Markers In Mouse L Cells," Gene 30: 147-156). Methods commonly known in the art of recombinant DNA technology which can be used are described in Ausubel et al. (eds.), 1993, Current Protocols in Molecular Biology, John Wiley & Sons, NY; Kriegler, 1990, Gene Transfer and Expression, A Laboratory Manual, Stockton Press, NY; and in Chapters 12 and 13, Dracopoli et al. (eds), 1994, Current Protocols in Human Genetics, John Wiley & Sons, NY.; Colberre-Garapin et al. (1981) "A New Dominant Hybrid Selective Marker For Higher Eukaryotic Cells," J. Mol. Biol. 150: 1-14.

The expression levels of the polypeptide described herein can be increased by vector amplification (for a review, see Bebbington and Hentschel, The use of vectors based on gene amplification for the expression of cloned genes in mammalian cells in DNA cloning, Vol. 3 (Academic Press, New York, 1987). When a marker in the vector system expressing a polypeptide described herein is amplifiable, increase in the level of inhibitor present in culture of host cell will increase the number of copies of the marker gene. Since the amplified region is associated with the nucleotide sequence of a polypeptide described herein, production of the polypeptide will also increase (Crouse et al. (1983) "Expression And Amplification Of Engineered Mouse Dihydrofolate Reductase Minigenes," Mol. Cell. Biol. 3: 257-266).

Once a polypeptide described herein has been recombinantly expressed, it may be purified by any method known in the art for purification of polypeptides, polyproteins or antibodies (e.g., analogous to antibody purification schemes based on antigen selectivity) for example, by chromatography (e.g., ion exchange, affinity, particularly by affinity for the specific antigen (optionally after Protein A selection where the polypeptide comprises an Fc domain (or portion thereof)), and sizing column chromatography), centrifugation, differential solubility, or by any other standard technique for the purification of polypeptides or antibodies.

Drug Delivery and Pharmaceutical Compositions

Also provided herein are drug delivery compositions comprising the polypeptides disclosed herein. A "drug delivery composition," as used herein, refers to any composition, in liquid, gel or solid form, comprising at least one biocompatible material and a polypeptide to be released from the composition. In certain embodiments, the polypeptide is released in vitro. In certain embodiments, the polypeptide is released in vivo, e.g., upon administration to a subject.

In certain embodiments, the biocompatible material comprises any synthetic or naturally occurring material that is suitable for containing and promoting the sustained or extended release of any polypeptide in the drug delivery compositions as described herein. Accordingly, the biocompatible material possesses properties that provide the advantageous properties of the compositions described herein (e.g., biodegradation, release profile of polypeptides). In certain embodiments, the biocompatible material extends the release of a polypeptide relative to administration of the same polypeptide in solution. In certain embodiments, the biocompatible material extends the release of a polypeptide relative to administration of the same polypeptide in solution by at least 5 minutes, 10 minutes, 20 minutes, 30 minutes, 40 minutes, 50 minutes, 60 minutes, 2 hours, 3 hours, 4 hours, 5 hours, 6 hours, 7 hours, 8 hours, 9 hours, 10 hours, 11 hours, 12 hours, 18 hours, 24 hours, 48 hours, 72 hours, 96 hours, 120 hours, 6 days, 7 days, 10 days, 2 weeks, 3 weeks, or 4 weeks. In certain embodiments, less than 100% of the polypeptide is released from the composition 5 minutes, 10 minutes, 20 minutes, 30 minutes, 40 minutes, 50 minutes, 60 minutes, 2 hours, 3 hours, 4 hours, 5 hours, 6 hours, 7 hours, 8 hours, 9 hours, 10 hours, 11 hours, 12 hours, 18 hours, 24 hours, 48 hours, 72 hours, 96 hours, 120 hours, 6 days, 7 days, 10 days, 2 weeks, 3 weeks, or 4 weeks after administration of the composition.

In certain embodiments, the biocompatible material comprises a polymer. In certain embodiments, the biocompatible material comprises a synthetic polymer.

In certain embodiments, the biocompatible material comprises hyaluronic acid, alginate, chitosan, chitin, chondroitin sulfate, dextran, gelatin, collagen, starch, cellulose, polysaccharide, fibrin, ethylene-vinyl acetate (EVA), poly(lactic-co-glycolic) acid (PLGA), polylactic acid (PLA), polyglycolic acid (PGA), polyethylene glycol (PEG), PEG diacrylate (PEGDA), disulfide-containing PEGDA (PEGSSDA), PEG dimethacrylate (PEGDMA), polydioxanone (PDO), polyhydroxybutyrate (PHB), poly(2-hydroxyethyl methacrylate) (pHEMA), polycaprolactone (PCL), poly(beta-amino ester) (PBAE), poly(ester amide), poly(propylene glycol) (PPG), poly(aspartic acid), poly(glutamic acid), poly(propylene fumarate) (PPF), poly(sebacic anhydride) (PSA), poly(trimethylene carbonate) (PTMC), poly(desaminotyrosyltyrosine alkyl ester carbonate) (PDTE), poly[bis(trifluoroethoxy) phosphazene], polyoxymethylene, single-wall carbon nanotubes, polyphosphazene, polyanhydride, poly(N-vinyl-2-pyrrolidone) (PVP), poly(vinyl alcohol) (PVA), poly(acrylic acid) (PAA), poly(methacrylic acid) (PMA), polyacetal, poly(alpha ester), poly(ortho ester), polyphosphoester, polyurethane, polycarbonate, polyamide, polyhydroxyalkanoate, polyglycerol, polyglucuronic acid, derivatives thereof, and/or combinations thereof.

In certain embodiments, the biocompatible material comprises a polyester. In certain embodiments, the biocompatible material comprises poly(lactic-co-glycolic acid), poly(lactic acid), poly(glycolic acid), poly(lactic-co-glycolic acid)-poly(ethylene glycol) copolymer, poly(lactic acid)-poly(ethylene glycol) copolymer, or poly(glycolic acid)-poly(ethylene glycol) copolymer. In certain embodiments, the biocompatible material comprises poly(lactic-co-glycolic acid) (PLGA).

In certain embodiments, the drug delivery composition comprises a hydrogel. Hydrogels can provide a scaffold that allows the components of the composition to be combined effectively and form a useful drug delivery system in a variety of routes of administration. In certain embodiments, the hydrogel comprises hyaluronic acid, alginate, chitosan, chitin, chondroitin sulfate, dextran, gelatin, collagen, starch, cellulose, polysaccharide, fibrin, ethylene-vinyl acetate (EVA), poly(lactic-co-glycolic) acid (PLGA), polylactic acid (PLA), polyglycolic acid (PGA), polyethylene glycol (PEG), PEG diacrylate (PEGDA), disulfide-containing PEGDA (PEGSSDA), PEG dimethacrylate (PEGDMA), polydioxanone (PDO), polyhydroxybutyrate (PHB), poly(-hydroxyethyl methacrylate) (pHEMA), polycaprolactone (PCL), poly(beta-amino ester) (PBAE), poly(ester amide), poly(propylene glycol) (PPG), poly(aspartic acid), poly(glutamic acid), poly(propylene fumarate) (PPF), poly(sebacic anhydride) (PSA), poly(trimethylene carbonate) (PTMC), poly(desaminotyrosyltyrosine alkyl ester carbonate) (PDTE), poly[bis(trifluoroethoxy)phosphazene], polyoxymethylene, single-wall carbon nanotubes, polyphosphazene, polyanhydride, poly(N-vinyl-2-pyrrolidone) (PVP), poly(vinyl alcohol) (PVA), poly(acrylic acid) (PAA), poly(methacrylic acid) (PMA), polyacetal, poly(alpha ester), poly (ortho ester), polyphosphoester, polyurethane, polycarbonate, polyamide, polyhydroxyalkanoate, polyglycerol, polyglucuronic acid, derivatives thereof, and/or combinations thereof.

In certain embodiments, the drug delivery composition comprises a particle or a hydrogel. In certain embodiments, the drug delivery composition comprises a particle. As used herein, the term "particle" refers to a small object, fragment, or piece of material and includes, without limitation, microparticles and nanoparticles. Particles may be composed of a single substance or multiple substances. In certain embodiments, the particles are substantially solid throughout and/or comprise a core that is substantially solid throughout. In certain embodiments, a particle may not include a micelle, a liposome, or an emulsion.

In certain embodiments, the particle comprises a core comprising one or more polymers. The core may contain a relatively high weight percentage of polymer(s) and may be referred to as a polymeric core. For instance, in certain embodiments, the weight percentage of polymers in the core may be greater than or equal to about 30 wt. %, greater than or equal to about 40 wt. %, greater than or equal to about 50 wt. %, greater than or equal to about 60 wt. %, greater than or equal to about 70 wt. %, greater than or equal to about 80 wt. %, or greater than or equal to about 90 wt. %. In certain embodiments, the polymeric core may consist essentially of one or more polymers and one or more pharmaceutically active agents. In general, any suitable biocompatible polymer may be used to form the core. In certain embodiments, the polymers may be selected based on compatibility with one or more pharmaceutically active agent, desired release characteristics, and/or the intended use of the pharmaceutically active agents. For instance, in certain embodiments, a polymer may be selected based on its compatibility with pharmaceutical applications and other consumer products (e.g., cosmetics, food).

In certain embodiments, the particles, described herein, may have a relatively small diameter. In certain embodiments, the particle is a nanoparticle. For instance, in certain embodiments, the characteristic dimension (e.g., average diameter) of the particles is less than about 1,000 nm, less than or equal to about 800 nm, less than or equal to about 600 nm, less than or equal to about 500 nm, less than or equal to about 400 nm, less than or equal to about 300 nm, less than or equal to about 200 nm, less than or equal to about 100 nm, or less than or equal to about 50 nm. In some instances, the characteristic dimension (e.g., average diameter) of the particles is may be between about 10 nm and about 800 nm, between about 10 nm and about 600 nm, between about 10 nm and about 500 nm, between about 10 nm and about 400 nm, between about 10 nm and about 300 nm, between about 10 nm and about 200 nm, or between about 10 nm and about 100 nm. In some instances, the particles have a diameter less than or equal to 100 nm. In certain cases, the characteristic dimension of the particles is between about 10 nm and about 100 nm. As used herein, the diameter of a particle for a non-spherical particle is the diameter of a perfect mathematical sphere having the same volume as the non-spherical particle. In general, the particles are approximately spherical; however the particles are not necessarily spherical but may assume other shapes (e.g., discs, rods) as well. The measurements described herein typically represent the average particle size of a population. However, in certain embodiments, the measurements may represent the range of sizes found in a population, or the maximum or minimum size of particles found in the population. In certain embodiments, the nanoparticle is a targeted nanoparticle. In certain embodiments, the nanoparticle inhibits clotting.

In certain embodiments, the particle is a microparticle. In certain embodiments, the particles may have an average diameter of less than 1 mm. For instance, in certain embodiments, the average diameter of the particles is less than about 1,000 microns, less than or equal to about 500 microns, less than or equal to about 100 microns, less than or equal to about 50 microns, less than or equal to about 10 microns, or less than or equal to about 5 microns and greater than or equal to about 1 micron.

In certain embodiments, the drug delivery composition comprises a particle, wherein the particle encapsulates the polypeptide within the particle. In certain embodiments, the particle is a nanoparticle. In certain embodiments, the particle is a microparticle.

In certain embodiments, the weight percentage of polypeptide in the particles is at least about 0.5%, at least about 1%, at least about 2%, at least about 4%, at least about 6%, at least about 8%, at least about 10%, at least about 15%, at least about 20%, at least about 25%, at least about 30%, at least about 35%, at least about 40%, at least about 45%, or at least about 50%. In some instances, the weight percentage of polypeptide in the particles is between about 0.5% and about 60%, between about 0.5% and about 50%, between about 0.5% and about 40%, between about 0.5% and about 30%, between about 1% and about 60%, between about 1% and about 50%, between about 1% and about 40%, between about 1% and about 30%, between about 2% and about 60%, between about 2% and about 50%, between about 2% and about 40%, or between about 2% and about 30%.

In certain embodiments, the particle comprises a polymer. In certain embodiments, the particle comprises a synthetic polymer. In certain embodiments, the particle comprises a polyester. In certain embodiments, the particle comprises poly(lactic acid)/polylactide, poly(glycolic acid), poly(lactic-co-glycolic acid), poly(caprolactone), a poly(orthoester), a poly(anhydride), a poly(ether ester) such as polydioxanone, a poly(carbonate), a poly(amino carbonate), a poly(hydroxyalkanoate) such as poly(3-hydroxybutyrate), a poly(3-hydroxybutyrate-co-3-hydroxyvalerate), a polyphosphazene, a polyacrylate, a poly(alkyl acrylate), a polyamide, a polyamine such as poly(amido amine) dendrimers, a polyether, a poly(ether ketone), a poly(alkaline oxide) such as polyethylene glycol, a polyacetylene, a polydiacetylene, a polysiloxane, a polyolefin, a polystyrene such as sulfonated polystyrene, a polycarbamate, a polyurea, a polyimide, a polysulfone, a polyurethane, a polyisocyanate, a polyacrylonitrile, a polysaccharide such as alginate and chitosan, a polypeptide, or derivatives or block, random, radial, linear, and teleblock copolymers, and blends of the above. The polymers may be homopolymers or copolymers. Other potentially suitable polymer molecules are described in the Polymer Handbook, Fourth Ed., Brandrup, J. Immergut, E. H., Grulke, E. A., Eds., Wiley-Interscience: 2003, which is incorporated herein by reference in its entirety.

In certain embodiments, the polymer may be a copolymer. In certain embodiments, the particle comprises poly(lactic-co-glycolic acid), poly(lactic acid), poly(glycolic acid), poly (lactic-co-glycolic acid)-poly(ethylene glycol) copolymer, poly(lactic acid)-poly(ethylene glycol) copolymer, or poly (glycolic acid)-poly(ethylene glycol) copolymer. In certain embodiments, the particle comprises poly(lactic-co-glycolic acid) (PLGA).

In certain embodiments, the particle extends the release of a polypeptide relative to administration of the same polypeptide in solution. In certain embodiments, the article extends the release of a polypeptide relative to administration of the same polypeptide in solution by at least 5 minutes, 10 minutes, 20 minutes, 30 minutes, 40 minutes, 50 minutes, 60 minutes, 2 hours, 3 hours, 4 hours, 5 hours, 6 hours, 7 hours, 8 hours, 9 hours, 10 hours, 11 hours, 12 hours, 18 hours, 24 hours, 48 hours, 72 hours, 96 hours, 120 hours, 6 days, 7 days, 10 days, 2 weeks, 3 weeks, or 4 weeks. In certain embodiments, less than 100% of the polypeptide is released from the particle 5 minutes, 10 minutes, 20 minutes, 30 minutes, 40 minutes, 50 minutes, 60 minutes, 2 hours, 3 hours, 4 hours, 5 hours, 6 hours, 7 hours, 8 hours, 9 hours, 10 hours, 11 hours, 12 hours, 18 hours, 24 hours, 48 hours, 72 hours, 96 hours, 120 hours, 6 days, 7 days, 10 days, 2 weeks, 3 weeks, or 4 weeks after administration of the composition. In certain embodiments, less than 100% of the polypeptide is released from the particle 5 minutes, 10 minutes, 20 minutes, 30 minutes, 40 minutes, 50 minutes, 60 minutes, 2 hours, 3 hours, 4 hours, 5 hours, 6 hours, 7 hours, 8 hours, 9 hours, 10 hours, 11 hours, 12 hours, 18 hours, 24 hours, 48 hours, 72 hours, 96 hours, 120 hours, 6 days, 7 days, 10 days, 2 weeks, 3 weeks, or 4 weeks after placing the microparticle in a buffered solution.

In certain embodiments, the polymer comprising the particle is biodegradable. In some instances, the polymer comprising the particle is a hydrolytically degradable polymer.

In certain embodiments, the polymer comprising the particle has any suitable molecular weight. For example, in certain embodiments, the number average molecular weight of one or more polymers of the particle may be greater than or equal to about 3,000 g/mol, greater than or equal to about 5,000 g/mol, greater than or equal to about 10,000 g/mol, greater than or equal to about 25,000 g/mol, greater than or equal to about 50,000 g/mol, about 70,000 g/mol, greater than or equal to about 100,000 g/mol, greater than or equal to about 250,000 g/mol, or greater than or equal to about 500,000 g/mol. In some instances, the number average molecular weight of one or more polymers of the particle may be less than or equal to about 1,000,000 g/mol, less than or equal to about 750,000 g/mol, less than or equal to about 500,000 g/mol, less than or equal to about 250,000 g/mol, less than or equal to about 100,000 g/mol, less than or equal to about 75,000 g/mol, less than or equal to about 50,000 g/mol, or less than or equal to about 25,000 g/mol. Combinations of the above-referenced ranges are also possible (e.g., greater than or equal to about 3,000 g/mol and less than or equal to about 1,000,000 g/mol). The number average molecular weight may be determined using gel permeation chromatography (GPC), nuclear magnetic resonance spectrometry (NMR), laser light scattering, intrinsic viscosity, vapor pressure osmometry, small angle neutron scattering, laser desorption ionization mass spectrometry, matrix assisted laser desorption ionization mass spectrometry (MALDI MS), or electrospray mass spectrometry or may be obtained from a manufacturer's specifications. Unless otherwise indicated the values of number average molecular weight described herein are determined by gel permeation chromatography (GPC).

It should be understood that, in certain embodiments, the particle may comprise other materials besides synthetic polymers and natural polymers (e.g., polysaccharides, carbohydrates, polypeptides). In certain embodiments, a ceramic such as calcium phosphate ceramic is used. Exemplary calcium phosphate ceramics include tricalcium phosphate, hydroxyapatite, and biphasic calcium phosphate.

In certain embodiments, the particles are biocompatible. For instance, in certain embodiments, addition of the particles to cells in vitro results in less than 20% cell death, less than or equal to about 15% cell death, less than or equal to about 12% cell death, less than or equal to about 10% cell death, less than or equal to about 8% cell death, less than or equal to about 5% cell death, less than or equal to about 3% cell death, less than or equal to about 2% cell death, or less than or equal to about 1% cell death and their administration in vivo does not induce inflammation or other such adverse effects.

In general, the particles are biodegradable. As used herein, "biodegradable" particles are those that, when introduced into cells, are broken down by the cellular machinery or by hydrolysis into components that the cells can either reuse or dispose of without significant toxic effects on the cells, i.e., fewer than about 20% (e.g, fewer than about 15%, fewer than about 10%, fewer than about 5%, fewer than about 3%, fewer than about 2%, fewer than about 1%) of the cells are killed when the components are added to cells in vitro. The components preferably do not cause inflammation or other adverse effects in vivo. In certain embodiments, the chemical reactions relied upon to break down the biodegradable particles are catalyzed. In other embodiments, the chemical reactions relied upon to break down the biodegradable particles are not catalyzed.

In another aspect, methods of preparing the particles are provided. In certain embodiments, the method comprises emulsifying the polypeptide in a solution containing a polymer to provide a first emulsification; emulsifying the first emulsification in a solution containing an emulsifying agent to provide a second emulsification; evaporating solvent; and isolating the particle.

In certain embodiments, the polypeptide is dissolved in an aqueous solution (e.g., a buffered solution) prior to the first emulsification. In certain embodiments, the solution containing a polymer comprises an organic solvent. In certain embodiments, the organic solvent is dichloromethane. In certain embodiments, the solution containing an emulsifying agent is an aqueous solution (e.g., a buffered solution). In certain embodiments, the emulsifier is or comprises a polymer. In certain embodiments, the emulsifier is or comprises polyvinyl alcohol (PVA). In certain embodiments, the emulsifier is or comprises about 0.01% to about 1% (w/v) polyvinyl alcohol (PVA). In certain embodiments, the emulsifier is or comprises about 0.1% to about 1% (w/v) polyvinyl alcohol (PVA). In certain embodiments, the emulsifier is or comprises about 0.1% (w/v) polyvinyl alcohol (PVA). In certain embodiments, the emulsifier is or comprises about 1% (w/v) polyvinyl alcohol (PVA). In certain embodiments, the solvent evaporated is the organic solvent. In certain embodiments isolating the particle comprises filtering.

In certain embodiments, the polymer of the first emulsification comprises a synthetic polymer. In certain embodiments, the polymer comprises a polyester. In certain embodiments, the polymer comprises poly(lactic acid)/polylactide, poly(glycolic acid), poly(lactic-co-glycolic acid), poly(caprolactone), a poly(orthoester), a poly(anhydride), a poly(ether ester) such as polydioxanone, a poly(carbonate), a poly(amino carbonate), a poly(hydroxyalkanoate) such as poly(3-hydroxybutyrate), a poly(3-hydroxybutyrate-co-3-hydroxyvalerate), a polyphosphazene, a polyacrylate, a poly (alkyl acrylate), a polyamide, a polyamine such as poly (amido amine) dendrimers, a polyether, a poly(ether ketone), a poly(alkaline oxide) such as polyethylene glycol, a polyacetylene, a polydiacetylene, a polysiloxane, a polyolefin, a polystyrene such as sulfonated polystyrene, a polycarbamate, a polyurea, a polyimide, a polysulfone, a polyurethane, a polyisocyanate, a polyacrylonitrile, a polysaccharide such as alginate and chitosan, a polypeptide, or derivatives or block, random, radial, linear, and teleblock copolymers, and blends of the above. In certain embodiments, the polymers is or comprises a homopolymer. In certain embodiments, the polymer is or comprises a copolymer. In certain embodiments, the polymer comprises poly(lactic-co-glycolic acid), poly(lactic acid), poly(glycolic acid), poly(lactic-co-glycolic acid)-poly(ethylene glycol) copolymer, poly(lactic acid)-poly(ethylene glycol) copolymer, or poly(glycolic acid)-poly(ethylene glycol) copolymer. In certain embodiments, the polymer comprises poly(lactic-co-glycolic acid) (PLGA).

A "pharmaceutical composition," as used herein, refers to the formulation of the polypeptide described herein in combination with a pharmaceutically acceptable carrier, or it may be the formulation of the drug delivery composition described herein in combination with a pharmaceutically acceptable carrier. The pharmaceutical composition can further comprise additional agents (e.g., for specific delivery, increasing half-life, or other therapeutic agents).

The term "pharmaceutically-acceptable carrier", as used herein, means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the polypeptide from one site (e.g., the delivery site) of the body, to another site (e.g., organ, tissue or portion of the body). A pharmaceutically acceptable carrier is "acceptable" in the sense of being compatible with the other ingredients of the formulation and not injurious to the tissue of the subject (e.g., physiologically compatible, sterile, physiologic pH, etc.). Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

In certain embodiments, a polypeptide of the present disclosure in a pharmaceutical and/or drug delivery composition is administered by injection, by means of a catheter, by means of a suppository, or by means of an implant, the implant being of a porous, non-porous, or gelatinous material, including a membrane, such as a sialastic membrane, or a fiber. Typically, when administering the composition, materials to which the polypeptide of the disclosure does not absorb are used.

In other embodiments, the polypeptides of the present disclosure are delivered in a controlled release system. In one embodiment, a pump may be used (see, e.g., Langer, 1990, Science 249: 1527-1533; Sefton, 1989, CRC Crit. Ref. Biomed. Eng. 14: 201; Buchwald et al., 1980, Surgery 88: 507; Saudek et al., 1989, N. Engl. J. Med. 321: 574). In another embodiment, polymeric materials can be used. (See, e.g., Medical Applications of Controlled Release (Langer and Wise eds., CRC Press, Boca Raton, Fla., 1974); Controlled Drug Bioavailability, Drug Product Design and Performance (Smolen and Ball eds., Wiley, New York, 1984); Ranger and Peppas, 1983, Macromol. Sci. Rev. Macromol. Chem. 23: 61. See also Levy et al., 1985, Science 228: 190; During et al., 1989, Ann. Neurol. 25: 351; Howard et al., 1989, J. Neurosurg. 71: 105.) Other controlled release systems are discussed, for example, in Langer, supra.

The polypeptide of the present disclosure can be administered as pharmaceutical compositions comprising a therapeutically effective amount of a binding agent and one or more pharmaceutically compatible ingredients.

In certain embodiments, the pharmaceutical and/or drug delivery composition is formulated in accordance with routine procedures as a pharmaceutical composition adapted for intravenous or subcutaneous administration to a subject, e.g., a human being. Typically, compositions for administration by injection are solutions in sterile isotonic aqueous buffer. Where necessary, the composition can also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

A pharmaceutical and/or drug delivery composition for systemic administration may be a liquid, e.g., sterile saline, lactated Ringer's or Hank's solution. In addition, the pharmaceutical and/or drug delivery composition can be in solid forms and re-dissolved or suspended immediately prior to use. Lyophilized forms are also contemplated.

The pharmaceutical and/or drug delivery composition can be contained within a lipid particle or vesicle, such as a liposome or microcrystal, which is also suitable for parenteral administration. The particles can be of any suitable structure, such as unilamellar or plurilamellar, so long as compositions are contained therein. The polypeptides of the present disclosure can be entrapped in 'stabilized plasmid-lipid particles' (SPLP) containing the fusogenic lipid dioleoylphosphatidylethanolamine (DOPE), low levels (5-10 mol%) of cationic lipid, and stabilized by a polyethyleneglycol (PEG) coating (Zhang Y. P. et al., Gene Ther. 1999, 6: 1438-47). Positively charged lipids such as N-[1-(2,3-dioleoyloxi)propyl]-N,N,N-trimethyl-amoniummethylsulfate, or "DOTAP," are particularly preferred for such particles and vesicles. The preparation of such lipid particles is well known. See, e.g., U.S. Pat. Nos. 4,880,635; 4,906,477; 4,911,928; 4,917,951; 4,920,016; and 4,921,757.

The pharmaceutical and/or drug delivery compositions of the present disclosure may be administered or packaged as a unit dose, for example. The term "unit dose" when used in reference to a pharmaceutical composition of the present disclosure refers to physically discrete units suitable as unitary dosage for the subject, each unit containing a predetermined quantity of active material calculated to produce the desired therapeutic effect in association with the required diluent; i.e., carrier, or vehicle.

Pharmaceutical and/or drug delivery compositions that may be used in accordance with the present disclosure may be directly administered to a subject or may be administered to a subject in need thereof in a therapeutically effective amount. The term "therapeutically effective amount" refers to the amount necessary or sufficient to realize a desired biologic effect. For example, a therapeutically effective amount may be that amount sufficient to ameliorate one or more symptoms of the disease or disorder. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the particular subject. The effective amount for any particular application can vary depending on such factors as the disease or condition being treated, the particular pharmaceutically compositions being administered the size of the subject, or the severity of the disease or condition. One of ordinary skill in the art can empirically determine the effective amount of a particular therapeutic compound associated with the present disclosure without necessitating undue experimentation.

In certain embodiments, an effective amount of a polypeptide for administration one or more times a day to a 70 kg adult human comprises about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a polypeptide per unit dosage form.

In certain embodiments, the polypeptide of the disclosure may be administered at dosage levels sufficient to deliver from about 0.001 mg/kg to about 100 mg/kg, from about mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, or from about 0.1 mg/kg to about 10 mg/kg of subject body weight per day, one or more times a day, to obtain the desired therapeutic effect.

A "prophylactically effective amount" of a polypeptide described herein is an amount sufficient to prevent a condition, or one or more symptoms associated with the condition or prevent its recurrence. A prophylactically effective amount of a polypeptide means an amount of a polypeptide, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

The formulations of the present disclosure are administered in pharmaceutically acceptable solutions, which may routinely contain pharmaceutically acceptable concentrations of salt, buffering agents, preservatives, compatible carriers, and optionally other therapeutic ingredients.

For use in therapy, an effective amount of the polypeptide of the present disclosure can be administered to a subject by any mode that delivers the polypeptide to the desired location, e.g., mucosal, injection, systemic, etc. Administering the pharmaceutical and/or drug delivery compositions of the present disclosure may be accomplished by any means known to the skilled artisan. In certain embodiments, the polypeptide, pharmaceutical composition, and/or drug delivery composition is administered subcutaneously, intracutaneously, intravenously, intramuscularly, intraarticularly, intraarterially, intrasynovially, intrasternally, intrathecally, intralesionally, or intracranially.

For oral administration, the polypeptide of the present disclosure can be formulated readily by combining the polypeptide and/or drug delivery composition with pharmaceutically acceptable carriers well known in the art. Such carriers enable the compounds of the present disclosure to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP). If desired, disintegrating agents may be added, such as the cross linked polyvinyl pyrrolidone, agar, or alginic acid or a salt thereof such as sodium alginate. Optionally, the oral formulations may also be formulated in saline or buffers, i.e., EDTA for neutralizing internal acid conditions or may be administered without any carriers.

Also specifically contemplated are oral dosage forms of the above component or components. The component or components may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline (Abuchowski and Davis, 1981, "Soluble Polymer-Enzyme Adducts" In: Enzymes as Drugs, Hocenberg and Roberts, eds., Wiley-Interscience, New York, NY, pp. 367-383; Newmark, et al., 1982, J. Appl. Biochem. 4: 185-189). Other polymers that could be used are poly-1,3-dioxolane and poly-1,3,6-tioxocane. Preferred for pharmaceutical usage, as indicated above, are polyethylene glycol moieties.

The location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the therapeutic agent or by release of the biologically active material beyond the stomach environment, such as in the intestine.

To ensure full gastric resistance a coating impermeable to at least pH 5.0 is preferred. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e., powder; for liquid forms, a soft gelatin shell may be used. The shell material of cachets could be thick starch or other edible paper. For pills, lozenges, molded tablets or tablet triturates, moist massing techniques can be used.

The polypeptide and/or drug delivery composition can be included in the formulation as fine multi particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the polypeptide and/or drug delivery composition may be formulated (such as by liposome or microsphere encapsulation) and then further contained within an edible product, such as a refrigerated beverage containing colorants and flavoring agents.

One may dilute or increase the volume of the polypeptide and/or drug delivery composition with an inert material. These diluents could include carbohydrates, especially mannitol, a lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the polypeptide and/or drug delivery composition into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the polypeptide and/or drug delivery composition together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the polypeptide and/or drug delivery composition to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the polypeptide during formulation and to aid rearrangement during compression might be added. The glidants may include starch, talc, pyrogenic silica and hydrated silicoaluminate.

To aid dissolution of the polypeptide and/or drug delivery composition into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential nonionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the polypeptide and/or drug delivery composition either alone or as a mixture in different ratios.

Pharmaceutical preparations which can be used orally include push fit capsules made of gelatin, as well as soft, sealed capsules made of gelatin and a plasticizer, such as glycerol or sorbitol. The push fit capsules can contain the active ingredients in admixture with filler such as lactose, binders such as starches, and/or lubricants such as talc or magnesium stearate and, optionally, stabilizers. In soft capsules, the polypeptide and/or drug delivery composition may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the polypeptide and/or compositions for use according to the present disclosure may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The pharmaceutical and/or drug delivery compositions of the present disclosure, when desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the polypeptide and/or drug delivery composition may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical polypeptide and/or drug delivery compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical and/or drug delivery compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical and/or drug delivery compositions are suitable for use in a variety of drug delivery systems. For a brief review of methods for drug delivery, see Langer, Science 249: 1527-1533, 1990, which is incorporated herein by reference.

The pharmaceutical and/or drug delivery compositions of the present disclosure and optionally other therapeutics may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

Also encompassed by the disclosure are kits (e.g., pharmaceutical packs). The kits provided may comprise a drug delivery composition, pharmaceutical composition, or polypeptide described herein and a container (e.g., a vial, ampule, bottle, syringe, and/or dispenser package, or other suitable container). In certain embodiments, provided kits may optionally further include a second container comprising a pharmaceutical excipient for dilution or suspension of a pharmaceutical composition or compound described herein. In certain embodiments, the pharmaceutical composition or compound described herein provided in the first container and the second container are combined to form one unit dosage form.

In certain embodiments, a kit described herein further includes instructions for using the kit. A kit described herein may also include information as required by a regulatory agency such as the U.S. Food and Drug Administration (FDA). In certain embodiments, the information included in the kits is prescribing information. In certain embodiments, a kit described herein may include one or more additional pharmaceutical agents described herein as a separate composition.

Methods of Use/Treatment

In addition to thrombotic thrombocytopenic purpura (TTP), abnormal activity of ADAMTS13 has been implicated in the pathophysiology of high impact disease process affecting human health. Insufficiency of ADAMTS13 is the cause of TTP and contributes in microangiopathy in sickle cell disease (SCD). Recombinant ADAMTS13 is being tested as replacement therapy for TTP, and at supra-physiologic concentrations for moderating vaso-occlusive crisis in SCD (*Blood Coagul Fibrinolysis,* 2021 Jul. 23. doi: 10.1097/MBC.0000000000001064. Epub ahead of print). Genome-wide association studies have identified ADAMTS13 to be associated with stroke in adults and pediatric populations. Low plasmatic ADAMTS13 has been recently demonstrated to be positively associated with stroke (*J Thromb Haemost.* 2016 Nov; 14(11) :2114-2120) in a large prospective cohort of adult patients. In addition, abnormal ADAMTS13 has been described to participate in the etiology of ischemic heart disease (*Blood,* 2015 Dec 17; 126(25): 2739-46). Short and long-term supplementation of ADAMTS13 plasmatic activity for these and additional disease processes have potential therapeutic advantages as therapy or prophylaxis in pro-thrombotic conditions mediated by abnormal ADAMTS13/VWF. In addition, recombinant ADAMTS13 has demonstrated to carry significant thrombolytic activity when given locally to mature thrombus composed primarily of VWF in murine models of thrombosis (*Blood,* 2016 May 12; 127(19): 2337-45). These experimental findings in mice suggest that recombinant ADAMTS13 can be potentially used as a thrombolytic agent in humans given the proper concentration, activity and delivery system.

Accordingly, provided herein are methods of treating or preventing a thrombotic disease or condition, the methods comprising administering to a subject in need thereof a therapeutically effective amount of the polypeptide. In certain embodiments, the polypeptide is administered in the form of the polypeptide, a pharmaceutical composition comprising the polypeptide, a drug delivery composition comprising the polypeptide, or a pharmaceutical composition comprising the drug delivery composition.

In certain embodiments, the thrombotic disease involves abnormal thrombus formation (e.g., thrombotic disease mediated by von Willebrand Factor (VWF)). In certain embodiments, the thrombotic disease or condition is acquired thrombotic thrombocytopenic purpura (TTP), hereditary thrombotic thrombocytopenic purpura (TTP) thrombotic microangiopathy, thrombocytopenia, microvascular thrombosis, arterial thrombosis, acute myocardial infarction (AMI), stroke, sepsis, disseminated intravascular coagulation (DIC), cerebral infarction, ischemic/reperfusion injury, deep vein thrombosis (DVT), pulmonary embolism, sickle cell disease (SCD), or sickle cell crisis. In certain embodiments, the thrombotic disease or condition is acquired thrombotic thrombocytopenic purpura (TTP), hereditary thrombotic thrombocytopenic purpura (TTP) thrombotic microangiopathy, thrombocytopenia, microvascular thrombosis, arterial thrombosis, acute myocardial infarction (AMI), stroke, sepsis, disseminated intravascular coagulation (DIC), cerebral infarction, ischemic/reperfusion injury, deep vein thrombosis (DVT), pulmonary embolism, or sickle cell crisis. In certain embodiments, the thrombotic disease or condition is acquired thrombotic thrombocytopenic purpura (TTP) or hereditary thrombotic thrombocytopenic purpura (TTP). In certain embodiments, the thrombotic disease or condition is acquired thrombotic thrombocytopenic purpura (TTP). In certain embodiments, the thrombotic disease or condition is hereditary thrombotic thrombocytopenic purpura (TTP). In certain embodiments, the thrombotic disease or condition is sickle cell disease (SCD).

In certain embodiments, the administering is or comprises subcutaneous, intracutaneous, intravenous, intraperitoneal, intramuscular, intraarticular, intraarterial, intrasynovial, intrasternal, intrathecal, intralesional, or intracranial administration. In certain embodiments, the administering is or comprises subcutaneous administration.

The term "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In certain embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay or prevent recurrence.

The term "prevent," "preventing," or "prevention" refers to a prophylactic treatment of a subject who is not and was not with a disease but is at risk of developing the disease or who was with a disease, is not with the disease, but is at risk of regression of the disease. In certain embodiments, the subject is at a higher risk of developing the disease or at a higher risk of regression of the disease than an average healthy member of a population.

The terms "condition," "disease," and "disorder" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal. The term "patient" refers to a human subject in need of treatment of a disease.

In certain embodiments, after administering the polypeptide, a pharmaceutical composition comprising the polypeptide, a drug delivery composition comprising the polypeptide, or a pharmaceutical composition comprising the drug delivery composition, ADAMTS13 plasma concentration in the subject is increased over baseline native ADAMTS13 plasma concentration in the subject. In certain embodiments, ADAMTS13 plasma concentration in the subject is increased over baseline native ADAMTS13 plasma concentration in the subject by at least 1%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%. The increase may be measured at any time point after administering (e.g., 15 min, 30 min. 1 hr, 2 hr, 4 hr, 6 hr, 8 hr, 12 hr, 24 hr, 36 hr).

In certain embodiments, after administering the polypeptide, a pharmaceutical composition comprising the polypeptide, a drug delivery composition comprising the polypeptide, or a pharmaceutical composition comprising the drug delivery composition, ADAMTS13 plasma activity in the subject is increased over baseline native ADAMTS13 plasma activity in the subject. In certain embodiments, ADAMTS13 plasma activity in the subject is increased over baseline native ADAMTS13 plasma activity in the subject by at least 1%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%. The increase may be measured at any time point after administering (e.g., 15 min, 30 min. 1 hr, 2 hr, 4 hr, 6 hr, 8 hr, 12 hr, 24 hr, 36 hr).

As described herein, ADAMTS13 is a zinc-containing metalloprotease enzyme that cleaves von Willebrand factor (VWF), a large protein involved in blood clotting.

Accordingly, provided herein are methods of cleaving von Willebrand factor (VWF), the method comprising contacting the polypeptide with VWF. In certain embodiments, the contacting is carried out in vitro. In certain embodiments, the contacting is carried out in vivo. In certain embodiments, the contacting is carried out in a cell. In certain embodiments, the polypeptide is administered in the form of the polypeptide, a pharmaceutical composition comprising the polypeptide, a drug delivery composition comprising the polypeptide, or a pharmaceutical composition comprising the drug delivery composition.

In certain embodiments, the amount of VWF cleaved is at least 1%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% of the VWF present in a subject, a sample from a subject, or a sample from another source.

Some of the embodiments, advantages, features, and uses of the technology disclosed herein will be more fully understood from the Examples below. The Examples are intended to illustrate some of the benefits of the present disclosure and to describe particular embodiments, but are not intended to exemplify the full scope of the disclosure and, accordingly, do not limit the scope of the disclosure.

EXAMPLES

ADAMTS13 Sequence Selection

A modified truncation of the full-length wild type ADAMTS13 sequence of public domain (NCBI accession number: NM_139025.4.) was specifically designed to preserve ADAMTS13 protease activity with the minimum amino acid sequence in order to facilitate the incorporation into a drug delivery system. The result is a 685 amino acid sequence which spans the native metalloprotease, disintegrin, TSP1 repeat, cysteine rich and includes the spacer domains with an observed molecular weight of 80kDa. The full-length wild type ADAMTS13 is composed of 1427 amino acids, the truncated wild-type ADAMTS13 is composed of 685 amino acids, and mrADAMTS13 is composed of 719 amino acids.

Codon Optimization

Codon optimization of the truncated wild-type ADAMTS13 was performed by Genscript using a proprietary OptimumGene algorithm. OptimumGene algorithm takes into consideration several factors like codon adaptability, mRNA structure and cis-elements playing a role in transcription and translation. Full-length wild type and codon optimized truncated wild-type ADAMTS13 sequences were synthesized and cloned in to pcDNA5/FRT/V5-His Topo vector (ThermoFisher) by Genscript. See review of codon Optimization of recombinant proteins (*Int J Biochem Cell Biol.* 2015 July; 64: 58-74.)

Cell Expression System

The plasmids encoding full-length wild type, truncated wild-type and codon optimized truncated wild-type variants (mrADAM'FS13) were then employed to generate stable expression cell lines using Flp-In HEK293 cells (ThermoFisher). These cells were designed to express protein of interest from a single copy per cell integrated at a specific genomic location. For the generation of stable expression cell lines, Flp-In cells were co-transfected with the full-length wild type, truncated wild-type or codon optimized truncated wild-type (mrADAMTS13) constructs and pOG44 helper plasmid expressing flp recombinase enzyme. Flp recombinase mediates recombination between FRT sites in plasmid. constructs and Flp-In host cells thereby integrating the gene of interest into cells. Stably transfected Flp-In cells were selected in the presence of 300 μg/mL hygromycin.

Description of the Full-Length Wild Type ADAMT13, Truncated Wild-Type ADAMTS13 and Codon Optimized Truncated Wild-Type ADAMTS13 (mrADAMTS13) Sequences As descriptive comparison to evaluate the secretory properties of mrADAMTS13, the full-length wild type sequence or truncated wild-type ADAMTS13 were created to study by western blot and FRETS-VWF-73 assay. The sequences are described below:

ADAMTS13 full-length wild Type DNA Sequence (SEQ ID NO: 1)

```
ATGCACCAGCGTCACCCCCGGGCAAGATGCCCTCCCCTCTGTGTGGCCGGAATCCTTGCCTGTGGCT

TTCTCCTGGGCTGCTGGGGACCCTCCCATTTCCAGCAGAGTTGTCTTCAGGCTTTGGAGCCACAGGC

CGTGTCTTCTTACTTGAGCCCTGGTGCTCCCTTAAAAGGCCGCCCTCCTTCCCCTGGCTTCCAGAGGC

AGAGGCAGAGGCAGAGGCGGGCTGCAGGCGGCATCCTACACCTGGAGCTGCTGGTGGCCGTGGGCC

CCGATGTCTTCCAGGCTCACCAGGAGGACACAGAGCGCTATGTGCTCACCAACCTCAACATCGGGG

CAGAACTGCTTCGGGACCCGTCCCTGGGGGCTCAGTTTCGGGTGCACCTGGTGAAGATGGTCATTCT

GACAGAGCCTGAGGGTGCTCCAAATATCACAGCCAACCTCACCTCGTCCCTGCTGAGCGTCTGTGGG

TGGAGCCAGACCATCAACCCTGAGGACGACACGGATCCTGGCCATGCTGACCTGGTCCTCTATATCA

CTAGGTTTGACCTGGAGTTGCCTGATGGTAACCGGCAGGTGCGGGGCGTCACCCAGCTGGGCGGTG

CCTGCTCCCCAACCTGGAGCTGCCTCATTACCGAGGACACTGGCTTCGACCTGGGAGTCACCATTGC

CCATGAGATTGGGCACAGCTTCGGCCTGGAGCACGACGGCGCGCCCGGCAGCGGCTGCGGCCCCAG

CGGACACGTGATGGCTTCGGACGGCGCCGCGCCCCGCGCCGGCCTCGCCTGGTCCCCCTGCAGCCGC

CGGCAGCTGCTGAGCCTGCTCAGCGCAGGACGGGCGCGCTGCGTGTGGGACCCGCCGCGGCCTCAA

CCCGGGTCCGCGGGGCACCCGCCGGATGCGCAGCCTGGCCTCTACTACAGCGCCAACGAGCAGTGC

CGCGTGGCCTTCGGCCCCAAGGCTGTCGCCTGCACCTTCGCCAGGGAGCACCTGGATATGTGCCAGG

CCCTCTCCTGCCACACAGACCCGCTGGACCAAAGCAGCTGCAGCCGCCTCCTCGTTCCTCTCCTGGA

TGGGACAGAATGTGGCGTGGAGAAGTGGTGCTCCAAGGGTCGCTGCCGCTCCCTGGTGGAGCTGAC

CCCCATAGCAGCAGTGCATGGGCGCTGGTCTAGCTGGGGTCCCCGAAGTCCTTGCTCCCGCTCCTGC

GGAGGAGGTGTGGTCACCAGGAGGCGGCAGTGCAACAACCCCAGACCTGCCTTTGGGGGGCGTGCA

TGTGTTGGTGCTGACCTCCAGGCCGAGATGTGCAACACTCAGGCCTGCGAGAAGACCCAGCTGGAG
```

-continued

TTCATGTCGCAACAGTGCGCCAGGACCGACGGCCAGCCGCTGCGCTCCTCCCCTGGCGGCGCCTCCT

TCTACCACTGGGGTGCTGCTGTACCACACAGCCAAGGGGATGCTCTGTGCAGACACATGTGCCGGGC

CATTGGCGAGAGCTTCATCATGAAGCGTGGAGACAGCTTCCTCGATGGGACCCGGTGTATGCCAAGT

GGCCCCCGGGAGGACGGGACCCTGAGCCTGTGTGTGTCGGGCAGCTGCAGGACATTTGGCTGTGAT

GGTAGGATGGACTCCCAGCAGGTATGGGACAGGTGCCAGGTGTGTGGTGGGGACAACAGCACGTGC

AGCCCACGGAAGGGCTCTTTCACAGCTGGCAGAGCGAGAGAATATGTCACGTTTCTGACAGTTACCC

CCAACCTGACCAGTGTCTACATTGCCAACCACAGGCCTCTCTTCACACACTTGGCGGTGAGGATCGG

AGGGCGCTATGTCGTGGCTGGGAAGATGAGCATCTCCCCTAACACCACCTACCCCTCCCTCCTGGAG

GATGGTCGTGTCGAGTACAGAGTGGCCCTCACCGAGGACCGGCTGCCCCGCCTGGAGGAGATCCGC

ATCTGGGGACCCCTCCAGGAAGATGCTGACATCCAGGTTTACAGGCGGTATGGCGAGGAGTATGGC

AACCTCACCCGCCCAGACATCACCTTCACCTACTTCCAGCCTAAGCCACGGCAGGCCTGGGTGTGGG

CCGCTGTGCGTGGGCCCTGCTCGGTGAGCTGTGGGGCAGGGCTGCGCTGGGTAAACTACAGCTGCCT

GGACCAGGCCAGGAAGGAGTTGGTGGAGACTGTCCAGTGCCAAGGGAGCCAGCAGCCACCAGCGT

GGCCAGAGGCCTGCGTGCTCGAACCCTGCCCTCCCTACTGGGCGGTGGGAGACTTCGGCCCATGCAG

CGCCTCCTGTGGGGGTGGCCTGCGGGAGCGGCCAGTGCGCTGCGTGGAGGCCCAGGGCAGCCTCCT

GAAGACATTGCCCCCAGCCCGGTGCAGAGCAGGGGCCCAGCAGCCAGCTGTGGCGCTGGAAACCTG

CAACCCCCAGCCCTGCCCTGCCAGGTGGGAGGTGTCAGAGCCCAGCTCATGCACATCAGCTGGTGG

AGCAGGCCTGGCCTTGGAGAACGAGACCTGTGTGCCAGGGGCAGATGGCCTGGAGGCTCCAGTGAC

TGAGGGGCCTGGCTCCGTAGATGAGAAGCTGCCTGCCCCTGAGCCCTGTGTCGGGATGTCATGTCCT

CCAGGCTGGGGCCATCTGGATGCCACCTCTGCAGGGGAGAAGGCTCCCTCCCCATGGGGCAGCATC

AGGACGGGGGCTCAAGCTGCACACGTGTGGACCCCTGCGGCAGGGTCGTGCTCCGTCTCCTGCGGG

CGAGGTCTGATGGAGCTGCGTTTCCTGTGCATGGACTCTGCCCTCAGGGTGCCTGTCCAGGAAGAGC

TGTGTGGCCTGGCAAGCAAGCCTGGGAGCCGGCGGGAGGTCTGCCAGGCTGTCCCGTGCCCTGCTC

GGTGGCAGTACAAGCTGGCGGCCTGCAGCGTGAGCTGTGGGAGAGGGGTCGTGCGGAGGATCCTGT

ATTGTGCCCGGGCCCATGGGGAGGACGATGGTGAGGAGATCCTGTTGGACACCCAGTGCCAGGGGC

TGCCTCGCCCGGAACCCCAGGAGGCCTGCAGCCTGGAGCCCTGCCCACCTAGGTGGAAAGTCATGT

CCCTTGGCCCATGTTCGGCCAGCTGTGGCCTTGGCACTGCTAGACGCTCGGTGGCCTGTGTGCAGCT

CGACCAAGGCCAGGACGTGGAGGTGGACGAGGCGGCCTGTGCGGCGCTGGTGCGGCCCGAGGCCA

GTGTCCCCTGTCTCATTGCCGACTGCACCTACCGCTGGCATGTTGGCACCTGGATGGAGTGCTCTGTT

TCCTGTGGGGATGGCATCCAGCGCCGGCGTGACACCTGCCTCGGACCCCAGGCCCAGGCGCCTGTGC

CAGCTGATTTCTGCCAGCACTTGCCCAAGCCGGTGACTGTGCGTGGCTGCTGGGCTGGGCCCTGTGT

GGGACAGGGTACGCCCAGCCTGGTGCCCCACGAAGAAGCCGCTGCTCCAGGACGGACCACAGCCAC

CCCTGCTGGTGCCTCCCTGGAGTGGTCCCAGGCCCGGGGCCTGCTCTTCTCCCCGGCTCCCCAGCCTC

GGCGGCTCCTGCCCGGGCCCCAGGAAAACTCAGTGCAGTCCAGTGCCTGTGGCAGGCAGCACCTTG

AGCCAACAGGAACCATTGACATGCGAGGCCCAGGGCAGGCAGACTGTGCAGTGGCCATTGGGCGGC

CCCTCGGGGAGGTGGTGACCCTCCGCGTCCTTGAGAGTTCTCTCAACTGCAGTGCGGGGGACATGTT

GCTGCTTTGGGGCCGGCTCACCTGGAGGAAGATGTGCAGGAAGCTGTTGGACATGACTTTCAGCTCC

AAGACCAACACGCTGGTGGTGAGGCAGCGCTGCGGGCGGCCAGGAGGTGGGGTGCTGCTGCGGTAT

GGGAGCCAGCTTGCTCCTGAAACCTTCTACAGAGAATGTGACATGCAGCTCTTTGGGCCCTGGGGTG

AAATCGTGAGCCCCTCGCTGAGTCCAGCCACGAGTAATGCAGGGGGCTGCCGGCTCTTCATTAATGT

-continued

GGCTCCGCACGCACGGATTGCCATCCATGCCCTGGCCACCAACATGGGCGCTGGGACCGAGGGAGC

CAATGCCAGCTACATCTTGATCCGGGACACCCACAGCTTGAGGACCACAGCGTTCCATGGGCAGCA

GGTGCTCTACTGGGAGTCAGAGAGCAGCCAGGCTGAGATGGAGTTCAGCGAGGGCTTCCTGAAGGC

TCAGGCCAGCCTGCGGGGCCAGTACTGGACCCTCCAATCATGGGTACCGGAGATGCAGGACCCTCA

GTCCTGGAAGGGAAAGGAAGGAACCAAGGGCGAGCTTGGTACCGAGCTCGGATCCGAAGGTAAGC

CTATCCCTAACCCTCTCCTCGGTCTCGATTCTACGCGTACCGGTCATCATCACCATCACCATTGA

Truncated ADAMTS13 Wild Type DNA Sequence (SEQ ID NO: 2)

ATGCACCAGCGTCACCCCCGGGCAAGATGCCCTCCCCTCTGTGTGGCCGGAATCCTTGCCTGTGGCT

TTCTCCTGGGCTGCTGGGGACCCTCCCATTTCCAGCAGAGTTGTCTTCAGGCTTTGGAGCCACAGGC

CGTGTCTTCTTACTTGAGCCCTGGTGCTCCCTTAAAAGGCCGCCCTCCTTCCCCTGGCTTCCAGAGGC

AGAGGCAGAGGCAGAGGCGGGCTGCAGGCGGCATCCTACACCTGGAGCTGCTGGTGGCCGTGGGCC

CCGATGTCTTCCAGGCTCACCAGGAGGACACAGAGCGCTATGTGCTCACCAACCTCAACATCGGGG

CAGAACTGCTTCGGGACCCGTCCCTGGGGGCTCAGTTTCGGGTGCACCTGGTGAAGATGGTCATTCT

GACAGAGCCTGAGGGTGCTCCAAATATCACAGCCAACCTCACCTCGTCCCTGCTGAGCGTCTGTGGG

TGGAGCCAGACCATCAACCCTGAGGACGACACGGATCCTGGCCATGCTGACCTGGTCCTCTATATCA

CTAGGTTTGACCTGGAGTTGCCTGATGGTAACCGGCAGGTGCGGGGCGTCACCCAGCTGGGCGGTG

CCTGCTCCCCAACCTGGAGCTGCCTCATTACCGAGGACACTGGCTTCGACCTGGGAGTCACCATTGC

CCATGAGATTGGGCACAGCTTCGGCCTGGAGCACGACGGCGCGCCCGGCAGCGGCTGCGGCCCCAG

CGGACACGTGATGGCTTCGGACGGCGCCGCGCCCCGCGCCGGCCTCGCCTGGTCCCCCTGCAGCCGC

CGGCAGCTGCTGAGCCTGCTCAGCGCAGGACGGGCGCGCTGCGTGTGGGACCCGCCGCGGCCTCAA

CCCGGGTCCGCGGGGCACCCGCCGGATGCGCAGCCTGGCCTCTACTACAGCGCCAACGAGCAGTGC

CGCGTGGCCTTCGGCCCCAAGGCTGTCGCCTGCACCTTCGCCAGGGAGCACCTGGATATGTGCCAGG

CCCTCTCCTGCCACACAGACCCGCTGGACCAAAGCAGCTGCAGCCGCCTCCTCGTTCCTCTCCTGGA

TGGGACAGAATGTGGCGTGGAGAAGTGGTGCTCCAAGGGTCGCTGCCGCTCCCTGGTGGAGCTGAC

CCCCATAGCAGCAGTGCATGGGCGCTGGTCTAGCTGGGGTCCCCGAAGTCCTTGCTCCCGCTCCTGC

GGAGGAGGTGTGGTCACCAGGAGGCGGCAGTGCAACAACCCCAGACCTGCCTTTGGGGGGCGTGCA

TGTGTTGGTGCTGACCTCCAGGCCGAGATGTGCAACACTCAGGCCTGCGAGAAGACCCAGCTGGAG

TTCATGTCGCAACAGTGCGCCAGGACCGACGGCCAGCCGCTGCGCTCCTCCCCTGGCGGCGCCTCCT

TCTACCACTGGGGTGCTGCTGTACCACACAGCCAAGGGGATGCTCTGTGCAGACACATGTGCCGGGC

CATTGGCGAGAGCTTCATCATGAAGCGTGGAGACAGCTTCCTCGATGGGACCCGGTGTATGCCAAGT

GGCCCCCGGGAGGACGGGACCCTGAGCCTGTGTGTGTCGGGCAGCTGCAGGACATTTGGCTGTGAT

GGTAGGATGGACTCCCAGCAGGTATGGGACAGGTGCCAGGTGTGTGGTGGGGACAACAGCACGTGC

AGCCCACGGAAGGGCTCTTTCACAGCTGGCAGAGCGAGAGAATATGTCACGTTTCTGACAGTTACCC

CCAACCTGACCAGTGTCTACATTGCCAACCACAGGCCTCTCTTCACACACTTGGCGGTGAGGATCGG

AGGGCGCTATGTCGTGGCTGGGAAGATGAGCATCTCCCCTAACACCACCTACCCCTCCCTCCTGGAG

GATGGTCGTGTCGAGTACAGAGTGGCCCTCACCGAGGACCGGCTGCCCCGCCTGGAGGAGATCCGC

ATCTGGGGACCCCTCCAGGAAGATGCTGACATCCAGGTTTACAGGCGGTATGGCGAGGAGTATGGC

AACCTCACCCGCCCAGACATCACCTTCACCTACTTCCAGCCTAAGCCACGGCAGGCCAAGGGCGAG

CTTGGTACCGAGCTCGGATCCGAAGGTAAGCCTATCCCTAACCCTCTCCTCGGTCTCGATTCTACGC

GTACCGGTCATCATCACCATCACCATTGA

-continued mrADAMTS13 DNA Sequence
The codon optimized DNA sequence of the truncated wild type ADAMTS13 was prepared at Genscript to provide a codon optimized DNA sequence of mrADAMTS13.

(SEQ ID NO: 3)

ATGCATCAGAGACATCCACGGGCTAGGTGTCCTCCACTGTGCGTCGCTGGCATCCTGGCTTGCGGGT

TCCTGCTGGGCTGCTGGGGGCCTAGCCACTTCCAGCAGTCCTGCCTGCAGGCCCTGGAGCCACAGGC

CGTGAGCTCCTACCTGAGCCCTGGAGCACCACTGAAGGGCAGACCCCCTTCCCCTGGCTTCCAGAGA

CAGAGGCAGAGGCAGAGGAGAGCAGCAGGAGGCATCCTGCACCTGGAGCTGCTGGTGGCAGTGGG

ACCAGACGTGTTTCAGGCCCACCAGGAGGATACCGAGAGATATGTGCTGACAAACCTGAATATCGG

CGCCGAGCTGCTGAGGGACCCCAGCCTGGGAGCACAGTTCCGCGTGCACCTGGTGAAGATGGTCAT

CCTGACCGAGCCTGAGGGAGCTCCAAACATCACCGCCAATCTGACATCTAGCCTGCTGAGCGTGTGC

GGCTGGAGCCAGACCATCAACCCTGAGGACGATACAGACCCAGGCCACGCCGATCTGGTGCTGTAC

ATCACCAGATTTGACCTGGAGCTGCCAGATGGCAATAGGCAGGTGCGCGGAGTGACCCAGCTGGGA

GGAGCATGTTCCCCAACATGGTCTTGCCTGATCACCGAGGACACAGGCTTCGATCTGGGCGTGACAA

TCGCCCACGAGATCGGCCACTCCTTTGGCCTGGAGCACGACGGAGCACCAGGATCCGGATGCGGAC

CTTCTGGACACGTGATGGCATCTGATGGAGCAGCACCAAGGGCAGGCCTGGCATGGTCCCCCTGTTC

TAGGCGCCAGCTGCTGAGCCTGCTGTCCGCCGGAAGGGCCAGATGCGTGTGGGACCCACCCAGACC

CCAGCCTGGAAGCGCCGGCCACCCTCCAGATGCCCAGCCCGGCCTGTACTATTCCGCCAACGAGCA

GTGTAGGGTGGCCTTCGGCCCTAAGGCAGTGGCATGCACCTTTGCCAGAGAGCACCTGGACATGTGC

CAGGCCCTGTCCTGTCACACAGACCCCCTGGATCAGTCCTCTTGTTCTAGGCTGCTGGTGCCTCTGCT

GGATGGCACCGAGTGCGGCGTGGAGAAGTGGTGCAGCAAGGGCAGGTGTCGCTCCCTGGTGGAGCT

GACACCAATCGCAGCAGTGCACGGCCGCTGGAGCTCCTGGGGACCACGGAGCCCTTGCTCCAGATC

TTGTGGAGGAGGAGTGGTGACCCGGAGAAGGCAGTGTAACAATCCAAGGCCCGCCTTTGGCGGAAG

GGCATGCGTGGGAGCAGACCTGCAGGCCGAGATGTGCAATACCCAGGCCTGTGAGAAGACACAGCT

GGAGTTCATGTCCCAGCAGTGCGCAAGGACCGACGGACAGCCACTGAGATCTAGCCCTGGAGGAGC

ATCTTTTTATCACTGGGGAGCAGCAGTGCCACACAGCCAGGGCGATGCACTGTGCAGGCACATGTGC

CGCGCCATCGGCGAGTCTTTCATCATGAAGCGGGGCGACAGCTTTCTGGATGGAACCAGGTGTATGC

CATCCGGACCAAGGGAGGATGGCACCCTGTCTCTGTGCGTGAGCGGCTCCTGTCGGACATTCGGCTG

CGACGGCAGAATGGATAGCCAGCAAGTGTGGGACAGGTGCCAGGTGTGCGGAGGCGATAACTCTAC

CTGCAGCCCTAGGAAGGGATCTTTCACAGCAGGAAGGGCAAGAGAGTACGTGACGTTTCTGACCGT

GACACCAAACCTGACAAGCGTGTATATCGCCAATCACAGGCCCCTGTTTACCCACCTGGCCGTGCGG

ATCGGAGGCAGATACGTGGTGGCAGGCAAGATGTCTATCAGCCCAAATACCACATACCCATCCCTG

CTGGAGGACGGAAGGGTGGAGTATCGCGTGGCCCTGACAGAGGATCGGCTGCCTAGACTGGAGGAG

ATCAGGATCTGGGGACCACTGCAGGAGGACGCCGATATCCAGGTGTACCGCCGGTATGGCGAGGAG

TATGGCAATCTGACTCGCCCCGACATCACTTTCACATACTTCCAGCCCAAACCAAGGCAGGCAAAGG

GCGAGCTTGGTACCGAGCTCGGATCCGAAGGTAAGCCTATCCCTAACCCTCTCCTCGGTCTCGATTC

TACGCGTACCGGTCATCATCACCATCACCATTGA mrADAMTS13 Codon Optimized DNA sequence (includes expression vector pcDNA5/FRT/V5-HisTopovector)
The truncated ADAMTS13 codon optimized DNA sequence was synthesized by Genscript and cloned into a commercial pcDNA5/FRT/V5-His Topovector expression vector to provide the mrADAMTS13 codon optimized DNA sequence.
Truncated WT ADAMTS13 optimized ORF (underlined), V5 Tag (bold and italic), His Tag (bold and underlined), Stop codon (italic and underlined), and CMV promoter (bold).

-continued (SEQ ID NO: 4)

GACGGATCGGGAGATCTCCCGATCCCCTATGGTGCACTCTCAGTACAATCTGCTCTGATGCCGCATA

GTTAAGCCAGTATCTGCTCCCTGCTTGTGTGTTGGAGGTCGCTGAGTAGTGCGCGAGCAAAATTTAA

GCTACAACAAGGCAAGGCTTGACCGACAATTGCATGAAGAATCTGCTTAGGGTTAGGCGTTTTGCGC

TGCTTCGCGATGTACGGGCCAGATATACGCGTTGACATTGATTATTGACTAGTTATTAATAGTAA

TCAATTACGGGGTCATTAGTTCATAGCCCATATATGGAGTTCCGCGTTACATAACTTACGGTAA

ATGGCCCGCCTGGCTGACCGCCCAACGACCCCCGCCCATTGACGTCAATAATGACGTATGTTC

CCATAGTAACGCCAATAGGGACTTTCCATTGACGTCAATGGGTGGAGTATTTACGGTAAACTG

CCCACTTGGCAGTACATCAAGTGTATCATATGCCAAGTACGCCCCCTATTGACGTCAATGACG

GTAAATGGCCCGCCTGGCATTATGCCCAGTACATGACCTTATGGGACTTTCCTACTTGGCAGT

ACATCTACGTATTAGTCATCGCTATTACCATGGTGATGCGGTTTTGGCAGTACATCAATGGGC

GTGGATAGCGGTTTGACTCACGGGGATTTCCAAGTCTCCACCCCATTGACGTCAATGGGAGTT

TGTTTTGGCACCAAAATCAACGGGACTTTCCAAAATGTCGTAACAACTCCGCCCCATTGACGC

AAATGGGCGGTAGGCGTGTACGGTGGGAGGTCTATATAAGCAGAGCTCTCTGGCTAACTAGAG

AACCCACTGCTTACTGGCTTATCGAAATTAATACGACTCACTATAGGGAGACCCAAGCTGGCTAGCG

TTTAAACTTAAGCTCGCCCTT

ATGCATCAGAGACATCCACGGGCTAGGTGTCCTCCACTGTGCGTCGCTGGCATCCTGGCTTGCGGGT

TCCTGCTGGGCTGCTGGGGGCCTAGCCACTTCCAGCAGTCCTGCCTGCAGGCCCTGGAGCCACAGGC

CGTGAGCTCCTACCTGAGCCCTGGAGCACCACTGAAGGGCAGACCCCCTTCCCCTGGCTTCCAGAGA

CAGAGGCAGAGGCAGAGGAGAGCAGCAGGAGGCATCCTGCACCTGGAGCTGCTGGTGGCAGTGGG

ACCAGACGTGTTTCAGGCCCACCAGGAGGATACCGAGAGATATGTGCTGACAAACCTGAATATCGG

CGCCGAGCTGCTGAGGGACCCCAGCCTGGGAGCACAGTTCCGCGTGCACCTGGTGAAGATGGTCAT

CCTGACCGAGCCTGAGGGAGCTCCAAACATCACCGCCAATCTGACATCTAGCCTGCTGAGCGTGTGC

GGCTGGAGCCAGACCATCAACCCTGAGGACGATACAGACCCAGGCCACGCCGATCTGGTGCTGTAC

ATCACCAGATTTGACCTGGAGCTGCCAGATGGCAATAGGCAGGTGCGCGGAGTGACCCAGCTGGGA

GGAGCATGTTCCCCAACATGGTCTTGCCTGATCACCGAGGACACAGGCTTCGATCTGGGCGTGACAA

TCGCCCACGAGATCGGCCACTCCTTTGGCCTGGAGCACGACGGAGCACCAGGATCCGGATGCGGAC

CTTCTGGACACGTGATGGCATCTGATGGAGCAGCACCAAGGGCAGGCCTGGCATGGTCCCCCTGTTC

TAGGCGCCAGCTGCTGAGCCTGCTGTCCGCCGGAAGGGCCAGATGCGTGTGGGACCCACCCAGACC

CCAGCCTGGAAGCGCCGGCCACCCTCCAGATGCCCAGCCCGGCCTGTACTATTCCGCCAACGAGCA

GTGTAGGGTGGCCTTCGGCCCTAAGGCAGTGGCATGCACCTTTGCCAGAGAGCACCTGGACATGTGC

CAGGCCCTGTCCTGTCACACAGACCCCCTGGATCAGTCCTCTTGTTCTAGGCTGCTGGTGCCTCTGCT

GGATGGCACCGAGTGCGGCGTGGAGAAGTGGTGCAGCAAGGGCAGGTGTCGCTCCCTGGTGGAGCT

GACACCAATCGCAGCAGTGCACGGCCGCTGGAGCTCCTGGGGACCACGGAGCCCTTGCTCCAGATC

TTGTGGAGGAGGAGTGGTGACCCGGAGAAGGCAGTGTAACAATCCAAGGCCCGCCTTTGGCGGAAG

GGCATGCGTGGGAGCAGACCTGCAGGCCGAGATGTGCAATACCCAGGCCTGTGAGAAGACACAGCT

GGAGTTCATGTCCCAGCAGTGCGCAAGGACCGACGGACAGCCACTGAGATCTAGCCCTGGAGGAGC

ATCTTTTTATCACTGGGGAGCAGCAGTGCCACACAGCCAGGGCGATGCACTGTGCAGGCACATGTGC

CGCGCCATCGGCGAGTCTTTCATCATGAAGCGGGGCGACAGCTTTCTGGATGGAACCAGGTGTATGC

CATCCGGACCAAGGGAGGATGGCACCCTGTCTCTGTGCGTGAGCGGCTCCTGTCGGACATTCGGCTG

CGACGGCAGAATGGATAGCCAGCAAGTGTGGGACAGGTGCCAGGTGTGCGGAGGCGATAACTCTAC

-continued

CTGCAGCCCTAGGAAGGGATCTTTCACAGCAGGAAGGGCAAGAGAGTACGTGACGTTTCTGACCGT

GACACCAAACCTGACAAGCGTGTATATCGCCAATCACAGGCCCCTGTTTACCCACCTGGCCGTGCGG

ATCGGAGGCAGATACGTGGTGGCAGGCAAGATGTCTATCAGCCCAAATACCACATACCCATCCCTG

CTGGAGGACGGAAGGGTGGAGTATCGCGTGGCCCTGACAGAGGATCGGCTGCCTAGACTGGAGGAG

ATCAGGATCTGGGGACCACTGCAGGAGGACGCCGATATCCAGGTGTACCGCCGGTATGGCGAGGAG

TATGGCAATCTGACTCGCCCCGACATCACTTTCACATACTTCCAGCCCAAACCAAGGCAGGCA

AAGGGCGAGCTTGGTACCGAGCTCGGATCCGAA *GGTAAGCCTATC CCTAACCCTCTCC*

*TCGGTCTCGATTCTACG* CGTACCGGTCATCATCACCATCACCAT*TGA*GTTTAAACCCGCTGATCAGC

CTCGACTGTGCCTTCTAGTTGCCAGCCATCTGTTGTTTGCCCCTCCCCCGTGCCTTCCTTGACCCTGG

AAGGTGCCACTCCCACTGTCCTTTCCTAATAAAATGAGGAAATTGCATCGCATTGTCTGAGTAGGTG

TCATTCTATTCTGGGGGGTGGGGTGGGGCAGGACAGCAAGGGGGAGGATTGGGAAGACAATAGCA

GGCATGCTGGGGATGCGGTGGGCTCTATGGCTTCTGAGGCGGAAAGAACCAGCTGGGGCTCTAGGG

GGTATCCCCACGCGCCCTGTAGCGGCGCATTAAGCGCGGCGGGTGTGGTGGTTACGCGCAGCGTGA

CCGCTACACTTGCCAGCGCCCTAGCGCCCGCTCCTTTCGCTTTCTTCCCTTCCTTTCTCGCCACGTTCG

CCGGCTTTCCCCGTCAAGCTCTAAATCGGGGGTCCCTTTAGGGTTCCGATTTAGTGCTTTACGGCACC

TCGACCCCAAAAAACTTGATTAGGGTGATGGTTCACGTACCTAGAAGTTCCTATTCCGAAGTTCCTA

TTCTCTAGAAAGTATAGGAACTTCCTTGGCCAAAAAGCCTGAACTCACCGCGACGTCTGTCGAGAAG

TTTCTGATCGAAAAGTTCGACAGCGTCTCCGACCTGATGCAGCTCTCGGAGGGCGAAGAATCTCGTG

CTTTCAGCTTCGATGTAGGAGGGCGTGGATATGTCCTGCGGGTAAATAGCTGCGCCGATGGTTTCTA

CAAAGATCGTTATGTTTATCGGCACTTTGCATCGGCCGCGCTCCCGATTCCGGAAGTGCTTGACATT

GGGGAATTCAGCGAGAGCCTGACCTATTGCATCTCCCGCCGTGCACAGGGTGTCACGTTGCAAGACC

TGCCTGAAACCGAACTGCCCGCTGTTCTGCAGCCGGTCGCGGAGGCCATGGATGCGATCGCTGCGGC

CGATCTTAGCCAGACGAGCGGGTTCGGCCCATTCGGACCGCAAGGAATCGGTCAATACACTACATG

GCGTGATTTCATATGCGCGATTGCTGATCCCCATGTGTATCACTGGCAAACTGTGATGGACGACACC

GTCAGTGCGTCCGTCGCGCAGGCTCTCGATGAGCTGATGCTTTGGGCCGAGGACTGCCCCGAAGTCC

GGCACCTCGTGCACGCGGATTTCGGCTCCAACAATGTCCTGACGGACAATGGCCGCATAACAGCGG

TCATTGACTGGAGCGAGGCGATGTTCGGGGATTCCCAATACGAGGTCGCCAACATCTTCTTCTGGAG

GCCGTGGTTGGCTTGTATGGAGCAGCAGACGCGCTACTTCGAGCGGAGGCATCCGGAGCTTGCAGG

ATCGCCGCGGCTCCGGGCGTATATGCTCCGCATTGGTCTTGACCAACTCTATCAGAGCTTGGTTGA

CGGCAATTTCGATGATGCAGCTTGGGCGCAGGGTCGATGCGACGCAATCGTCCGATCCGGAGCCGG

GACTGTCGGGCGTACACAAATCGCCCGCAGAAGCGCGGCCGTCTGGACCGATGGCTGTGTAGAAGT

ACTCGCCGATAGTGGAAACCGACGCCCCAGCACTCGTCCGAGGGCAAAGGAATAGCACGTACTACG

AGATTTCGATTCCACCGCCGCCTTCTATGAAAGGTTGGGCTTCGGAATCGTTTTCCGGGACGCCGGC

TGGATGATCCTCCAGCGCGGGGATCTCATGCTGGAGTTCTTCGCCCACCCCAACTTGTTTATTGCAGC

TTATAATGGTTACAAATAAAGCAATAGCATCACAAATTTCACAAATAAAGCATTTTTTTCACTGCAT

TCTAGTTGTGGTTTGTCCAAACTCATCAATGTATCTTATCATGTCTGTATACCGTCGACCTCTAGCTA

GAGCTTGGCGTAATCATGGTCATAGCTGTTTCCTGTGTGAAATTGTTATCCGCTCACAATTCCACACA

ACATACGAGCCGGAAGCATAAAGTGTAAAGCCTGGGGTGCCTAATGAGTGAGCTAACTCACATTAA

TTGCGTTGCGCTCACTGCCCGCTTTCCAGTCGGGAAACCTGTCGTGCCAGCTGCATTAATGAATCGG

CCAACGCGCGGGGAGAGGCGGTTTGCGTATTGGGCGCTCTTCCGCTTCCTCGCTCACTGACTCGCTG

CGCTCGGTCGTTCGGCTGCGGCGAGCGGTATCAGCTCACTCAAAGGCGGTAATACGGTTATCCACAG

-continued

AATCAGGGGATAACGCAGGAAAGAACATGTGAGCAAAAGGCCAGCAAAAGGCCAGGAACCGTAAA

AAGGCCGCGTTGCTGGCGTTTTTCCATAGGCTCCGCCCCCCTGACGAGCATCACAAAAATCGACGCT

CAAGTCAGAGGTGGCGAAACCCGACAGGACTATAAAGATACCAGGCGTTTCCCCCTGGAAGCTCCC

TCGTGCGCTCTCCTGTTCCGACCCTGCCGCTTACCGGATACCTGTCCGCCTTTCTCCCTTCGGGAAGC

GTGGCGCTTTCTCATAGCTCACGCTGTAGGTATCTCAGTTCGGTGTAGGTCGTTCGCTCCAAGCTGGG

CTGTGTGCACGAACCCCCCGTTCAGCCCGACCGCTGCGCCTTATCCGGTAACTATCGTCTTGAGTCC

AACCCGGTAAGACACGACTTATCGCCACTGGCAGCAGCCACTGGTAACAGGATTAGCAGAGCGAGG

TATGTAGGCGGTGCTACAGAGTTCTTGAAGTGGTGGCCTAACTACGGCTACACTAGAAGGACAGTAT

TTGGTATCTGCGCTCTGCTGAAGCCAGTTACCTTCGGAAAAAGAGTTGGTAGCTCTTGATCCGGCAA

ACAAACCACCGCTGGTAGCGGTGGTTTTTTTGTTTGCAAGCAGCAGATTACGCGCAGAAAAAAAGG

ATCTCAAGAAGATCCTTTGATCTTTTCTACGGGGTCTGACGCTCAGTGGAACGAAAACTCACGTTAA

GGGATTTTGGTCATGAGATTATCAAAAAGGATCTTCACCTAGATCCTTTTAAATTAAAAATGAAGTT

TTAAATCAATCTAAAGTATATATGAGTAAACTTGGTCTGACAGTTACCAATGCTTAATCAGTGAGGC

ACCTATCTCAGCGATCTGTCTATTTCGTTCATCCATAGTTGCCTGACTCCCCGTCGTGTAGATAACTA

CGATACGGGAGGGCTTACCATCTGGCCCCAGTGCTGCAATGATACCGCGAGACCCACGCTCACCGG

CTCCAGATTTATCAGCAATAAACCAGCCAGCCGGAAGGGCCGAGCGCAGAAGTGGTCCTGCAACTT

TATCCGCCTCCATCCAGTCTATTAATTGTTGCCGGGAAGCTAGAGTAAGTAGTTCGCCAGTTAATAG

TTTGCGCAACGTTGTTGCCATTGCTACAGGCATCGTGGTGTCACGCTCGTCGTTTGGTATGGCTTCAT

TCAGCTCCGGTTCCCAACGATCAAGGCGAGTTACATGATCCCCCATGTTGTGCAAAAAAGCGGTTAG

CTCCTTCGGTCCTCCGATCGTTGTCAGAAGTAAGTTGGCCGCAGTGTTATCACTCATGGTTATGGCAG

CACTGCATAATTCTCTTACTGTCATGCCATCCGTAAGATGCTTTTCTGTGACTGGTGAGTACTCAACC

AAGTCATTCTGAGAATAGTGTATGCGGCGACCGAGTTGCTCTTGCCCGGCGTCAATACGGGATAATA

CCGCGCCACATAGCAGAACTTTAAAAGTGCTCATCATTGGAAAACGTTCTTCGGGGCGAAAACTCTC

AAGGATCTTACCGCTGTTGAGATCCAGTTCGATGTAACCCACTCGTGCACCCAACTGATCTTCAGCA

TCTTTTACTTTCACCAGCGTTTCTGGGTGAGCAAAAACAGGAAGGCAAAATGCCGCAAAAAAGGGA

ATAAGGGCGACACGGAAATGTTGAATACTCATACTCTTCCTTTTTCAATATTATTGAAGCATTTATCA

GGGTTATTGTCTCATGAGCGGATACATATTTGAATGTATTTAGAAAAATAAACAAATAGGGGTTCCG

CGCACATTTCCCCGAAAAGTGCCACCTGACGTC

Full-length wild type ADAMTS13 Amino Acid Sequence
(SEQ ID NO: 5)

MHQRHPRARCPPLCVAGILACGFLLGCWGPSHFQQSCLQALEPQAVSSYLSPGAPLKGRPPSPGFQRQRQ

RQRRAAGGILHLELLVAVGPDVFQAHQEDTERYVLTNLNIGAELLRDPSLGAQFRVHLVKMVILTEPEG

APNITANLTSSLLSVCGWSQTINPEDDTDPGHADLVLYITRFDLELPDGNRQVRGVTQLGGACSPTWSCLI

TEDTGFDLGVTIAHEIGHSFGLEHDGAPGSGCGPSGHVMASDGAAPRAGLAWSPCSRRQLLSLLSAGRA

RCVWDPPRPQPGSAGHPPDAQPGLYYSANEQCRVAFGPKAVACTFAREHLDMCQALSCHTDPLDQSSC

SRLLVPLLDGTECGVEKWCSKGRCRSLVELTPIAAVHGRWSSWGPRSPCSRSCGGGVVTRRRQCNNPRP

AFGGRACVGADLQAEMCNTQACEKTQLEFMSQQCARTDGQPLRSSPGGASFYHWGAAVPHSQGDALC

RHMCRAIGESFIMKRGDSFLDGTRCMPSGPREDGTLSLCVSGSCRTFGCDGRMDSQQVWDRCQVCGGD

NSTCSPRKGSFTAGRAREYVTFLTVTPNLTSVYIANHRPLFTHLAVRIGGRYVVAGKMSISPNTTYPSLLE

DGRVEYRVALTEDRLPRLEEIRIWGPLQEDADIQVYRRYGEEYGNLTRPDITFTYFQPKPRQAWVWAAV

RGPCSVSCGAGLRWVNYSCLDQARKELVETVQCQGSQQPPAWPEACVLEPCPPYWAVGDFGPCSASCG

-continued

GGLRERPVRCVEAQGSLLKTLPPARCRAGAQQPAVALETCNPQPCPARWEVSEPSSCTSAGGAGLALEN

ETCVPGADGLEAPVTEGPGSVDEKLPAPEPCVGMSCPPGWGHLDATSAGEKAPSPWGSIRTGAQAAHV

WTPAAGSCSVSCGRGLMELRFLCMDSALRVPVQEELCGLASKPGSRREVCQAVPCPARWQYKLAACSV

SCGRGVVRRILYCARAHGEDDGEEILLDTQCQGLPRPEPQEACSLEPCPPRWKVMSLGPCSASCGLGTAR

RSVACVQLDQGQDVEVDEAACAALVRPEASVPCLIADCTYRWHVGTWMECSVSCGDGIQRRRDTCLGP

QAQAPVPADFCQHLPKPVTVRGCWAGPCVGQGTPSLVPHEEAAAPGRTTATPAGASLEWSQARGLLFSP

APQPRRLLPGPQENSVQSSACGRQHLEPTGTIDMRGPGQADCAVAIGRPLGEVVTLRVLESSLNCSAGD

MLLLWGRLTWRKMCRKLLDMTFSSKTNTLVVRQRCGRPGGGVLLRYGSQLAPETFYRECDMQLFGPW

GEIVSPSLSPATSNAGGCRLFINVAPHARIAIHALATNMGAGTEGANASYILIRDTHSLRTTAFHGQQVLY

WESESSQAEMEFSEGFLKAQASLRGQYWTLQSWVPEMQDPQSWKGKEGT

Truncated Wild Type ADAMTS13 Amino Acid Sequence (SEQ ID NO: 6)

MHQRHPRARCPPLCVAGILACGFLLGCWGPSHFQQSCLQALEPQAVSSYLSPGAPLKGRPPSPGFQRQRQ

RQRRAAGGILHLELLVAVGPDVFQAHQEDTERYVLTNLNIGAELLRDPSLGAQFRVHLVKMVILTEPEG

APNITANLTSSLLSVCGWSQTINPEDDTDPGHADLVLYITRFDLELPDGNRQVRGVTQLGGACSPTWSCLI

TEDTGFDLGVTIAHEIGHSFGLEHDGAPGSGCGPSGHVMASDGAAPRAGLAWSPCSRRQLLSLLSAGRA

RCVWDPPRPQPGSAGHPPDAQPGLYYSANEQCRVAFGPKAVACTFAREHLDMCQALSCHTDPLDQSSC

SRLLVPLLDGTECGVEKWCSKGRCRSLVELTPIAAVHGRWSSWGPRSPCSRSCGGGVVTRRRQCNNPRP

AFGGRACVGADLQAEMCNTQACEKTQLEFMSQQCARTDGQPLRSSPGGASFYHWGAAVPHSQGDALC

RHMCRAIGESFIMKRGDSFLDGTRCMPSGPREDGTLSLCVSGSCRTFGCDGRMDSQQVWDRCQVCGGD

NSTCSPRKGSFTAGRAREYVTFLTVTPNLTSVYIANHRPLFTHLAVRIGGRYVVAGKMSISPNTTYPSLLE

DGRVEYRVALTEDRLPRLEEIRIWGPLQEDADIQVYRRYGEEYGNLTRPDITFTYFQPKPRQA mrADAMTS13 Amino Acid Sequence The codon optimized sequence provided the following amino acid sequence: Truncated WT ADAMTS13 ORF (1-685), V5 Tag (697-710; underlined), His Tag (714-719; bold) and Linker sequences (686-696 & 711-713; italics).

(SEQ ID NO: 7)

MHQRHPRARCPPLCVAGILACGFLLGCWGPSHFQQSCLQALEPQAVSSYLSPGAPLKGRPPSPGFQRQRQ

RQRRAAGGILHLELLVAVGPDVFQAHQEDTERYVLTNLNIGAELLRDPSLGAQFRVHLVKMVILTEPEG

APNITANLTSSLLSVCGWSQTINPEDDTDPGHADLVLYITRFDLELPDGNRQVRGVTQLGGACSPTWSCLI

TEDTGFDLGVTIAHEIGHSFGLEHDGAPGSGCGPSGHVMASDGAAPRAGLAWSPCSRRQLLSLLSAGRA

RCVWDPPRPQPGSAGHPPDAQPGLYYSANEQCRVAFGPKAVACTFAREHLDMCQALSCHTDPLDQSSC

SRLLVPLLDGTECGVEKWCSKGRCRSLVELTPIAAVHGRWSSWGPRSPCSRSCGGGVVTRRRQCNNPRP

AFGGRACVGADLQAEMCNTQACEKTQLEFMSQQCARTDGQPLRSSPGGASFYHWGAAVPHSQGDALC

RHMCRAIGESFIMKRGDSFLDGTRCMPSGPREDGTLSLCVSGSCRTFGCDGRMDSQQVWDRCQVCGGD

NSTCSPRKGSFTAGRAREYVTFLTVTPNLTSVYIANHRPLFTHLAVRIGGRYVVAGKMSISPNTTYPSLLE

DGRVEYRVALTEDRLPRLEEIRIWGPLQEDADIQVYRRYGEEYGNLTRPDITFTYFQPKPRQA*KGELGTEL*

*GSE*GKPIPNPLLGLDST*RTG*HHHHHH*

Encapsulation of mrADAMTS13 (SEQ ID NO: 7) Within a Poly(Lactide-Co-Glycolide) (PLGA) Microparticle to Provide Extended Release Given its molecular weight and physical properties, mrADAMTS13 (SEQ ID NO: 7) was physically encapsulated in a PLGA microparticle. To accomplish this, mrADAMTS13-loaded PLGA microparticles were fabricated using a water-in-oil-in-water (w/o/w) double emulsion method. As one example of such a procedure: Protein buffer solution (50 mL) containing 2 mg mrADAMTS13 protein (the internal aqueous phase, W1), was emulsified in 1 mL PLGA-dichloromethane (DCM) solution (5% w/v, the oil phase, 0) using a high-speed homogenizer. The first emulsion (W1/0) was then injected into 20 mL buffer solution containing 0.1% or 1% w/v PVA (the external aqueous phase, W2) at 400 rpm using a magnetic stirrer. The emulsion was continuously stirred in a fume hood to allow DCM evaporation and microparticle solidification. The mrADAMTS13-loaded microparticles were then collected by filtration, washed with DI water, and lyophilized. Particles 3 to 60 μm in diameter were produced, and characterized with respect to morphology, protein loading, and release kinetics.

Experimental Results mRNA Profile

The mRNA profiles of mrADAMTS13 and full-length wild type ADAMTS13 were evaluated. mrADAMTS13 demonstrates higher expression of mRNA compared to the full-length wild type ADAMTS13 against which fold changes were calculated (FIG. 1).

Molecular Weight

Figure 2:
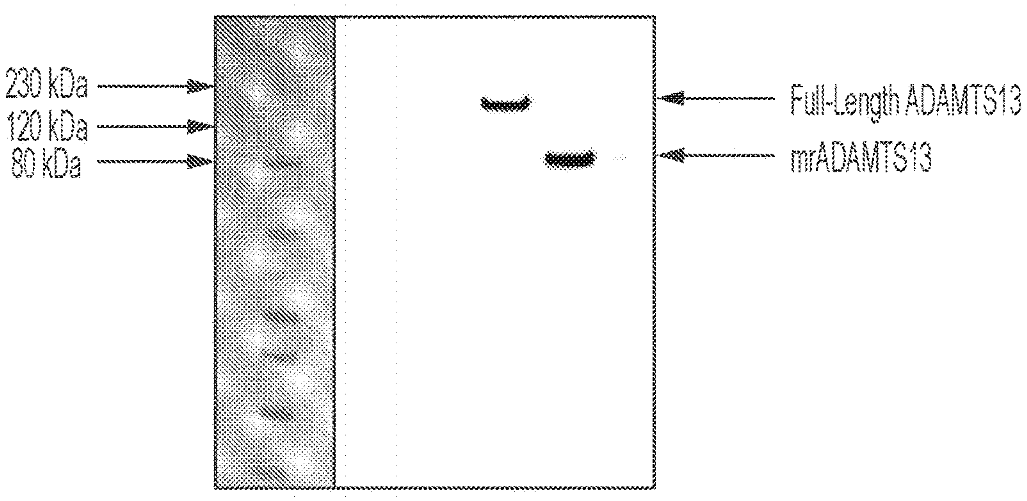
FIG. 2 depicts western blots of mrADAMTS13 (SEQ ID NO: 7) and full length wild-type ADAMTS13 (SEQ ID NO: 5).

Differences in molecular weight between mrADAMTS13 and full-length ADAMTS13 were demonstrated by western blot analysis (FIG. 2). mrADAMTS13 has a molecular weight of about 80 kDa.

Expression of mrADAMTS13 in Cells

Figure 3:
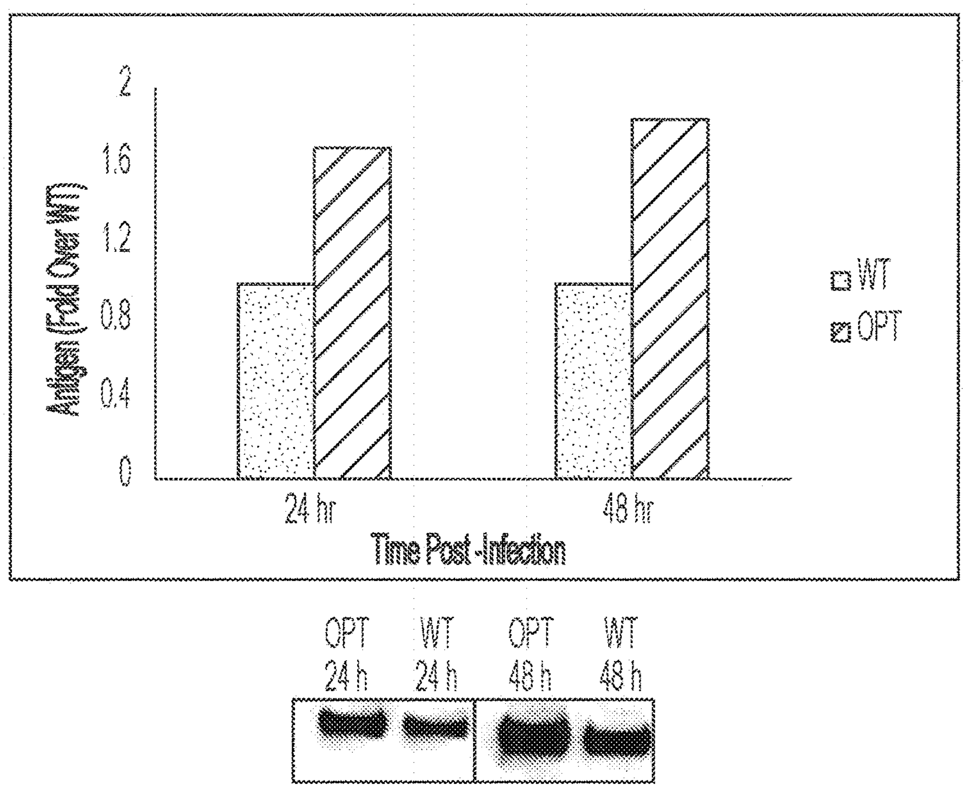
FIG. 3 depicts a plot of cell expression (Flp-In HEK293 cells) of mrADAMTS13 (OPT) (SEQ ID NO: 7) and truncated wild-type ADAMTS13 (WT) (SEQ ID NO: 6) and associated western blot analysis at 24 and 48 hours.
Figure 4:
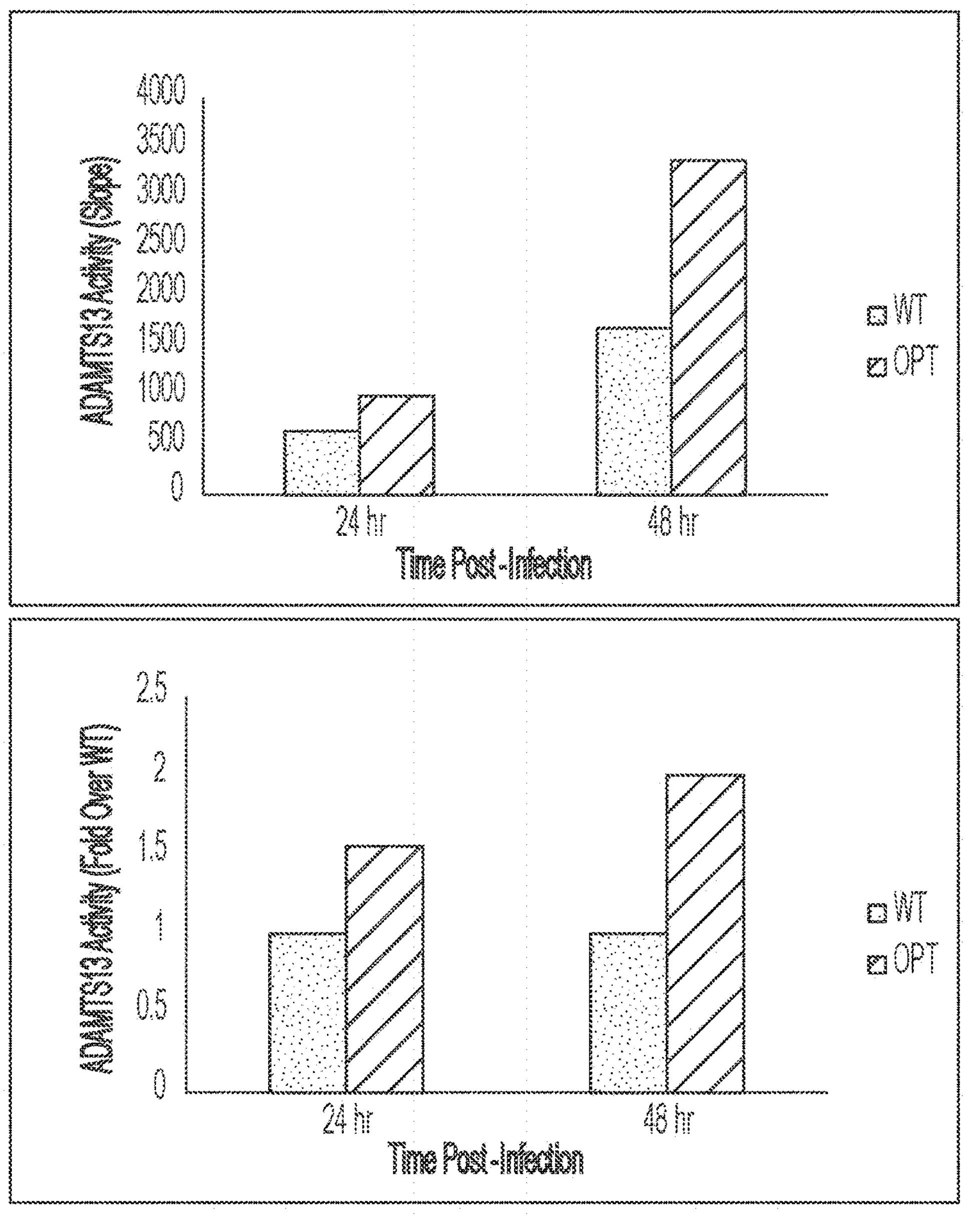
FIG. 4 is a series of plots showing enhanced cell expression (Flp-In HEK293 cells) and activity of mrADAMTS13 (OPT) (SEQ ID NO: 7) compared to truncated wild-type ADAMTS13 (WT) (SEQ ID NO: 6).

Expression characteristics of wild type truncated ADAMTS13 and mrADAMTS13 were tested simultaneously for expression in Flp-In HEK293 cells. Comparison of these molecules in parallel demonstrate the enhanced expression provided by codon optimization (FIG. 3).

mrADAMTS13 Demonstrates Enhanced Expression and Activity mrADAMTS13 demonstrated enhanced expression in Flp-In HEK293 cells and enhanced activity compared to truncated wild type ADAMTS13 measured by a VWF73-FRETS assay. ADAMTS13 activity of both variants was measured by VWF-73 FRETS assay and demonstrated enhanced activity of mrADAMTS13 compared to truncated wild type ADAMTS13 (FIG. 4).

Figure 5:
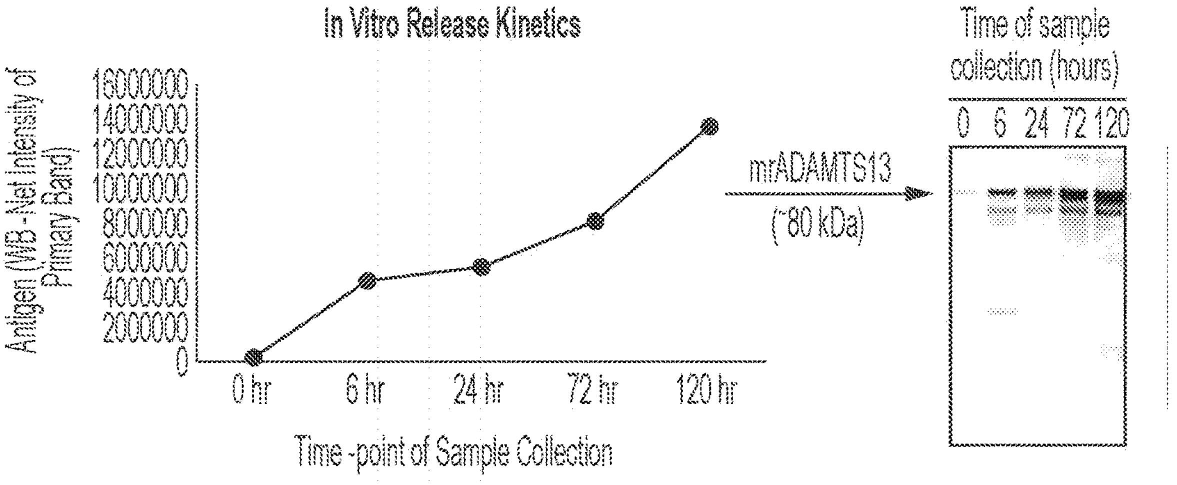
FIG. 5 depicts a plot of the in vitro release kinetics of mrADAMTS13 (SEQ ID NO: 7) from a PLGA-microparticle and associated western blot analysis at 0-120 hours.

Microencapsulation of mrADAMTS13 mrADAMTS13 was encapsulated into a PLGA-microparticle. The microencapsulated mrADAMTS13 demonstrated protein integrity and extended release of intact mrADAMTS13 over a period of 120 hours (FIG. 5).

Figure 6:
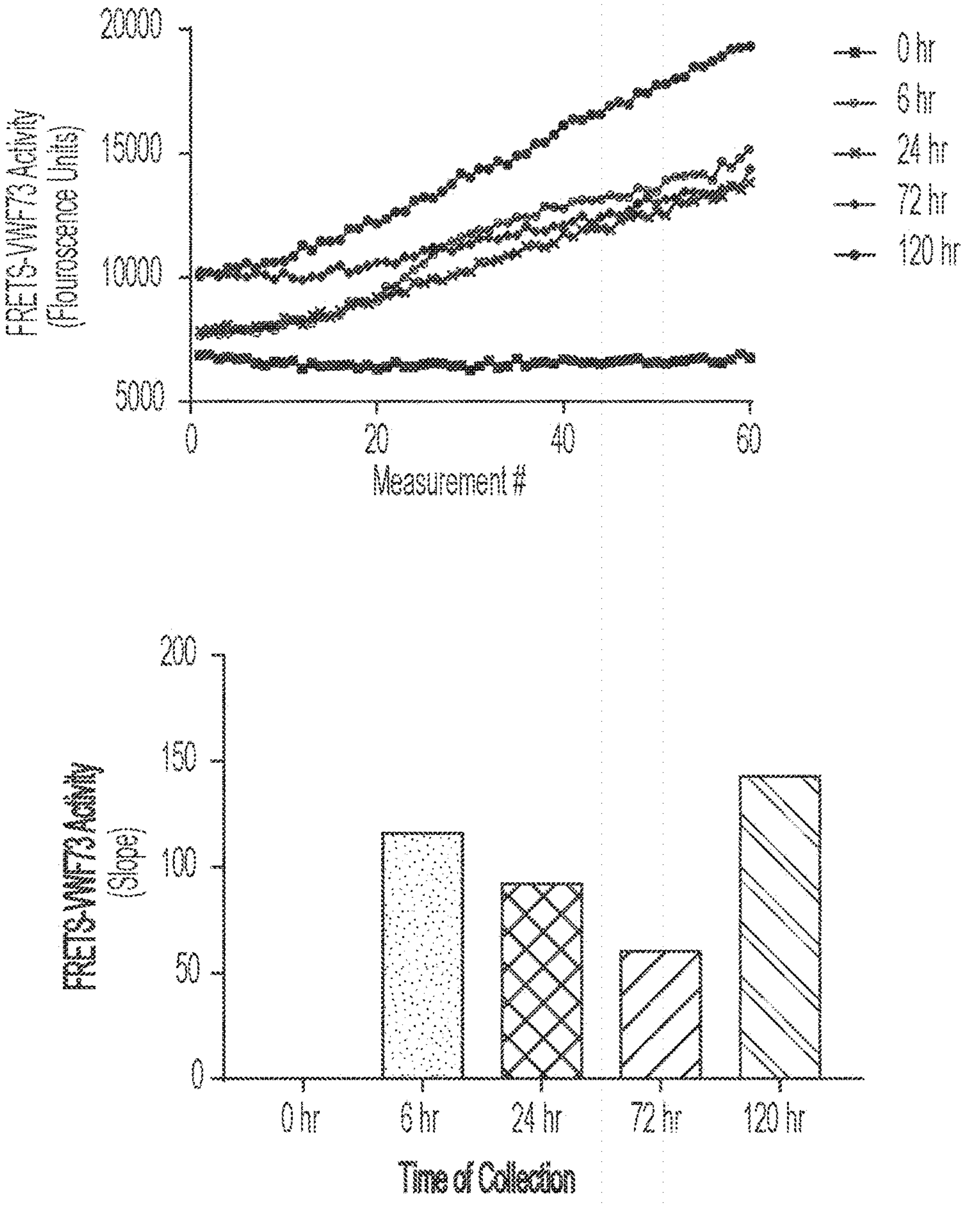
FIG. 6 is a series of plots showing extended release of active ADAMTS13 specific activity at 0-120 hours. Activity of mrADAMTS13 (SEQ ID NO: 7) was measured by VWF-73 FRETS assay. Data demonstrates preserved enzymatic ADAMTS13 specific activity at all 6, 24, 72, and 120-hour time points.
Figure 7:
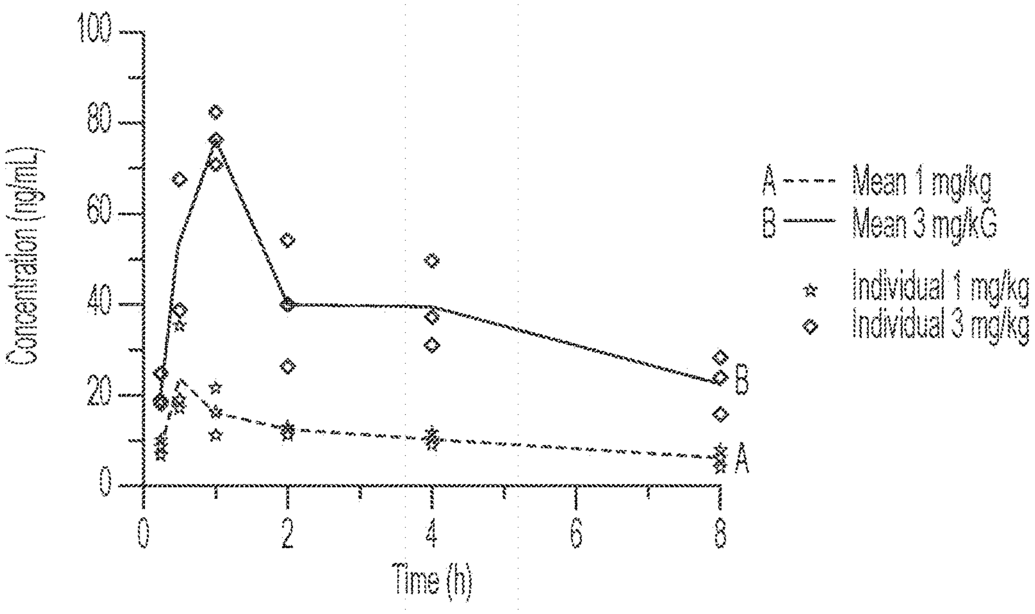
FIG. 7 is a linear plot of mean plasma concentration of ADAMTS13 after subcutaneous injection of mrADAMTS13 (SEQ ID NO: 7) in mice.
Figure 8:
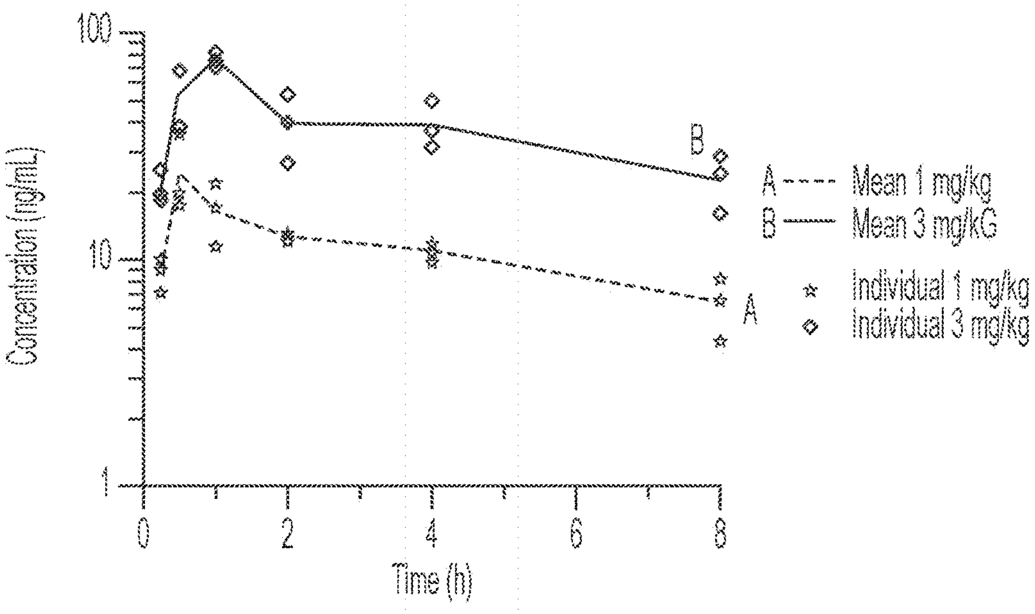
FIG. 8 is a semilog plot of mean plasma concentration of ADAMTS13 after subcutaneous injection of mrADAMTS13 (SEQ ID NO: 7) in mice.
Figure 9:
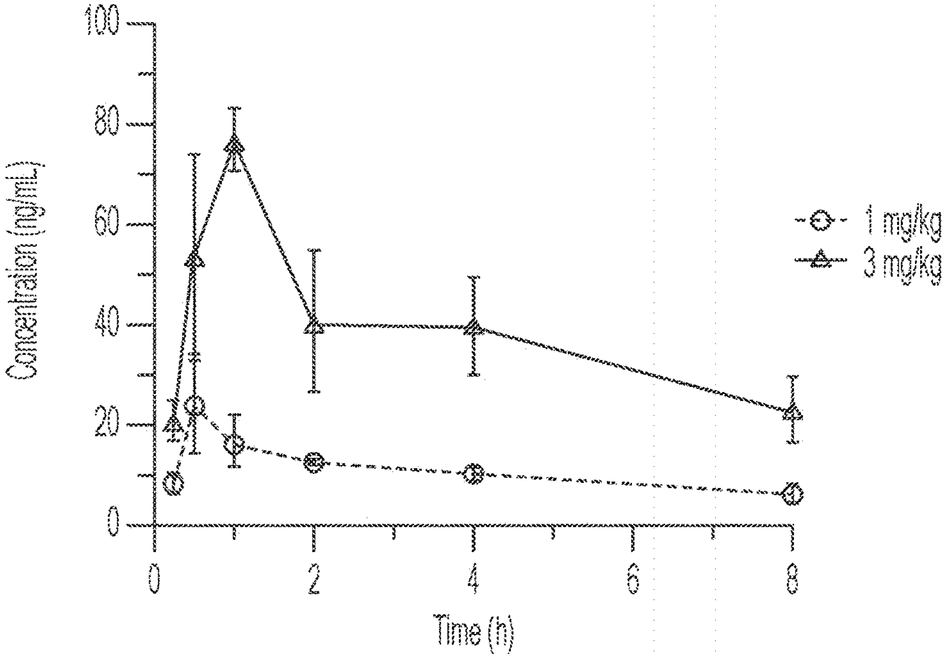
FIG. 9 is a linear plot (with standard deviation bars) of mean plasma concentration of ADAMTS13 after subcutaneous injection of mrADAMTS13 (SEQ ID NO: 7) in mice.
Figure 10:
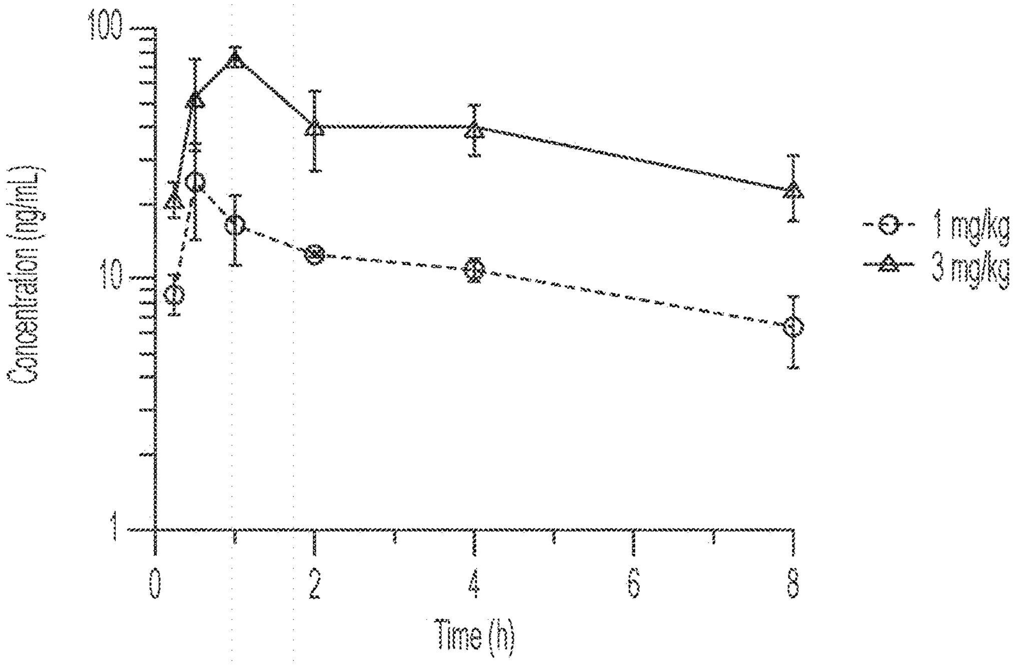
FIG. 10 is a semilog plot (with standard deviation bars) of mean plasma concentration of ADAMTS13 after subcutaneous injection of mrADAMTS13 (SEQ ID NO: 7) in mice.
Figure 11:
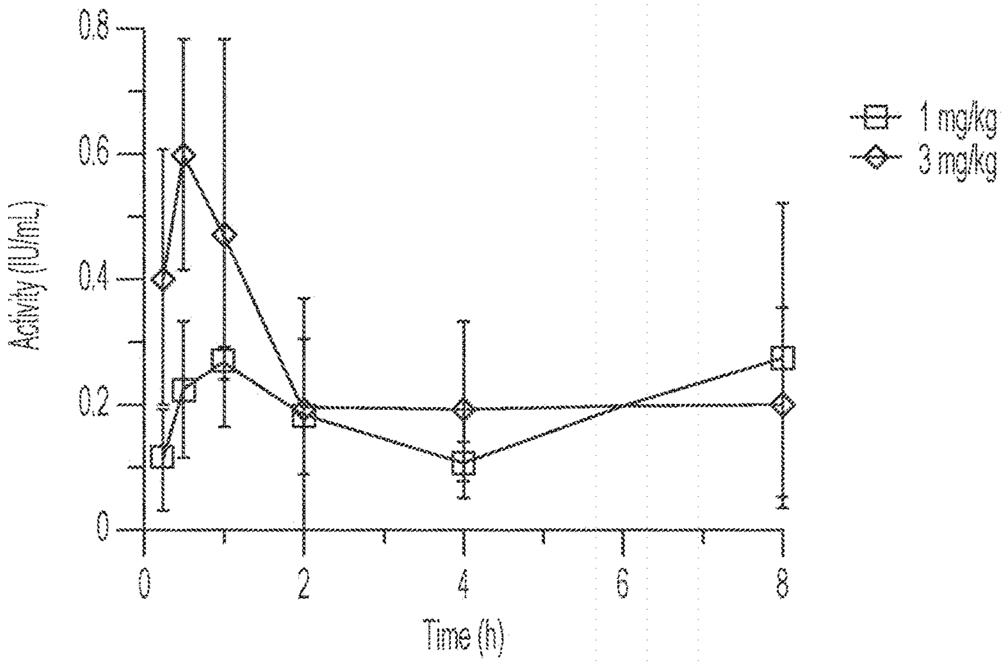
FIG. 11 is a linear plot of mean ADAMTS13 plasma activity after subcutaneous injection of mrADAMTS13 (SEQ ID NO: 7) in mice.
Figure 12:
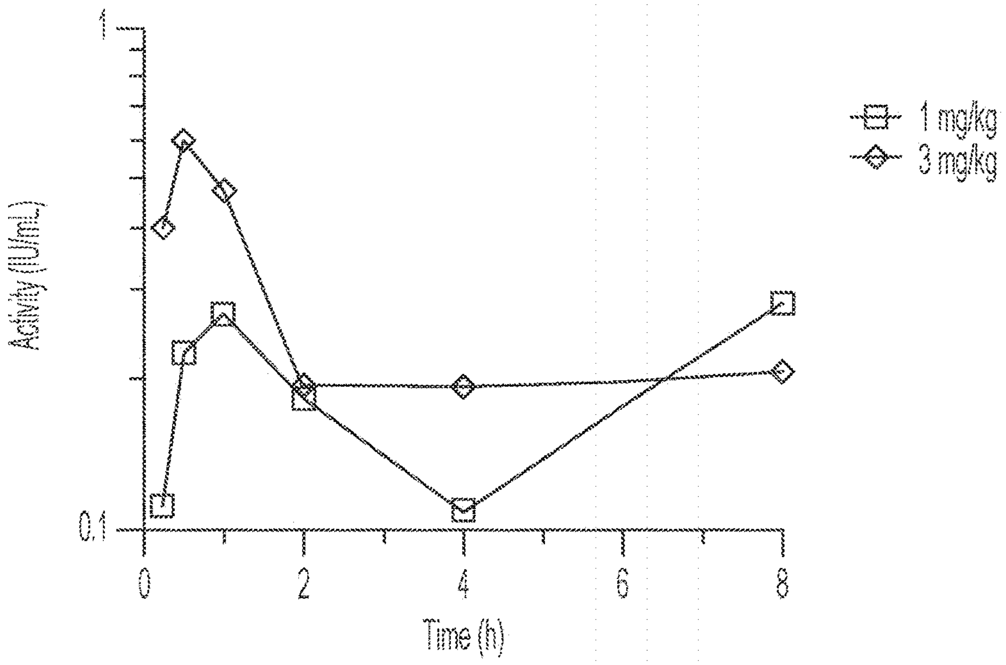
FIG. 12 is a semilog plot of mean ADAMTS13 plasma activity after subcutaneous injection of mrADAMTS13 (SEQ ID NO: 7) in mice.
Figure 13:
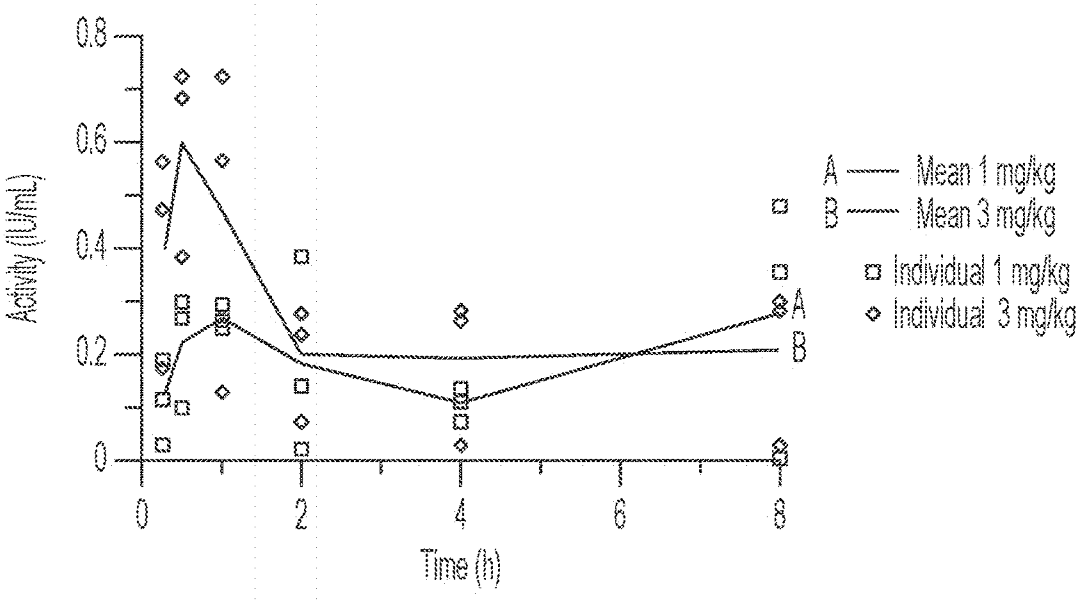
FIG. 13 is a linear plot of mean ADAMTS13 plasma activity with native ADAMTS13 subtracted after subcutaneous injection of mrADAMTS13 (SEQ ID NO: 7) in mice.
Figure 14:
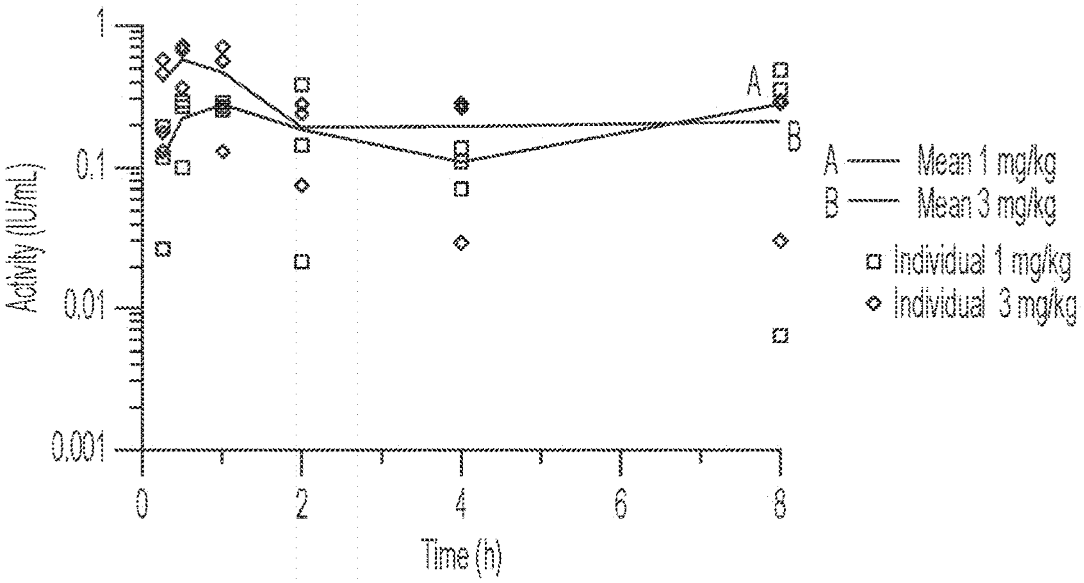
FIG. 14 is a semilog plot of mean ADAMTS13 plasma activity with native ADAMTS13 subtracted after subcutaneous injection of mrADAMTS13 (SEQ ID NO: 7) in mice.

The PLGA-microencapsulated mrADAMTS13 also demonstrated extended release of active ADAMTS13 specific activity. FIG. 6 shows ADAMTS13 specific activity in individual samples at 0, 6, 24, 72, and 120 hours during a release experiment of mrADAMTS13 into supernatant. Data was obtained by a fluorescent emission (FRETS VWF-73) of a total of 60 measurements over time. This data describes the slope of enzymatic activity of each individual sample. This data demonstrates active ADAMTS13 enzyme is present in all samples including at 120 hours.

These data demonstrate that mrADAMTS13 demonstrates preserved cellular expression and specific ADAMTS13 activity. Moreover, mrADAMTS13 can be encapsulated into a PLGA microparticle providing extended release of ADAMTS13 enzymatic activity.

Pharmacokinetic Properties of Single Dose Subcutaneous Injection of mrADAMTS13 (SEQ ID NO: 7)

The objective was to assess the plasma uptake and pharmacokinetic characteristics of mrADAMTS13 when injected subcutaneously to a mouse model over a period 8 hours. This was designed to understand the basic properties of mrADAMTS13 as a recombinant truncation protein to diffuse and represent in plasma a minimum plasma concentration and exert a minimum ADAMTS13 activity. Clinically this is of great impact because the current administration of recombinant ADAMTS13 is only available commercially in the intravenous formulation requiring repeated intravenous injections to patients. This practice incurs significant risk of life threating blood infections from repeated injections. In addition, the intravenous formulation has a limited half-life as single dose with the potential disadvantage of an initial high-peak plasma concentration, which predisposes patients to the development of antibodies against recombinant ADAMTS13. An experiment was designed to evaluate the plasma concentration and pharmacokinetic parameters after a single injection of mrADAMTS13 with the intent to demonstrate dose dependency and metabolism consistent with a predictable absorption of mrADAMTS13 into plasma.

Study Design

A total of 18 male mice were selected for the experiment and divided into two groups receiving either 1 mg/Kg or 3 mg/Kg subcutaneously under sterile conditions as described in the table below.

| Group | No. of Animals | No. of Animals per Cohort | Sex | Route of Administration | Dose (mg/kg) | Volume (mL/kg) | Conc. (mg/mL) | Test Article |
|---|---|---|---|---|---|---|---|---|
| 1 | 9 | 3 | M | Single | 1 | 10 | 0.1 | mrAD |
| 2 | 9 | 3 | M | dose: SC | 3 | 10 | 0.3 | mrAD |

A scheduled sampling technique included whole blood sample collection of a tail nick into a citrated pediatric tube. After 5 minutes at bench top, the sample was centrifuged and plasma collected and stored at −20° C. degrees.

Sample Collection

| Group | Cohort | Sample Collected | Tail nick time point (h) | Terminal time point (h) |
|---|---|---|---|---|
| 1-2 | 1 | Blood: Tail | 0.25 | 2 |
| 1-2 | 2 | nick then | 0.5 | 4 |
| 1-2 | 3 | Cardiac stick | 1 | 8 |

Identification

The animals were marked 1-18 with an indelible marker for identification and monitoring purposes.

Animal Health and Acclimation

Animals were acclimated for 24-48 h after arrival to the laboratory. Before the start of the in-life phase, each animal was examined and weighed prior to mrADAMTS13 administration.

Housing and Feed Conditions

The animal room environment is controlled according to facility operations: temperature range of 69-75° F., relative humidity in the range of 30-70% and a 12-hour artificial light/dark cycle. Animals were group or separately housed in polycarbonate caging with contact bedding and rodent enrichment. All animals had free access to food (standard Envigo Rodent #2016 diet) and automatic municipal water, particulate and charcoal filtered.

Justification of Species and Number

This is an acceptable species to support PK studies for compounds under development for use in humans. The number of animals in each group is the minimum number of animals necessary for assessment of interanimal variability.

Experimental Procedures mrADAMTS13 Formulation mrADAMTS13 was formulated in Tris or Phosphate buffer at 0.1 mg/mL and 0.3 mg/mL for the two dose groups of 1 mg/kg and 3 mg/kg.

Test Article Administration mrADAMTS13 was administered by subcutaneous injection using a syringe and hubless 27-29 G needle to reduce the sample volume loss.

Body Weight

Animals were weighed upon arrival and repeated the day of dosing. They were dosed on a body weight basis determined from their last recorded body weight.

Sample Collection 150 uL blood was collected by tail nick for the first time point and then the maximal volume by cardiac stick for the second, terminal time point in each mouse. Blood was collected in sodium citrate collection tubes. The plasma will be spun and collected within 30 minutes of collection. The resulting plasma will be divided into two equal aliquots for the tail nick collection, and three equal aliquots for the terminal blood draw. Plasma is separated and stored frozen at −20° C. until shipment.

Disposition of Animals

Following the collection of the second blood sample, via cardiac stick, animals will be euthanized by carbon dioxide asphyxiation and cervical dislocation before collecting additional samples.

Data Analysis

Bioanalytical Sample Analysis

Plasma samples were assayed for both mrADAMTS13 concentration and activity. mrADAMTS13 was assayed for concentration in plasma using an ELISA methodology and results expressed in ng/mL of plasma. mrADAMTS13 activity was assayed using an ADAMTS13 specific activity assay employing GST-VWF73 substrate and the data expressed as U/mL of plasma.

Pharmacokinetic (PK) Analysis

Standard non-compartmental PK analyses were assessed using Phoenix Winnonlin v8.3 software. Parameter estimation will be by the linear up/log down trapezoidal method for parameter estimation. Parameters included Tmax, Cmax, AUClast, AUCinf, half-life and volume of distribution.

Results

After the injection all animals tolerated mrADAMTS13 without any symptoms and survived the protocol without any deleterious effects. There was no appreciable local reaction at the injection site and animals regained normal activity after the injection of mrADAMTS13. Sampling of the mrADAMTS13 plasma concentration by non-compartmental analysis demonstrated a good proportionality between the 1 and 3 mg/Kg doses suggesting dose dependent plasmatic absorption from the subcutaneous space into plasma. Table 1 describes the basic PK characteristics and summarized as increased half-life with increasing dose (1 to 3 mg/Kg), maximum observed concentrations (Cmax) of 24.1 and 76.4 ng/mL of plasma. There was good dose dependent proportionality in area under the curve from the time of dosing to the time of the measurable concentration (AUCinf). This data overall indicates that mrADAMTS13 has a mathematical predicable peak of plasma concentrations, rate of metabolism and volume of distribution consistent with a positive absorption phase from the subcutaneous to plasma compartments. Tables 2 and 3 describe the data for concentration for individual doses and animals.

TABLE 1

Sparse Sampling NCA Concentration PK Parameters of mrADAMTS13

| Dose (mg/kg) | T1/2 (h) | Tmax (h) | Cmax (ng/ml) | Cmax/D (kg*ng/ml/mg) | AUClast (h*ng/ml) | AUClast/D (h*kg*ng/ml/mg) |
|---|---|---|---|---|---|---|
| 1 | 6.12 | 0.500 | 24.1 | 24.1 | 86.6 | 86.6 |
| 3 | 6.91 | 1.00 | 76.4 | 25.5 | 302 | 101 |

| Dose (mg/kg) | AUCinf (h*ng/ml) | AUCinf/D (h*kg*ng/ml/mg) | % Extrap (%) | Vz/F (mL/kg) | Cl/F (mL/h/kg) | MRTlast (h) |
|---|---|---|---|---|---|---|
| 1 | 144 | 144 | 39.7 | 61500 | 6960 | 3.42 |
| 3 | 530 | 177 | 43.0 | 56400 | 5660 | 3.51 |

TABLE 2

Individual Concentration Time Table with Summary Statistics of mrADAMTS13

| Dose (mg/kg) | Animal | 0.25 | 0.50 | 1.0 | 2.0 | 4.0 | 8.0 |
|---|---|---|---|---|---|---|---|
| | | Time (h) / Concentration (ng/ml) | | | | | |
| 1 | 1 | 8.96 | | | 12.1 | | |
| | 2 | 10.0 | | | 12.8 | | |
| | 3 | 7.15 | | | 12.9 | | |
| | 4 | | 35.2 | | | 10.8 | |
| | 5 | | 19.5 | | | 9.60 | |
| | 6 | | 17.5 | | | 11.8 | |
| | 7 | | | 21.6 | | | 8.29 |
| | 8 | | | 11.2 | | | 6.70 |
| | 9 | | | 17.0 | | | 4.38 |
| | N | 3 | 3 | 3 | 3 | 3 | 3 |
| | Mean | 8.70 | 24.1 | 16.6 | 12.6 | 10.7 | 6.46 |
| | SD | 1.44 | 9.74 | 5.19 | 0.440 | 1.09 | 1.97 |
| | CV % | 16.6 | 40.5 | 31.3 | 3.50 | 10.2 | 30.5 |
| | Median | 8.96 | 19.5 | 17.0 | 12.8 | 10.8 | 6.70 |

TABLE 3

Individual Concentration Time Table with Summary Statistics of mrADAMTS13

| Dose (mg/kg) | Animal | 0.25 | 0.50 | 1.0 | 2.0 | 4.0 | 8.0 |
|---|---|---|---|---|---|---|---|
| | | Time (h) / Concentration (ng/ml) | | | | | |
| 3 | 10 | 19.3 | | | 26.5 | | |
| | 11 | 18.4 | | | 40.1 | | |
| | 12 | 25.0 | | | 54.3 | | |
| | 13 | | 38.6 | | | 37.1 | |
| | 14 | | 67.7 | | | 49.7 | |
| | 15 | | | | | 31.6 | |
| | 16 | | | 70.8 | | | 24.0 |
| | 17 | | | 82.6 | | | 28.6 |
| | 18 | | | 75.9 | | | 16.1 |
| | N | 3 | 2 | 3 | 3 | 3 | 3 |
| | Mean | 20.9 | 53.1 | 76.4 | 40.3 | 39.5 | 22.9 |
| | SD | 3.59 | 20.6 | 5.94 | 13.9 | 9.30 | 6.33 |
| | CV % | 17.2 | 38.7 | 7.77 | 34.6 | 23.5 | 27.7 |
| | Median | 19.3 | 53.1 | 75.9 | 40.1 | 37.1 | 24.0 |

FIGS. 7-10 depict the curves for concentration change compared to time (0) of administration and time points. This is represented as linear, semi logarithmic, including variability from the mean in linear and semi logarithmic respectively.

Sampling of the mrADAMTS13 plasma activity was calculated by subtraction of the baseline (native ADAMTS13) activity and the PK characteristics described in Table 4. This data demonstrates good proportionality between 1 and 3 mg/Kg doses, suggesting increased plasma ADAMTS13 over the baseline native ADAMTS13 activity. FIGS. 11-14 depict the curves for ADAMTS13 activity change against time (0) of administration and time points. This is represented as linear, semi logarithmic, including variability from the mean in linear and semi logarithmic respectively.

TABLE 4

Sparse Sampling Background Subtracted Activity PK Parameters of mrADAMTS13

| Dose (mg/kg) | Tmax (h) | Cmax (IU/mL) | Cmax/D (kg*IU/mL/mg) | AUClast (h*IU/mL) | AUClast/D (h*kg*IU/mL/mg) |
|---|---|---|---|---|---|
| 1 | 8.00 | 0.279 | 0.279 | 1.46 | 1.46 |
| 3 | 0.500 | 0.597 | 0.199 | 1.94 | 0.646 |

| Dose (mg/kg) | AUCinf (h*IU/mL) | AUCinf/D (h*kg*IU/mL/mg) | % Extrap (%) | MRTlast (h) |
|---|---|---|---|---|
| 1 | 2.40 | 2.40 | 39.1 | 4.52 |
| 3 | 4.57 | 1.52 | 57.6 | 3.45 |

TABLE 5

Individual Background Subtracted Time Table with Summary Statistics of mrADAMTS13

| Dose (mg/kg) | Animal | 0.25 | 0.50 | 1.0 | 2.0 | 4.0 | 8.0 |
|---|---|---|---|---|---|---|---|
| | | Time (h) / Background Subtracted Activity (IU/mL) | | | | | |
| 1 | 1 | 0.190 | | | 0.0223 | | |
| | 2 | 0.0262 | | | 0.384 | | |
| | 3 | 0.116 | | | 0.143 | | |
| | 4 | | 0.100 | | | 0.116 | |
| | 5 | | 0.301 | | | 0.137 | |
| | 6 | | 0.270 | | | 0.0725 | |

TABLE 5-continued

Individual Background Subtracted Time Table with Summary Statistics of mrADAMTS13

| Dose (mg/kg) | Animal | 0.25 | 0.50 | 1.0 | 2.0 | 4.0 | 8.0 |
|---|---|---|---|---|---|---|---|
| | | Time (h) / Background Subtracted Activity (IU/mL) | | | | | |
| | 7 | | | 0.291 | | | 0.477 |
| | 8 | | | 0.250 | | | 0.352 |
| | 9 | | | 0.265 | | | 0.00658 |
| | N | 3 | 3 | 3 | 3 | 3 | 3 |
| | Mean | 0.111 | 0.224 | 0.269 | 0.183 | 0.109 | 0.279 |
| | SD | 0.0822 | 0.108 | 0.0208 | 0.184 | 0.0330 | 0.244 |
| | CV % | 74.1 | 48.3 | 7.72 | 101 | 30.4 | 87.5 |
| | Median | 0.116 | 0.270 | 0.265 | 0.143 | 0.116 | 0.352 |

TABLE 6

Individual Background Subtracted Time Table with Summary Statistics of mrADAMTS13

| Dose (mg/kg) | Animal | 0.25 | 0.50 | 1.0 | 2.0 | 4.0 | 8.0 |
|---|---|---|---|---|---|---|---|
| | | Time (h) / Background Subtracted Activity (IU/mL) | | | | | |
| 3 | 10 | 0.174 | | | 0.0750 | | |
| | 11 | 0.472 | | | 0.238 | | |
| | 12 | 0.564 | | | 0.276 | | |
| | 13 | | 0.723 | | | 0.281 | |
| | 14 | | 0.685 | | | 0.263 | |
| | 15 | | 0.384 | | | 0.0298 | |
| | 16 | | | 0.568 | | | 0.0298 |
| | 17 | | | 0.725 | | | 0.285 |
| | 18 | | | 0.128 | | | 0.300 |
| | N | 3 | 3 | 3 | 3 | 3 | 3 |
| | Mean | 0.403 | 0.597 | 0.474 | 0.196 | 0.191 | 0.205 |
| | SD | 0.204 | 0.186 | 0.309 | 0.107 | 0.140 | 0.152 |
| | CV % | 50.6 | 31.1 | 65.3 | 54.4 | 73.3 | 74.1 |
| | Median | 0.472 | 0.685 | 0.568 | 0.238 | 0.263 | 0.285 |

The data on the pharmacokinetics of subcutaneously injected mrADAMTS13 demonstrates that mrADAMTS13 molecular structure and enzymatic properties are present in plasma after subcutaneous injection over an experimental period of 8 hours. This data using an in vivo animal model demonstrates that subcutaneous supplementation of ADAMTS13 activity is achievable using mrADAMTS13. The metabolic properties displayed by mrADAMTS13 in terms of peak of activity, duration of activity and volume of distribution are consistent with preserved mrADAMTS13 function and active metabolism in a dose dependent manner.

Equivalents and Scope

Those skilled in the art will recognize, or be able to ascertain using no more than routine experimentation, many equivalents of the embodiments described herein. The scope of the present disclosure is not intended to be limited to the above description, but rather is as set forth in the appended claims.

Articles such as "a," "an," and "the" may mean one or more than one unless indicated to the contrary or otherwise evident from the context. Claims or descriptions that include "or" between two or more members of a group are considered satisfied if one, more than one, or all of the group members are present, unless indicated to the contrary or otherwise evident from the context. The disclosure of a group that includes "or" between two or more group members provides embodiments in which exactly one member of the group is present, embodiments in which more than one members of the group are present, and embodiments in which all of the group members are present. For purposes of brevity those embodiments have not been individually spelled out herein, but it will be understood that each of these embodiments is provided herein and may be specifically claimed or disclaimed.

It is to be understood that the disclosure encompasses all variations, combinations, and permutations in which one or more limitation, element, clause, or descriptive term, from one or more of the claims or from one or more relevant portion of the description, is introduced into another claim. For example, a claim that is dependent on another claim can be modified to include one or more of the limitations found in any other claim that is dependent on the same base claim. Furthermore, where the claims recite a composition, it is to be understood that methods of making or using the composition according to any of the methods of making or using disclosed herein or according to methods known in the art, if any, are included, unless otherwise indicated or unless it would be evident to one of ordinary skill in the art that a contradiction or inconsistency would arise.

Where elements are presented as lists, e.g., in Markush group format, it is to be understood that every possible subgroup of the elements is also disclosed, and that any element or subgroup of elements can be removed from the group. It is also noted that the term "comprising" is intended to be open and permits the inclusion of additional elements or steps. It should be understood that, in general, where an embodiment, product, or method is referred to as comprising particular elements, features, or steps, embodiments, products, or methods that consist, or consist essentially of, such elements, features, or steps, are provided as well. For purposes of brevity those embodiments have not been individually spelled out herein, but it will be understood that each of these embodiments is provided herein and may be specifically claimed or disclaimed.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in certain embodiments, to the tenth of the unit of the lower limit of the range, unless the context clearly dictates otherwise. For purposes of brevity, the values in each range have not been individually spelled out herein, but it will be understood that each of these values is provided herein and may be specifically claimed or disclaimed. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

Where websites are provided, URL addresses are provided as non-browser-executable codes, with periods of the respective web address in parentheses. The actual web addresses do not contain the parentheses.

In addition, it is to be understood that any particular embodiment of the present disclosure may be explicitly excluded from any one or more of the claims. Where ranges are given, any value within the range may explicitly be excluded from any one or more of the claims. Any embodiment, element, feature, application, or aspect of the compositions and/or methods of the disclosure, can be excluded from any one or more claims. For purposes of brevity, all of the embodiments in which one or more elements, features, purposes, or aspects is excluded are not set forth explicitly herein.

What is claimed is:

1. A polypeptide comprising a sequence having at least 96% amino acid sequence identity to SEQ ID NO: 7 (mrADAMTS13), wherein the polypeptide is not SEQ ID NO: 5 (ADAMTS13).

2. The polypeptide of claim 1, wherein the polypeptide comprises a sequence having at least 97% amino acid sequence identity to SEQ ID NO: 7.

3. The polypeptide of claim 1, wherein the polypeptide comprises a sequence having at least 99% or at least 99.5% amino acid sequence identity to SEQ ID NO: 7.

4. The polypeptide of claim 1, wherein the polypeptide comprises SEQ ID NO: 7.

5. The polypeptide of claim 1, wherein the polypeptide consists of SEQ ID NO: 7.

6. The polypeptide of claim 1, wherein the polypeptide is a recombinant protein.

7. A nucleic acid molecule comprising a nucleotide sequence encoding the polypeptide of claim 1.

8. The nucleic acid molecule of claim 7, wherein the nucleotide sequence has at least 85%, 87%, 90%, 92%, 95%, 97%, 99%, or 99.5% sequence identity to the nucleotide sequence of SEQ ID NO: 3.

9. A vector comprising the nucleic acid molecule of claim 7.

10. A cell comprising the polypeptide of claim 1.

11. A pharmaceutical composition comprising the polypeptide of claim 1 and a pharmaceutically acceptable carrier.

12. A kit comprising the polypeptide of claim 1 or a pharmaceutical composition comprising the polypeptide and a pharmaceutically acceptable carrier; and instructions for use.

13. A drug delivery composition comprising the polypeptide of claim 1.

14. The drug delivery composition of claim 13, wherein the drug delivery composition comprises a microparticle.

15. The drug delivery composition of claim 14, wherein the microparticle comprises poly(lactic-co-glycolic acid), poly(lactic acid), poly(glycolic acid), poly(lactic-co-glycolic acid)-poly(ethylene glycol)copolymer, poly(lactic acid)-poly(ethylene glycol)copolymer, or poly(glycolic acid)-poly(ethylene glycol) copolymer.

16. A pharmaceutical composition comprising the drug delivery composition of claim 13, and optionally a pharmaceutically acceptable carrier.

17. A method of producing the polypeptide of claim 1, the method comprising culturing a cell comprising the polypeptide in a culturing media, under conditions that allow the polypeptide to express.

18. A method of preparing a microparticle comprising the polypeptide of claim 1, the method comprising:
- emulsifying the polypeptide in a solution containing a polymer to provide a first emulsification;
- emulsifying the first emulsification in a solution containing an emulsifying agent to provide a second emulsification;
- evaporating solvent; and
- isolating the microparticle.

19. A method of treating or preventing a thrombotic disease or condition, the method comprising administering to a subject in need thereof a therapeutically effective amount of the polypeptide of claim 1, or a pharmaceutical composition comprising the polypeptide and a pharmaceutically acceptable carrier.

20. A method of cleaving von Willebrand factor (VWF), the method comprising contacting the polypeptide of claim 1 or a pharmaceutical composition comprising the polypeptide and a pharmaceutically acceptable carrier, with VWF.

21. A method of treating or preventing a thrombotic disease or condition, the method comprising administering to a subject in need thereof a therapeutically effective amount of the drug delivery composition of claim 13, or a pharmaceutical composition comprising the drug delivery composition.

* * * * *